US010113156B2

(12) United States Patent
Lambowitz et al.

(10) Patent No.: US 10,113,156 B2
(45) Date of Patent: Oct. 30, 2018

(54) STABILIZED REVERSE TRANSCRIPTASE FUSION PROTEINS

(75) Inventors: Alan M. Lambowitz, Austin, TX (US); Sabine Mohr, Austin, TX (US); Georg Mohr, Austin, TX (US); Eman Ghanem, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 825 days.

(21) Appl. No.: 13/254,223

(22) PCT Filed: Mar. 4, 2010

(86) PCT No.: PCT/US2010/026165
§ 371 (c)(1),
(2), (4) Date: Sep. 1, 2011

(87) PCT Pub. No.: WO2010/102085
PCT Pub. Date: Sep. 10, 2010

(65) Prior Publication Data
US 2012/0009630 A1 Jan. 12, 2012

Related U.S. Application Data

(60) Provisional application No. 61/157,332, filed on Mar. 4, 2009.

(51) Int. Cl.
*C12N 9/12* (2006.01)
*C12P 19/34* (2006.01)

(52) U.S. Cl.
CPC ............ *C12N 9/1276* (2013.01); *C12P 19/34* (2013.01); *C12Y 207/07049* (2013.01); *C07K 2319/00* (2013.01); *C07K 2319/24* (2013.01)

(58) Field of Classification Search
None
See application file for complete search history.

(56) References Cited

U.S. PATENT DOCUMENTS

| 5,322,770 A | 6/1994 | Gilfand |
| 5,643,758 A | 7/1997 | Guan et al. |
| 5,654,176 A | 8/1997 | Smith |
| 5,736,373 A * | 4/1998 | Hamilton ............... 435/194 |
| 6,627,424 B1 | 9/2003 | Wang |
| 7,001,745 B1 | 2/2006 | Yu et al. |
| 7,094,539 B2 | 8/2006 | Gu et al. |
| 2004/0157300 A1 | 8/2004 | Burger et al. |
| 2008/0118949 A1 | 5/2008 | Hsieh et al. |

FOREIGN PATENT DOCUMENTS

WO 2005/084409 9/2005

OTHER PUBLICATIONS

Kapust and Waugh, Protein Science, vol. 8, pp. 1688-1674, 1999.*
International Search Report and Written Opinion from International Application No. PCTUS2010/26165, dated Sep. 23, 2010.
Fox, et al. "Single amino acid substitutions on the surface of *Escherichia coli* maltrose-binding protein can have a profound impact on the solubility of fusion proteins," Pro Sci Mar. 2011, vol. 10, No. 3, pp. 622-630 (especially abstract).
Waugh, David S., "Making the most of affinity tags," Trends in Biotechnology, vol. 23, No. 6, Jun. 2005, pp. 316-319.
Simon, Dawn M, et al., "A diversity of uncharacterized reverse transcriptases in bacteria," Nucleic Acids Research, vol. 36, No. 22, pp. 7219-7229 (2008).
Kohima Kenji, et al., "Systematic Survey for Novel Types of Prokaryotic Retroelements based on Gene Neighborhood and Protein Architecture," Molecular Biology and Evolution, vol. 25, pp. 1395-04 (2008).
Lixin Dai et al., "Database for Mobile Group II Introns", Nucleic Acids Research, vol. 31, pp. 424-426 (2003).
Zhong, Jin et al., "Group II intron mobility using nascent strands at DNA replication forks to prime reverse transcription," EMBO Journal, vol. 22, No. 17., pp. 4555-4565, (2003).
Smith, Dorie et al., "Recruitment of host functions suggests a repair pathway for late steps in group II intron retrohoming", Genes and Development 19, 2477-2487, (2005).
Conlan, Lori H. et al., "Localization, mobility and fidelity of retrotransposed Group II introns in rRNA genes", Nucleic Acids Research, vol. 33, pp. 5262-5270 (2005).
Tatusova,Tatiana, et al., "BLAST 2 Sequences, a new tool for comparing protein and nucleotide sequences," FEMS Microbiology Letters, vol. 74, pp. 247-250 (1999).
Xiong , Yur et al., "Origin and evolution of retroelements based upon their reverse transcriptase sequences," EMBO Journal, vol. 9, No. 10, pp. 3353-3362 (1990).
Blocker, Forrest J.H et al, "Domain Structure and Three-Dimensional Model of a Group II intron-encded Reverse Transcriptase," RNA, vol. 11, pp. 14-28 (2005).
Vellore, Jaisheer et al., "A group II Intron-Type open reading frame from the thermophile bacillus (Geobacillus) stearothermophilus encodes a heat-stable reverse transcriptase," Appl. Environ. Microbiol. vol. 70, pp. 7140-7147, (2004).

(Continued)

*Primary Examiner* — Richard G Hutson
(74) *Attorney, Agent, or Firm* — Tarolli, Sundheim, Covell & Tummino LLP

(57) ABSTRACT

Stabilized reverse transcriptase fusion proteins including a thermostable reverse transcriptase connected to a stabilizer protein are described. Attaching the stabilizer protein to the thermostable reverse transcriptase stabilizes the fusion protein and can aid in its purification, provide increased solubility, allow for longer storage, or allow the fusion protein to be used under more rigorous conditions such as higher temperature. The stabilized reverse transcriptase fusion protein can also include a linker between the stabilizer protein and the thermostable reverse transcriptase. The stabilized reverse transcriptase fusion proteins are suitable for use in nucleic acid amplification methods such as the reverse transcription polymerase chain reaction and other applications involving cDNA synthesis.

16 Claims, 24 Drawing Sheets

Specification includes a Sequence Listing.

(56) References Cited

OTHER PUBLICATIONS

Ng, Bernie et al., "Reverse Transcriptase:Intron-encoded proteins found in thermophilic bacetria," Gene vol. 393, pp. 137-144, (2007).
Janin, Joel et al., "Structural Domains in Proteins and Their Role in the Dynamics of Protein Function," Progress in Biophysics and Molecular Biology, vol. 42, pp. 21-78 (1983).
Idicula, Susan et al., "Understanding the relationship between the primary structure of proteins and its propensity to be soluble on overexpression in *Escherichia coli*," Protein Science, vol. 14, pp. 582-592 (2005).
Harrison R.G., "Expression of soluble heterologous proteins via fusion with NuSA protein," inNovations, vol. 11, pp. 4-7 (2000).
Collins-Racie et al., Biotechnology, 13, p. 982-87 (1995).
Wriggers, Willey et al., "Control of Protein Functional Dynamics of Peptide Linkers," Biopolymers, vol. 80, pp. 736-746 (2005).
George, Richard A., et al., "An anlayses fo protein domain linkers: their classification and role in protein folding," Protein Engineering, vol. 15, pp. 871-879 (2003).
Saldanha, Roland et al., "RNA and protein catalysis in Group II intron splicing and mobility reactions using purified components," Biochemistry vol. 38, pp. 9069-9083, (1999).
Nallamsetty, Sreedevi et al., Solubility-enhancing proteins MBP and NusA play a passive role in the folding of their fusion partners,: Protein Expression and Purification vol. 45, pp. 175-182, (2005).
Smyth, Douglas et al., "Crystal Structure of fusion proteins with large affinity flags," Protein Science, pp. 1313-1322, (2003).
Guo Huatato, et al., "Group II Introns Designed to Insert into Therapeutically Relevant DNA Target Sites in Human Cells", Science 289, 452-457, (2000).
Karberg, Michael et al., "Group II introns as controllable gene targeting vectors for genetic manipulation of bacteria", Nature Biotechnolgy, vol. 19, pp. 1162-1167, (2001).
San Filippo, Joseph et al., "Characterization of the C-Terminal DNA-binding/DNA endonuclear region of a Group II intron-encoded protein," Journal of Molecular Biology, vol. 324, pp. 933-951, (2002).
Potter., "SuperScript III First-Strand Synthesis Supermis for qRT-PCR,". Focus (Invitrogen Newsletter) 25.1, pp. 19-24, (2003).
Chee, Gab-Joo et al., "Housekeeping RecA give interrupted by Group II intron in a thermophilic Geobacillus Kaustrophilus," Gene, vol. 363, pp. 211-220, (2005).
Kristelly, Romana et al., "Preliminary structure analysis of the DH/PH domains of leukemia-associated RhoGEF," Acta Crystallographica, Section D, Biological Crystallography, D59, 1pp. 859-1862, (2003).
Makarova, Olga et al., "Generation of Deletion and Point Mutations with One Primer in a Single Cloning Step," Inventrogen BioTechniques vol. 29, pp. 970-972, (2000).
Nominé et al., "Formation of Soluble Inclusion Bodies by HPV E6 Oncoprotein Fused to Maltose-Binding Protein" Protein Expression and Purification, vol. 23, pp. 22-32, 2001.
Ke et al., "Insignts into Binding Cooperativity of MATa1/MATα2 from the Crystal Structure of a MATa1 Homeodomain-Maltose Binding Protein Chimera" Protein Science, vol. 12 pp. 306-312, 2003.
Terpe K., "Overview of Tag Protein Fusions: From Molecular and Biochemical Fundamentals to Commercial Systems", Appl. Microbiol. Biotechnol, vol. 60, pp. 523-533, 2003.
Esposito et al., "Enhancement of Soluble Protein Expression Through the Use of Fusion Tags" Current Opinion in Biotechnology, vol. 17, pp. 353-358, 2006.
Chan et al., "Soluble Expression of Proteins correlates with a Lack of Positively-Charged Surface" Scientific Reports, pp. 1-6, 2013.
Wang et al., "Nucleic Acid-Binding Specificity of Human FUS Protein" Nucleic Acids Research, vol. 43, No. 15, pp. 7535-7543, 2015.
Search Report from European Patent Application No. 10749312.4-2403 dated Aug. 8, 2012.
Leon, Gregory, et al., "Potential Role of Group IIC-attC Introns in Integron Cassette Formation," Journal of Bacteriology, vol. 191, No. 19, Oct. 1, 2009, pp. 6040-6051.
Matsurra, Manabu, et al., "A bacterial group II intron encoding reverse transcriptase, maturase, and DNA endonuclease activities; biochemical demonstration of maturase activity and insertion of new genetic information within the?intron," Genes and Development, Cold Spring Harbor Laboratory Press, vol. 11, Nov. 1, 1997, pp. 2910-2924.
Jeong, Dae-Won, et al., "Evidence for the Complex Formation between Reverse Transcriptase and Multicopy Single-stranded DNA in Retron EC83," Molecules and Cells, vol. 7, No. 3, pp. 347-351.
Database UniProt [online], "Subname: full=reverse transcriptase," Mar. 1, 2003, retrieved from EBI accession No. UNIPORT:Q8CM00.
England, New. "pMAL™ Protein Fusion and Purification System." (1991).
Mohr, Sabine, et al. "Thermostable group II intron reverse transcriptase fusion proteins and their use in cDNA synthesis and next-generation RNA sequencing." Rna 19.7 (2013): 958-970.
European Office Action corresponding to European App. No. 10749312.4, dated Feb. 2, 2017, pp. 1-8.
Canadian Office Action corresponding to Canadian Patent Application No. 2754476, dated Jun. 1, 2017, pp. 1-7.
Chinese Office Action corresponding to Chinese Patent Application No. 20180020123.1, dated May 4, 2017, pp. 1-10.
Nakamura, Y. et al., "Reverse Transcriptse [Thermosynechococcus elongatus BP-1]," GenBank, BAC08171.1, Aug. 17, 2002.
Nakamura, Y. et al., "Reverse Transcriptse [Thermosynechococcus elongatus BP-1]," GenBank, BAC08074.1, Aug. 17, 2002.
Nakamura, Y. et al., "Reverse Transcriptse [Thermosynechococcus elongatus BP-1]," GenBank, BAC07667.1, Aug. 17, 2002.

* cited by examiner

SEQ ID NO: 6

```
  1 MKIEEGKLVI WINGDKGYNG LAEVGKKFEK DTGIKVTVEH PDKLEEKFPQ VAATGDPDI
 61 IFWAHDRFGG YAQSGLLAEI TPDKAFQDKL YPFTWDAVRY NGKLIAYPIA VEALSLIYNK
121 DLLPNPPKTW EEIPALDKEL KAKGKSALMF NLQEPYFTWP LIAADGGYAF KYENGKYDIK
181 DVGVDNAGAK AGLTFLVDLI KNKHMNADTD YSIAEAAFNK GETAMTINGP WAWSNIDTSK
241 VNYGVTVLPT FKGQPSKPFV GVLSAGINAA SPNKELAKEF LENYLLTDEG LEAVNKDKPL
301 GAVALKSYEE ELAKDPRIAA TMENAQKGEI MPNIPQMSAF WYAVRTAVIN AASGRQTVDA
361 ALAAAQTAAA AAMETRQMTV DQTTGAVTNQ TETSWHSINW TKANREVKRL QVRIAKAVKE
421 GRWGKVKALQ WLLTHSFYGK ALAVKRVTDN SGSRTPGVDG ITWSTQEQKT QAIKSLRRRG
481 YKPQPLRRVY IPKANGKQRP LGIPTMKDRA MQALYALALE PVAETTADRN SYGFRRGRCT
541 ADAAGQCFLA LAKAKSAEHV LDADISGCFD NISHEWLLAN TPLDKGILRK WLKSGFVWKQ
601 QLFPTHAGTP QGGVISPVLA NITLDGMEEL LAKHLRGQKV NLIRYADDFV VTGKDEETLE
661 KARNLIQEFL KERGLTLSPE KTKIVHIEEG FDFLGWNIRK YNGVLLIKPA KKNVKAFLKK
721 IRDTLRELRT ATQEIVIDTL NPIIRGWANY HKGQVSKETF NRVDFATWHK LWRWARRRHP
781 NKPAQWVKDK YFIKNGSRDW VFGMVMKDKN GELRTKRLIK TSDTRIQRHV KIKADANPFL
841 PEWAEYFEKR KKLKKAPAQY RRIRRELWKK QGGICPVCGG EIEQDMLTDI HHILPKHKGG
901 SDDLDNLVLI HANCHKQVHS RDGQHSRSLL KEGL*
```

FIG. 1

SEQ ID NO: 7

```
  1 MKIEEGKLVI WINGDKGYNG LAEVGKKFEK DTGIKVTVEH PDKLEEKFPQ VAATGDPDI
 61 IFWAHDRFGG YAQSGLLAEI TPDKAFQDKL YPFTWDAVRY NGKLIAYPIA VEALSLIYNK
121 DLLPNPPKTW EEIPALDKEL KAKGKSALMF NLQEPYFTWP LIAADGGYAF KYENGKYDIK
181 DVGVDNAGAK AGLTFLVDLI KNKHMNADTD YSIAEAAFNK GETAMTINGP WAWSNIDTSK
241 VNYGVTVLPT FKGQPSKPFV GVLSAGINAA SPNKELAKEF LENYLLTDEG LEAVNKDKPL
301 GAVALKSYEE ELAKDPRIAA TMENAQKGEI MPNIPQMSAF WYAVRTAVIN AASGRQTVDA
361 ALAAAQTAAA AAMETRQMAV EQTTGAVTNQ TETSWHSIDW AKANREVKRL QVRIAKAVKE
421 GRWGKVKALQ WLLTHSFYGK ALAVKRVTDN SGSKTPGVDG ITWSTQEQKA QAIKSLRRRG
481 YKPQPLRRVY IPKANGKQRP LGIPTMKDRA MQALYALALE PVAETTADRN SYGFRRGRCI
541 ADAATQCHIT LAKTDRAQYV LDADIAGCFD NISHEWLLAN IPLDKRILRK WLKSGFVWKQ
601 QLFPIHAGTP QGGVISPMLA NMTLDGMEEL LNKFPRAHKV KLIRYADDFV VTGETKEVLY
661 IAGAVIQAFL KERGLTLSKE KTKIVHIEEG FDFLGWNIRK YDGKLLIKPA KKNVKAFLKK
721 IRDTLRELRT APQEIVIDTL NPIIRGWTNY HKNQASKETF VGVDHLIWQK LWRWARRRHP
781 SKSVRWVKSK YFIQIGNRKW MFGIWTKDKN GDPWAKHLIK ASEIRIQRRG KIKADANPFL
841 PEWAEYFEQR KKLKEAPAQY RRTRRELWKK QGGICPVCGG EIEQDMLTEI HHILPKHKGG
901 TDDLDNLVLI HTNCHKQVHN RDGQHSRFLL KEGL*
```

FIG. 2

SEQ ID NO: 8

```
  1 MKIEEGKLVI WINGDKGYNG LAEVGKKFEK DTGIKVTVEH PDKLEEKFPQ VAATGDGPDI
 61 IFWAHDRFGG YAQSGLLAEI TPDKAFQDKL YPFTWDAVRY NGKLIAYPIA VEALSLIYNK
121 DLLPNPPKTW EEIPALDKEL KAKGKSALMF NLQEPYFTWP LIAADGGYAF KYENGKYDIK
181 DVGVDNAGAK AGLTFLVDLI KNKHMNADTD YSIAEAAFNK GETAMTINGP WAWSNIDTSK
241 VNYGVTVLPT FKGQPSKPFV GVLSAGINAA SPNKELAKEF LENYLLTDEG LEAVNKDKPL
301 GAVALKSYEE ELAKDPRIAA TMENAQKGEI MPNIPQMSAF WYAVRTAVIN AASGRQTVDA
361 ALAAAQTAAA AAMETRQMAV EQTTGAVTNQ TETSWHSIDW AKANREVKRL QVRIAKAVKE
421 GRWGKVKALQ WLLTHSFYGK ALAVKRVTDN SGSKTPGVDG ITWSTQEQKA QAIKSLRRRG
481 YKPQPLRRVY IPKASGKQRP LGIPTTKDRA MQALYALALE PVAETTADRN SYGFRQGRCT
541 ADAAGQCFTV LGRSDCAKYI LDADITGCFD NISHEWLLDN IPLDKEVLRK WLKSGFVWKQ
601 QLFPTHAGTP QGGVISPMLA NMTLDGMEEL LKKHLRKQKV NLIRYADDFV VTGESKETLE
661 KVTTVIQEFL KERGLTLSEE KTKVVHIEEG FDFLGWNIRK YGEKLLIKPA KKNIKAFHKK
721 IRDALKELRT ATQEAVIDTL NPIIKGWANY HRNQVSKRIF NRADDNIWHK LWRWAKRRHP
781 NKPARWTKNK YFIKIGNRHW VFGTWKKDKE GRLRSRYLIK AGDTRIQRHV KIKADANPFL
841 PEWAEYFEER KKLKEAPAQY RRIRRELWKK QGGICPVCGG EIEQDMLTEI HHILPKHKGG
901 SDDLDNLVLI HANCHKQVHS RDGQHSRFLL KEGL*
```

FIG. 3

SEQ ID NO: 9

```
  1 MKIEEGKLVI WINGDKGYNG LAEVGKKFEK DTGIKVTVEH PDKLEEKFPQ VAATGDGPDI
 61 IFWAHDRFGG YAQSGLLAEI TPDKAFQDKL YPFTWDAVRY NGKLIAYPIA VEALSLIYNK
121 DLLPNPPKTW EEIPALDKEL KAKGKSALMF NLQEPYFTWP LIAADGGYAF KYENGKYDIK
181 DVGVDNAGAK AGLTFLVDLI KNKHMNADTD YSIAEAAFNK GETAMTINGP WAWSNIDTSK
241 VNYGVTVLPT FKGQPSKPFV GVLSAGINAA SPNKELAKEF LENYLLTDEG LEAVNKDKPL
301 GAVALKSYEE ELAKDPRIAA TMENAQKGEI MPNIPQMSAF WYAVRTAVIN AASGRQTVDA
361 ALAAAQTAAA AAMKVNKLVV KSEQDLRNCL DLLYQEAKKG KHFYGMLELL QNDVVILEAI
421 RNIKSNKGSK TAGIDQKIVD DYLLMPTEKV FGMIKAKLND YKPIPVRRCN KPKGNAKSSK
481 RKGNSPNEEG ETRPLGISAV TDRIIQEMLR IVLEPIFEAQ FYPHSYGFRP YRSTEHALAW
541 MLKIINGSKL YWVVKGDIES YFDHINHKKL LNIMWNMGVR DKRVLCIVKK MLKAGQVIQG
601 KFYPTAKGIP QGGIISPLLA NVYLNSFDWM VGQEYEYHPN NANYREKKNA LAALRNKGHH
661 PVFYIRYADD WVILTDTKEY AEKIREQCKQ YLACELHLTL SDEKTFIADI REQRVKFLGF
721 CIEAGKRRFH KKGFAARMIP DMEKVNAKVK EIKRDIRLLR TRKSELEKAL DIENINTKII
781 GLANHLKIGI SKYIMGKVDR VIEETAYRTW VKMYGKEKAA QYKRPVSEFH NRIDRHKGYQ
841 MKHFSVVTED GIRVGITHAK ITPIQYATVF KQEMTPYTAD GRKMYEEKHR KIRLPDKMSL
901 FDHDSIFIYI LSEHNDGKYN LEYFLNRVNV FHRDKGKCKI CAVYLSPGNF HCHHIDPSKP
961 LSEINKTVNL ISLCNQCHRL VHSNQEPPFT ERKMFDKLTK YRNKLKI*
```

FIG. 4

SEQ ID NO: 10

```
  1 MKIEEGKLVI WINGDKGYNG LAEVGKKFEK DTGIKVTVEH PDKLEEKFPQ VAATGDGPDI
 61 IFWAHDRFGG YAQSGLLAEI TPDKAFQDKL YPFTWDAVRY NGKLIAYPIA VEALSLIYNK
121 DLLPNPPKTW EEIPALDKEL KAKGKSALMF NLQEPYFTWP LIAADGGYAF KYENGKYDIK
181 DVGVDNAGAK AGLTFLVDLI KNKHMNADTD YSIAEAAFNK GETAMTINGP WAWSNIDTSK
241 VNYGVTVLPT FKGQPSKPFV GVLSAGINAA SPNKELAKEF LENYLLTDEG LEAVNKDKPL
301 GAVALKSYEE ELAKDPRIAA TMENAQKGEI MPNIPQMSAF WYAVRTAVIN AASGRQTVDA
361 ALAAAQTAAA AAMALLERIL ARDNLITALK RVEANQGAPG IDGVSTDQLR DYIRAHWSTI
421 HAQLLAGTYR PAPVRRVEIP KPGGGTRQLG IPTVVDRLIQ QAILQELTPI FDPDFSSSSF
481 GFRPGRNAHD AVRQAQGYIQ EGYRYVVDMD LEKFFDRVNH DILMSRVARK VKDKRVLKLI
541 RAYLQAGVMI EGVKVQTEEG TPQGGPLSPL LANILLDDLD KELEKRGLKF CRYADDCNIY
601 VKSLRAGQRV KQSIQRFLEK TLKLKVNEEK SAVDRPWKRA FLGFSFTPER KARIRLAPRS
661 IQRLKQRIRQ LTNPNWSISM PERIHRVNQY VMGWIGYFRL VETPSVLQTI EGWIRRRLRL
721 CQWLQWKRVR TRIRELRALG LKETAVMEIA NTRKGAWRTT KTPQLHQALG KTYWTAQGLK
781 SLTQRYFELR QG*
```

FIG. 5

SEQ ID NO: 13

```
   1 CCGACACCAT CGAATGGTGC AAAACCTTTC GCGGTATGGC ATGATAGCGC CCGGAAGAGA
  61 GTCAATTCAG GGTGGTGAAT GTGAAACCAG TAACGTTATA CGATGTCGCA GAGTATGCCG
 121 GTGTCTCTTA TCAGACCGTT TCCCGCGTGG TGAACCAGGC CAGCCACGTT TCTGCGAAAA
 181 CGCGGGAAAA AGTGGAAGCG GCGATGGCGG AGCTGAATTA CATTCCCAAC CGCGTGGCAC
 241 AACAACTGGC GGGCAAACAG TCGTTGCTGA TTGGCGTTGC CACCTCCAGT CTGGCCCTGC
 301 ACGCGCCGTC GCAAATTGTC GCGGCGATTA AATCTCGCGC CGATCAACTG GGTGCCAGCG
 361 TGGTGGTGTC GATGGTAGAA CGAAGCGGCG TCGAAGCCTG TAAAGCGGCG GTGCACAATC
 421 TTCTCGCGCA ACGCGTCAGT GGGCTGATCA TTAACTATCC GCTGGATGAC CAGGATGCCA
 481 TTGCTGTGGA AGCTGCCTGC ACTAATGTTC CGGCGTTATT TCTTGATGTC TCTGACCAGA
 541 CACCCATCAA CAGTATTATT TTCTCCCATG AAGACGGTAC GCGACTGGGC GTGGAGCATC
 601 TGGTCGCATT GGGTCACCAG CAAATCGCGC TGTTAGCGGG CCCATTAAGT TCTGTCTCGG
 661 CGCGTCTGCG TCTGGCTGGC TGGCATAAAT ATCTCACTCG CAATCAAATT CAGCCGATAG
 721 CGGAACGGGA AGGCGACTGG AGTGCCATGT CCGGTTTTCA ACAAACCATG CAAATGCTGA
 781 ATGAGGGCAT CGTTCCCACT GCGATGCTGG TTGCCAACGA TCAGATGGCG CTGGGCGCAA
 841 TGCGCGCCAT TACCGAGTCC GGGCTGCGCG TTGGTGCGGA TATCTCGGTA GTGGGATACG
 901 ACGATACCGA AGACAGCTCA TGTTATATCC CGCCGTTAAC CACCATCAAA CAGGATTTTC
 961 GCCTGCTGGG GCAAACCAGC GTGGACGCT TGCTGCAACT CTCTCAGGGC CAGGCGGTGA
1021 AGGGCAATCA GCTGTTGCCC GTCTCACTGG TGAAAGAAA AACCACCCTG GCGCCCAATA
1081 CGCAAACCGC CTCTCCCCGC GCGTTGGCCG ATTCATTAAT GCAGCTGGCA CGACAGGTTT
1141 CCCGACTGGA AAGCGGGCAG TGAGCGCAAC GCAATTAATG TAAGTTAGCT CACTCATTAG
1201 GCACAATTCT CATGTTTGAC AGCTTATCAT CGACTGCACG GTGCACCAAT GCTTCTGGCG
1261 TCAGGCAGCC ATCGGAAGCT GTGGTATGGC TGTGCAGGTC GTAAATCACT GCATAATTCG
1321 TGTCGCTCAA GGCGCACTCC CGTTCTGGAT AATGTTTTTT GCGCCGACAT CATAACGGTT
1381 CTGGCAAATA TTCTGAAATG AGCTGTTGAC AATTAATCAT CGGCTCGTAT AATGTGTGGA
1441 ATTGTGAGCG GATAACAATT TCACACAGGA AACAGCCAGT CCGTTTAGGG GTTTTCACGA
1501 GCACTTCACC AACAAGGACC ATAGCATATG AAAATCGAAG AAGGTAAACT GGTAATCTGG
1561 ATTAACGGCG ATAAAGGCTA TAACGGTCTC GCTGAAGTCG GTAAGAAATT CGAGAAAGAT
1621 ACCGGAATTA AAGTCACCGT TGAGCATCCG GATAAACTGG AAGAGAAATT CCCACAGGTT
1681 GCGGCAACTG GCGATGGCCC TGACATTATC TTCTGGGCAC ACGACCGCTT TGGTGGCTAC
1741 GCTCAATCTG GCCTGTTGGC TGAAATCACC CCGGACAAAG CGTTCCAGGA CAAGCTGTAT
1801 CCGTTTACCT GGGATGCCGT ACGTTACAAC GGCAAGCTGA TTGCTTACCC GATCGCTGTT
1861 GAAGCGTTAT CGCTGATTTA TAACAAAGAT CTGCTGCCGA ACCCGCCAAA AACCTGGGAA
1921 GAGATCCCGG CGCTGGATAA AGAACTGAAA GCGAAGGTA AGAGCGCGCT GATGTTCAAC
1981 CTGCAAGAAC CGTACTTCAC CTGGCCGCTG ATTGCTGCTG ACGGGGGTTA TGCGTTCAAG
2041 TATGAAAACG GCAAGTACGA CATTAAAGAC GTGGGCGTGG ATAACGCTGG CGCGAAAGCG
2101 GGTCTGACCT TCCTGGTTGA CCTGATTAAA AACAAACACA TGAATGCAGA CACCGATTAC
2161 TCCATCGCAG AAGCTGCCTT TAATAAAGGC GAAACAGCGA TGACCATCAA CGGCCCGTGG
2221 GCATGGTCCA ACATCGACAC CAGCAAAGTG AATTATGGTG TAACGGTACT GCCGACCTTC
2281 AAGGGTCAAC CATCCAAACC GTTCGTTGGC GTGCTGAGCG CAGGTATTAA CGCCGCCAGT
2341 CCGAACAAAG AGCTGGCAAA AGAGTTCCTC GAAAACTATC TGCTGACTGA TGAAGGTCTG
2401 GAAGCGGTTA ATAAAGACAA ACCGCTGGGT GCCGTAGCGC TGAAGTCTTA CGAGGAAGAG
2461 TTGGCGAAAG ATCCACGTAT TGCCGCCACT ATGGAAAACG CCCAGAAAGG TGAAATCATG
2521 CCGAACATCC CGCAGATGTC CGCTTTCTGG TATGCCGTGC GTACTGCGGT GATCAACGCC
2581 GCCAGCGGTC GTCAGACTGT CGATGCCGCC CTGGCCGCCG CGCAGACTGC CGCCGCCGCC
2641 GCCATGGAGA CAAGGCAAAT GACGGTGGAC CAAACCACTG GTGCGGTCAC CAACCAAACG
2701 GAAACAAGCT GGCACAGCAT AAACTGGACC AAAGCCAACC GTGAGGTAAA GAGGCTGCAA
2761 GTGCGTATCG CAAAGGCTGT GAAGGAAGGA CGCTGGGGCA AAGTGAAAGC TTTGCAATGG
2821 CTCCTGACCC ACTCGTTCTA CGGCAAAGCC CTCGCCGTGA ACGGGTAAC TGACAACTCA
2881 GGCAGTAGAA CACCTGGTGT GGACGGGATA ACCTGGTCCA CACAAGAGCA GAAAACCCAA
2941 GCCATAAAGT CCCTCAGGAG AAGAGGCTAT AAACCCCAAC CCCTGAGGCG GGTATACATC
3001 CCGAAAGCAA ACGGCAAACA GCGCCCGCTA GGAATCCCGA CAATGAAGGA CAGGGCAATG
3061 CAGGCACTAT ATGCCCTAGC CCTAGAACCA GTCGCGGAAA CCACAGCGGA CCGGAACTCC
3121 TATGGGTTCC GCCGAGGGCG ATGTACGGCA GATGCGGCAG GACAATGCTT CCTTGCTCTG
3181 GCAAAGCCA AGTCGGCTGA ACACGTCCTT GACGCTGACA TATCCGGATG CTTTGATAAC
3241 ATCAGCCATG AGTGGCTACT AGCCAACACT CCACTGGACA AAGGGATCTT ACGGAAATGG
3301 CTTAAATCTG GGTTCGTCTG GAAACAGCAA CTCTTCCCCA CCCATGCTGG GACACCTCAG
3361 GGAGGGGTAA TCTCCCCAGT TCTTGCCAAT ATAACCCTAG ATGGGATGGA AGAACTGTTG
3421 GCCAAACACC TCAGAGGTCA AAAGTCAAC CTCATCCGAT ATGCTGACGA TTTTGTCGTG
3481 ACGGGAAAAG ATGAGGAAAC CCTGAGAAA GCCAGAAACC TAATCCAGGA GTTCCTAAAA
```

FIG. 6

```
3541 GAACGGGGCT TGACCCTGTC CCCCGAGAAG ACAAAAATCG TCCATATTGA GGAAGGCTTC
3601 GACTTTCTCG GATGGAACAT TCGCAAGTAC AACGGGGTTC TTCTCATCAA ACCCGCGAAG
3661 AAGAACGTGA AAGCGTTCCT CAAGAAAATC CGAGACACTC TAAGGGAACT TAGGACAGCA
3721 ACCCAGGAAA TCGTGATAGA CACACTCAAC CCAATCATTA GAGGTTGGGC CAACTATCAC
3781 AAAGGACAAG TCTCTAAGGA AACCTTCAAC CGAGTGGACT TCGCCACCTG GCACAAATTG
3841 TGGCGATGGG CAAGGCGCCG GCACCCAAAC AAACCTGCCC AATGGGTGAA GGACAAATAC
3901 TTCATCAAAA ACGGAAGCAG AGACTGGGTG TTCGGTATGG TGATGAAAGA CAAGAACGGG
3961 GAACTGAGGA CCAAACGCCT AATCAAAACC TCTGACACCC GAATCCAACG CCACGTCAAA
4021 ATCAAGGCAG ACGCCAATCC GTTTCTCCCA GAGTGGGCAG AATACTTTGA GAAACGCAAG
4081 AAACTCAAAA AAGCCCCTGC TCAATATCGG CGCATCCGCC GAGAACTATG AAGAAACAG
4141 GGTGGTATCT GTCCAGTATG CGGGGGTGAA ATTGAGCAAG ACATGCTCAC TGACATCCAC
4201 CACATATTGC CCAAACACAA GGGTGGTTCT GACGACCTGG ATAATCTTGT CTTAATCCAC
4261 GCCAACTGCC ACAAACAGGT GCACAGCCGA GATGGTCAGC ACAGCCGGTC CCTCTTGAAA
4321 GAGGGGCTTT GACTGCAGGC AAGCTTGGCA CTGGCCGTCG TTTTACAACG TCGTGACTGG
4381 GAAAACCCTG GCGTTACCCA ACTTAATCGC CTTGCAGCAC ATCCCCTTT CGCCAGCTGG
4441 CGTAATAGCG AAGAGGCCCG CACCGATCGC CCTTCCCAAC AGTTGCGCAG CCTGAATGGC
4501 GAATGGCAGC TTGGCTGTTT TGGCGGATGA GATAAGATTT TCAGCCTGAT ACAGATTAAA
4561 TCAGAACGCA GAAGCGGTCT GATAAACAG AATTTGCCTG GCGGCAGTAG CGCGGTGGTC
4621 CCACCTGACC CCATGCCGAA CTCAGAAGTG AAACGCCGTA GCGCCGATGG TAGTGTGGGG
4681 TCTCCCCATG CGAGAGTAGG GAACTGCCAG GCATCAAATA AAACGAAAGG CTCAGTCGAA
4741 AGACTGGGCC TTTCGTTTTA TCTGTTGTTT GTCGGTGAAC GCTCTCCTGA GTAGGACAAA
4801 TCCGCCGGGA GCGGATTTGA ACGTTGCGAA GCAACGGCCC GGAGGGTGGC GGGCAGGACG
4861 CCCGCCATAA ACTGCCAGGC ATCAAATTAA GCAGAAGGCC ATCCTGACGG ATGGCCTTTT
4921 TGCGTTTCTA CAAACTCTTT TTGTTTATTT TTCTAAATAC ATTCAAATAT GTATCCGCTC
4981 ATGAGACAAT AACCCTGATA AATGCTTCAA TAATATTGAA AAAGGAAGAG TATGAGTATT
5041 CAACATTTCC GTGTCGCCCT TATTCCCTTT TTTGCGGCAT TTTGCCTTCC TGTTTTTGCT
5101 CACCCAGAAA CGCTGGTGAA AGTAAAAGAT GCTGAAGATC AGTTGGGTGC ACGAGTGGGT
5161 TACATCGAAC TGGATCTCAA CAGCGGTAAG ATCCTTGAGA GTTTTCGCCC CGAAGAACGT
5221 TCTCCAATGA TGAGCACTTT TAAAGTTCTG CTATGTGGCG CGGTATTATC CCGTGTTGAC
5281 GCCGGGCAAG AGCAACTCGG TCGCCGCATA CACTATTCTC AGAATGACTT GGTTGAGTAC
5341 TCACCAGTCA CAGAAAAGCA TCTTACGGAT GGCATGACAG TAAGAGAATT ATGCAGTGCT
5401 GCCATAACCA TGAGTGATAA CACTGCGGCC AACTTACTTC TGACAACGAT CGGAGGACCG
5461 AAGGAGCTAA CCGCTTTTTT GCACAACATG GGGGATCATG TAACTCGCCT TGATCGTTGG
5521 GAACCGGAGC TGAATGAAGC CATACCAAAC GACGAGCGTG ACACCACGAT GCCTGTAGCA
5581 ATGGCAACAA CGTTGCGCAA ACTATTAACT GGCGAACTAC TTACTCTAGC TTCCCGGCAA
5641 CAATTAATAG ACTGGATGGA GGCGGATAAA GTTGCAGGAC CACTTCTGCG CTCGGCCCTT
5701 CCGGCTGGCT GGTTTATTGC TGATAAATCT GGAGCCGGTG AGCGTGGGTC TCGCGGTATC
5761 ATTGCAGCAC TGGGGCCAGA TGGTAAGCCC TCCCGTATCG TAGTTATCTA CACGACGGGG
5821 AGTCAGGCAA CTATGGATGA ACGAAATAGA CAGATCGCTG AGATAGGTGC CTCACTGATT
5881 AAGCATTGGT AACTGTCAGA CCAAGTTTAC TCATATATAC TTTAGATTGA TTTACCCCGG
5941 TTGATAATCA GAAAAGCCCC AAAAACAGGA AGATTGTATA AGCAAATATT TAAATTGTAA
6001 ACGTTAATAT TTTGTTAAAA TTCGCGTTAA ATTTTTGTTA AATCAGCTCA TTTTTTAACC
6061 AATAGGCCGA AATCGGCAAA ATCCCTTATA AATCAAAAGA ATAGACCGAG ATAGGGTTGA
6121 GTGTTGTTCC AGTTTGGAAC AAGAGTCCAC TATTAAAGAA CGTGGACTCC AACGTCAAAG
6181 GGCGAAAAAC CGTCTATCAG GGCGATGGCC CACTACGTGA ACCATCACCC AAATCAAGTT
6241 TTTTGGGGTC GAGGTGCCGT AAAGCACTAA ATCGGAACCC TAAAGGGAGC CCCCGATTTA
6301 GAGCTTGACG GGGAAAGCCG GCGAACGTGG CGAGAAAGGA AGGGAAGAAA GCGAAAGGAG
6361 CGGGCGCTAG GGCGCTGGCA AGTGTAGCGG TCACGCTGCG CGTAACCACC ACACCCGCCG
6421 CGCTTAATGC GCCGCTACAG GGCGCGTAAA AGGATCTAGG TGAAGATCCT TTTTGATAAT
6481 CTCATGACCA AAATCCCTTA ACGTGAGTTT TCGTTCCACT GAGCGTCAGA CCCCGTAGAA
6541 AAGATCAAAG GATCTTCTTG AGATCCTTTT TTTCTGCGCG TAATCTGCTG CTTGCAAACA
6601 AAAAACCAC CGCTACCAGC GGTGGTTTGT TTGCCGGATC AAGAGCTACC AACTCTTTTT
6661 CCGAAGGTAA CTGGCTTCAG CAGAGCGCAG ATACCAAATA CTGTCCTTCT AGTGTAGCCG
6721 TAGTTAGGCC ACCACTTCAA GAACTCTGTA GCACCGCCTA CATACCTCGC TCTGCTAATC
6781 CTGTTACCAG TGGCTGCTGC CAGTGGCGAT AAGTCGTGTC TTACCGGGTT GGACTCAAGA
6841 CGATAGTTAC CGGATAAGGC GCAGCGGTCG GCTGAACGG GGGGTTCGTG CACACAGCCC
6901 AGCTTGGAGC GAACGACCTA CACCGAACTG AGATACCTAC AGCGTGAGCT ATGAGAAAGC
6961 GCCACGCTTC CCGAAGGGAG AAAGGCGGAC AGGTATCCGG TAAGCGGCAG GGTCGGAACA
7021 GGAGAGCGCA CGAGGGAGCT TCCAGGGGGA AACGCCTGGT ATCTTTATAG TCCTGTCGGG
7081 TTTCGCCACC TCTGACTTGA GCGTCGATTT TTGTGATGCT CGTCAGGGGG GCGGAGCCTA
7141 TGGAAAAACG CCAGCAACGC GGCCTTTTTA CGGTTCCTGG CCTTTTGCTG GCCTTTTGCT
```

```
7201 CACATGTTCT TTCCTGCGTT ATCCCCTGAT TCTGTGGATA ACCGTATTAC CGCCTTTGAG
7261 TGAGCTGATA CCGCTCGCCG CAGCCGAACG ACCGAGCGCA GCGAGTCAGT GAGCGAGGAA
7321 GCGGAAGAGC GCCTGATGCG GTATTTTCTC CTTACGCATC TGTGCGGTAT TTCACACCGC
7381 ATATATGGTG CACTCTCAGT ACAATCTGCT CTGATGCCGC ATAGTTAAGC CAGTATACAC
7441 TCCGCTATCG CTACGTGACT GGGTCATGGC TGCGCCCCGA CACCCGCCAA CACCCGCTGA
7501 CGCGCCCTGA CGGGCTTGTC TGCTCCCGGC ATCCGCTTAC AGACAAGCTG TGACCGTCTC
7561 CGGGAGCTGC ATGTGTCAGA GGTTTTCACC GTCATCACCG AAACGCGCGA GGCAGCTGCG
7621 GTAAAGCTCA TCAGCGTGGT CGTGCAGCGA TTCACAGATG TCTGCCTGTT CATCCGCGTC
7681 CAGCTCGTTG AGTTTCTCCA GAAGCGTTAA TGTCTGGCTT CTGATAAAGC GGGCCATGTT
7741 AAGGGCGGTT TTTTCCTGTT TGGTCACTGA TGCCTCCGTG TAAGGGGGAT TTCTGTTCAT
7801 GGGGGTAATG ATACCGATGA AACGAGAGAG GATGCTCACG ATACGGGTTA CTGATGATGA
7861 ACATGCCCGG TTACTGGAAC GTTGTGAGGG TAAACAACTG GCGGTATGGA TGCGGCGGGA
7921 CCAGAGAAAA ATCACTCAGG GTCAATGCCA GCGCTTCGTT AATACAGATG TAGGTGTTCC
7981 ACAGGGTAGC CAGCAGCATC CTGCGATGCA GATCCGGAAC ATAATGGTGC AGGGCGCTGA
8041 CTTCCGCGTT TCCAGACTTT ACGAAACACG GAAACCGAAG ACCATTCATG TTGTTGCTCA
8101 GGTCGCAGAC GTTTTGCAGC AGCAGTCGCT TCACGTTCGC TCGCGTATCG GTGATTCATT
8161 CTGCTAACCA GTAAGGCAAC CCCGCCAGCC TAGCCGGGTC CTCAACGACA GGAGCACGAT
8221 CATGCGCACC CGTGGCCAGG ACCCAACGCT GCCCGAAATT
```

FIG. 6 (cont.)

SEQ ID NO: 14

```
   1 CCGACACCAT CGAATGGTGC AAAACCTTTC GCGGTATGGC ATGATAGCGC CCGGAAGAGA
  61 GTCAATTCAG GGTGGTGAAT GTGAAACCAG TAACGTTATA CGATGTCGCA GAGTATGCCG
 121 GTGTCTCTTA TCAGACCGTT TCCCGCGTGG TGAACCAGGC CAGCCACGTT TCTGCGAAAA
 181 CGCGGGAAAA AGTGGAAGCG GCGATGGCGG AGCTGAATTA CATTCCCAAC CGCGTGGCAC
 241 AACAACTGGC GGGCAAACAG TCGTTGCTGA TTGGCGTTGC CACCTCCAGT CTGGCCCTGC
 301 ACGCGCCGTC GCAAATTGTC GCGGCGATTA AATCTCGCGC CGATCAACTG GGTGCCAGCG
 361 TGGTGGTGTC GATGGTAGAA CGAAGCGGCG TCGAAGCCTG TAAAGCGGCG GTGCACAATC
 421 TTCTCGCGCA ACGCGTCAGT GGGCTGATCA TTAACTATCC GCTGGATGAC CAGGATGCCA
 481 TTGCTGTGGA AGCTGCCTGC ACTAATGTTC CGGCGTTATT TCTTGATGTC TCTGACCAGA
 541 CACCCATCAA CAGTATTATT TTCTCCCATG AAGACGGTAC GCGACTGGGC GTGGAGCATC
 601 TGGTCGCATT GGGTCACCAG CAAATCGCGC TGTTAGCGGG CCCATTAAGT TCTGTCTCGG
 661 CGCGTCTGCG TCTGGCTGGC TGGCATAAAT ATCTCACTCG CAATCAAATT CAGCCGATAG
 721 CGGAACGGGA AGGCGACTGG AGTGCCATGT CCGGTTTTCA ACAAACCATG CAAATGCTGA
 781 ATGAGGGCAT CGTTCCCACT GCGATGCTGG TTGCCAACGA TCAGATGGCG CTGGGCGCAA
 841 TGCGCGCCAT TACCGAGTCC GGGCTGCGCG TTGGTGCGGA TATCTCGGTA GTGGGATACG
 901 ACGATACCGA AGACAGCTCA TGTTATATCC CGCCGTTAAC CACCATCAAA CAGGATTTTC
 961 GCCTGCTGGG GCAAACCAGC GTGGACCGCT TGCTGCAACT CTCTCAGGGC CAGGCGGTGA
1021 AGGGCAATCA GCTGTTGCCC GTCTCACTGG TGAAAGAAA AACCACCCTG GCGCCCAATA
1081 CGCAAACCGC CTCTCCCCGC GCGTTGGCCG ATTCATTAAT GCAGCTGGCA CGACAGGTTT
1141 CCCGACTGGA AAGCGGGCAG TGAGCGCAAC GCAATTAATG TAAGTTAGCT CACTCATTAG
1201 GCACAATTCT CATGTTTGAC AGCTTATCAT CGACTGCACG GTGCACCAAT GCTTCTGGCG
1261 TCAGGCAGCC ATCGGAAGCT GTGGTATGGC TGTGCAGGTC GTAAATCACT GCATAATTCG
1321 TGTCGCTCAA GGCGCACTCC CGTTCTGGAT AATGTTTTTT GCGCCGACAT CATAACGGTT
1381 CTGGCAAATA TTCTGAAATG AGCTGTTGAC AATTAATCAT CGGCTCGTAT AATGTGTGGA
1441 ATTGTGAGCG GATAACAATT TCACACAGGA ACAGCCAGT CCGTTTAGGT GTTTTCACGA
1501 GCACTTCACC AACAAGGACC ATAGCATATG AAAATCGAAG AAGGTAAACT GGTAATCTGG
1561 ATTAACGGCG ATAAAGGCTA TAACGGTCTC GCTGAAGTCG GTAAGAAATT CGAGAAAGAT
1621 ACCGGAATTA AAGTCACCGT TGAGCATCCG GATAAACTGG AAGAGAAATT CCCACAGGTT
1681 GCGGCAACTG GCGATGGCCC TGACATTATC TTCTGGGCAC ACGACCGCTT GGTGGCTAC
1741 GCTCAATCTG GCCTGTTGGC TGAAATCACC CCGGACAAAG CGTTCCAGGA CAAGCTGTAT
1801 CCGTTTACCT GGGATGCCGT ACGTTACAAC GGCAAGCTGA TTGCTTACCC GATCGCTGTT
1861 GAAGCGTTAT CGCTGATTTA TAACAAAGAT CTGCTGCCGA ACCCGCCAAA AACCTGGGAA
1921 GAGATCCCGG CGCTGGATAA AGAACTGAAA GCGAAGGTA AGAGCGCGCT GATGTTCAAC
1981 CTGCAAGAAC CGTACTTCAC CTGGCCGCTG ATTGCTGCTG ACGGGGGTTA TGCGTTCAAG
2041 TATGAAAACG GCAAGTACGA CATTAAAGAC GTGGGCGTGG ATAACGCTGG CGCGAAAGCG
2101 GGTCTGACCT TCCTGGTTGA CCTGATTAAA AACAAACACA TGAATGCAGA CACCGATTAC
2161 TCCATCGCAG AAGCTGCCTT TAATAAAGGC GAAACAGCGA TGACCATCAA CGGCCCGTGG
2221 GCATGGTCCA ACATCGACAC CAGCAAAGTG AATTATGGTG TAACGGTACT GCCGACCTTC
2281 AAGGGTCAAC CATCCAAACC GTTCGTTGGC GTGCTGAGCG CAGGTATTAA CGCCGCCAGT
2341 CCGAACAAAG AGCTGGCAAA AGAGTTCCTC GAAAACTATC TGCTGACTGA TGAAGGTCTG
2401 GAAGCGGTTA ATAAAGACAA ACCGCTGGGT GCCGTAGCGC TGAAGTCTTA CGAGGAAGAG
2461 TTGGCGAAAG ATCCACGTAT TGCCGCCACT ATGGAAAACG CCCAGAAAGG TGAAATCATG
2521 CCGAACATCC CGCAGATGTC CGCTTTCTGG TATGCCGTGC GTACTGCGGT GATCAACGCC
2581 GCCAGCGGTC GTCAGACTGT CGATGCCGCC TGGCCGCCG CGCAGACTGC CGCCGCCGCC
2641 GCCATGGAGA CAAGGCAAAT GGCAGTGGAA CAAACCACTG GTGCGGTCAC CAACCAAACG
2701 GAAACAAGCT GGCACAGCAT AGACTGGGCC AAAGCCAACC GTGAGGTAAA GAGGCTGCAA
2761 GTGCGTATCG CAAAGGCTGT GAAGGAAGGA CGCTGGGGCA AAGTGAAAGC TTTGCAATGG
2821 CTCCTGACCC ACTCGTTCTA CGGCAAAGCC CTCGCCGTGA ACGGGTAAC TGACAACTCG
2881 GGCAGCAAAA CACCTGGTGT GGACGGGATA ACCTGGTCCA CACAAGAGCA GAAAGCCCAA
2941 GCCATAAAGT CCCTCAGGAG AAGAGCTAT AAACCCCAAC CCCTGAGGCG GGTATACATC
3001 CCGAAAGCAA ACGGCAAACA GCGCCCGCTA GGAATCCCGA CAATGAAGGA CAGGGCAATG
3061 CAGGCACTAT ATGCCCTAGC CCTAGAACCA GTCGCGGAAA CCACAGCAGA CCGGAACTCC
3121 TATGGGTTCC GGCGAGGACG ATGCATAGCC GATGCAGCGA CGCAGTGTCA CATCACGCTA
3181 GCCAAAACAG ACCGTGCACA ATACGTTCTC GACGCCGATA TTGCTGGGTG CTTTGACAAC
3241 ATCAGCCATG AGTGGCTACT AGCTAACATT CCACTAGACA AAAGAATTCT ACGGAAATGG
3301 CTTAAATCTG GGTTTGTCTG GAAGCAGCAA CTCTTCCCCA TCCATGCTGG AACACCTCAG
3361 GGAGGGGTAA TCTCCCCGAT GCTTGCCAAC ATGACACTGG ATGGGATGGA AGAATTGTTA
3421 AACAAGTTTC CAGGGCGCA CAAGGTCAAA CTCATCCGAT ATGCCGACGA CTTCGTCGTA
3481 ACCGGTGAAA CGAAGGAAGT GCTCTATATT GCCGGTGCGG TAATACAAGC ATTCCTCAAG
```

FIG. 7

```
3541 GAAAGGGGCC TTACCCTATC AAAGGAAAAG ACGAAGATCG TACACATTGA AGAAGGGTTT
3601 GACTTTCTCG GATGGAACAT TCGCAAATAT GATGGGAAAC TGCTCATCAA ACCTGCGAAG
3661 AAGAACGTTA AAGCGTTCCT CAAGAAAATC CGAGACACCT TAAGAGAACT TAGGACAGCA
3721 CCCCAGGAGA TTGTGATAGA CACACTCAAC CCAATCATCA GAGGTTGGAC TAACTATCAC
3781 AAAAATCAGG CATCCAAAGA AACCTTCGTC GGAGTGGACC ACCTCATATG GCAAAAATTA
3841 TGGCGATGGG CAAGGCGCCG ACACCCAAGC AAATCTGTCC GATGGGTGAA GAGTAAGTAC
3901 TTCATCCAAA TCGGGAACAG AAAATGGATG TTCGGAATAT GGACGAAAGA CAAAAACGGA
3961 GACCCGTGGG CCAAGCATTT AATCAAAGCC TCGGAAATCC GAATCCAACG TCGCGGTAAA
4021 ATCAAGGCAG ACGCCAACCC GTTTCTCCCA GAATGGGCAG AATACTTTGA GCAGCGCAAG
4081 AAACTCAAAG AGGCCCCTGC CCAATACCGG CGCACCCGTC GGGAATTGTG AAGAAACAA
4141 GGCGGCATCT GTCCAGTATG TGGGGGAGAA ATTGAGCAAG ACATGCTCAC CGAAATCCAC
4201 CACATACTGC CCAAACACAA GGGTGGTACT GACGACCTGG ACAATCTTGT CCTAATCCAC
4261 ACTAACTGCC ACAAACAGGT GCACAACCGA GATGGTCAGC ACAGCCGGTT CCTCTTGAAA
4321 GAGGGGCTTT GACTGCAGGC AAGCTTGGCA CTGGCCGTCG TTTTACAACG TCGTGACTGG
4381 GAAAACCCTG GCGTTACCCA ACTTAATCGC CTTGCAGCAC ATCCCCCTTT CGCCAGCTGG
4441 CGTAATAGCG AAGAGGCCCG CACCGATCGC CCTTCCCAAC AGTTGCGCAG CCTGAATGGC
4501 GAATGGCAGC TTGGCTGTTT TGGCGGATGA GATAAGATTT TCAGCCTGAT ACAGATTAAA
4561 TCAGAACGCA GAAGCGGTCT GATAAAACAG AATTTGCCTG GCGGCAGTAG CGCGGTGGTC
4621 CCACCTGACC CCATGCCGAA CTCAGAAGTG AAACGCCGTA GCGCCGATGG TAGTGTGGGG
4681 TCTCCCCATG CGAGAGTAGG GAACTGCCAG GCATCAAATA AAACGAAAGG CTCAGTCGAA
4741 AGACTGGGCG TTTCGTTTTA TCTGTTGTTT GTCGGTGAAC GCTCTCCTGA GTAGGACAAA
4801 TCCGCCGGGA GCGGATTTGA ACGTTGCGAA GCAACGGCCC GGAGGGTGGC GGGCAGGACG
4861 CCCGCCATAA ACTGCCAGGC ATCAAATTAA GCAGAAGGCC ATCCTGACGG ATGGCCTTTT
4921 TGCGTTTCTA CAAACTCTTT TTGTTTATTT TTCTAAATAC ATTCAAATAT GTATCCGCTC
4981 ATGAGACAAT AACCCTGATA AATGCTTCAA TAATATTGAA AAAGGAAGAG TATGAGTATT
5041 CAACATTTCC GTGTCGCCCT TATTCCCTTT TTTGCGGCAT TTTGCCTTCC TGTTTTTGCT
5101 CACCCAGAAA CGCTGGTGAA AGTAAAAGAT GCTGAAGATC AGTTGGGTGC ACGAGTGGGT
5161 TACATCGAAC TGGATCTCAA CAGCGGTAAG ATCCTTGAGA GTTTTCGCCC CGAAGAACGT
5221 TCTCCAATGA TGAGCACTTT TAAAGTTCTG CTATGTGGCG CGGTATTATC CCGTGTTGAC
5281 GCCGGGCAAG AGCAACTCGG TCGCCGCATA CACTATTCTC AGAATGACTT GGTTGAGTAC
5341 TCACCAGTCA CAGAAAAGCA TCTTACGGAT GGCATGACAG TAAGAGAATT ATGCAGTGCT
5401 GCCATAACCA TGAGTGATAA CACTGCGGCC AACTTACTTC TGACAACGAT CGGAGGACCG
5461 AAGGAGCTAA CCGCTTTTTT GCACAACATG GGGGATCATG TAACTCGCCT TGATCGTTGG
5521 GAACCGGAGC TGAATGAAGC CATACCAAAC GACGAGCGTG ACACCACGAT GCCTGTAGCA
5581 ATGGCAACAA CGTTGCGCAA ACTATTAACT GGCGAACTAC TTACTCTAGC TTCCCGGCAA
5641 CAATTAATAG ACTGGATGGA GGCGGATAAA GTTGCAGGAC CACTTCTGCG CTCGGCCCTT
5701 CCGGCTGGCT GGTTTATTGC TGATAAATCT GGAGCCGGTG AGCGTGGGTC TCGCGGTATC
5761 ATTGCAGCAC TGGGGCCAGA TGGTAAGCCC TCCCGTATCG TAGTTATCTA CACGACGGGG
5821 AGTCAGGCAA CTATGGATGA ACGAAATAGA CAGATCGCTG AGATAGGTGC CTCACTGATT
5881 AAGCATTGGT AACTGTCAGA CCAAGTTTAC TCATATATAC TTTAGATTGA TTTACCCCGG
5941 TTGATAATCA GAAAAGCCCC AAAAACAGGA AGATTGTATA AGCAAATATT TAAATTGTAA
6001 ACGTTAATAT TTTGTTAAAA TTCGCGTTAA ATTTTTGTTA AATCAGCTCA TTTTTTAACC
6061 AATAGGCCGA AATCGGCAAA ATCCCTTATA AATCAAAAGA ATAGACCGAG ATAGGGTTGA
6121 GTGTTGTTCC AGTTTGGAAC AAGAGTCCAC TATTAAAGAA CGTGGACTCC AACGTCAAAG
6181 GGCGAAAAAC CGTCTATCAG GGCGATGGCC CACTACGTGA ACCATCACCC AAATCAAGTT
6241 TTTTGGGGTC GAGGTGCCGT AAAGCACTAA ATCGGAACCC TAAAGGGAGC CCCCGATTTA
6301 GAGCTTGACG GGGAAAGCCG GCGAACGTGG CGAGAAAGGA AGGGAAGAAA GCGAAAGGAG
6361 CGGGCGCTAG GGCGCTGGCA AGTGTAGCGG TCACGCTGCG CGTAACCACC ACACCCGCCG
6421 CGCTTAATGC GCCGCTACAG GGCGCGTAAA AGGATCTAGG TGAAGATCCT TTTTGATAAT
6481 CTCATGACCA AAATCCCTTA ACGTGAGTTT TCGTTCCACT GAGCGTCAGA CCCCGTAGAA
6541 AAGATCAAAG GATCTTCTTG AGATCCTTTT TTTCTGCGCG TAATCTGCTG CTTGCAAACA
6601 AAAAACCAC CGCTACCAGC GGTGGTTTGT TGCCGGATC AAGAGCTACC AACTCTTTTT
6661 CCGAAGGTAA CTGGCTTCAG CAGAGCGCAG ATACCAAATA CTGTCCTTCT AGTGTAGCCG
6721 TAGTTAGGCC ACCACTTCAA GAACTCTGTA GCACCGCCTA CATACCTCGC TCTGCTAATC
6781 CTGTTACCAG TGGCTGCTGC CAGTGGCGAT AAGTCGTGTC TTACCGGGTT GGACTCAAGA
6841 CGATAGTTAC CGGATAAGGC GCAGCGGTCG GGCTGAACGG GGGGTTCGTG CACACAGCCC
6901 AGCTTGGAGC GAACGACCTA CACCGAACTG AGATACCTAC AGCGTGAGCT ATGAGAAAGC
6961 GCCACGCTTC CCGAAGGGAG AAAGGCGGAC AGGTATCCGG TAAGCGGCAG GGTCGGAACA
7021 GGAGAGCGCA CGAGGGAGCT TCCAGGGGGA AACGCCTGGT ATCTTTATAG TCCTGTCGGG
7081 TTTCGCCACC TCTGACTTGA GCGTCGATTT TTGTGATGCT CGTCAGGGGG GCGGAGCCTA
7141 TGGAAAAACG CCAGCAACGC GGCCTTTTTA CGGTTCCTGG CCTTTTGCTG GCCTTTTGCT
```

FIG. 7 (cont.)

```
7201 CACATGTTCT TTCCTGCGTT ATCCCCTGAT TCTGTGGATA ACCGTATTAC CGCCTTTGAG
7261 TGAGCTGATA CCGCTCGCCG CAGCCGAACG ACCGAGCGCA GCGAGTCAGT GAGCGAGGAA
7321 GCGGAAGAGC GCCTGATGCG GTATTTTCTC CTTACGCATC TGTGCGGTAT TTCACACCGC
7381 ATATATGGTG CACTCTCAGT ACAATCTGCT CTGATGCCGC ATAGTTAAGC CAGTATACAC
7441 TCCGCTATCG CTACGTGACT GGGTCATGGC TGCGCCCGA CACCCGCCAA CACCCGCTGA
7501 CGCGCCCTGA CGGGCTTGTC TGCTCCCGGC ATCCGCTTAC AGACAAGCTG TGACCGTCTC
7561 CGGGAGCTGC ATGTGTCAGA GGTTTTCACC GTCATCACCG AAACGCGCGA GGCAGCTGCG
7621 GTAAAGCTCA TCAGCGTGGT CGTGCAGCGA TTCACAGATG TCTGCCTGTT CATCCGCGTC
7681 CAGCTCGTTG AGTTTCTCCA GAAGCGTTAA TGTCTGGCTT CTGATAAAGC GGGCCATGTT
7741 AAGGGCGGTT TTTTCCTGTT TGGTCACTGA TGCCTCCGTG TAAGGGGGAT TTCTGTTCAT
7801 GGGGGTAATG ATACCGATGA AACGAGAGAG GATGCTCACG ATACGGGTTA CTGATGATGA
7861 ACATGCCCGG TTACTGAAC GTTGTGAGGG TAAACAACTG GCGGTATGGA TGCGGCGGGA
7921 CCAGAGAAAA ATCACTCAGG GTCAATGCCA GCGCTTCGTT AATACAGATG TAGGTGTTCC
7981 ACAGGGTAGC CAGCAGCATC CTGCGATGCA GATCCGGAAC ATAATGGTGC AGGGCGCTGA
8041 CTTCCGCGTT TCCAGACTTT ACGAAACACG GAAACCGAAG ACCATTCATG TTGTTGCTCA
8101 GGTCGCAGAC GTTTTGCAGC AGCAGTCGCT TCACGTTCGC TCGCGTATCG GTGATTCATT
8161 CTGCTAACCA GTAAGGCAAC CCCGCCAGCC TAGCCGGGTC CTCAACGACA GGAGCACGAT
8221 CATGCGCACC CGTGGCCAGG ACCCAACGCT GCCCGAAATT
```

FIG. 7 (cont.)

SEQ ID NO: 15

```
   1 CCGACACCAT CGAATGGTGC AAAACCTTTC GCGGTATGGC ATGATAGCGC CCGGAAGAGA
  61 GTCAATTCAG GGTGGTGAAT GTGAAACCAG TAACGTTATA CGATGTCGCA GAGTATGCCG
 121 GTGTCTCTTA TCAGACCGTT TCCCGCGTGG TGAACCAGGC CAGCCACGTT TCTGCGAAAA
 181 CGCGGGAAAA AGTGGAAGCG GCGATGGCGG AGCTGAATTA CATTCCCAAC CGCGTGGCAC
 241 AACAACTGGC GGGCAAACAG TCGTTGCTGA TTGGCGTTGC CACCTCCAGT CTGGCCCTGC
 301 ACGCGCCGTC GCAAATTGTC GCGGCGATTA AATCTCGCGC CGATCAACTG GGTGCCAGCG
 361 TGGTGGTGTC GATGGTAGAA CGAAGCGGCG TCGAAGCCTG TAAAGCGGCG GTGCACAATC
 421 TTCTCGCGCA ACGCGTCAGT GGGCTGATCA TTAACTATCC GCTGGATGAC CAGGATGCCA
 481 TTGCTGTGGA AGCTGCCTGC ACTAATGTTC CGGCGTTATT TCTTGATGTC TCTGACCAGA
 541 CACCCATCAA CAGTATTATT TTCTCCCATG AAGACGGTAC GCGACTGGGC GTGGAGCATC
 601 TGGTCGCATT GGGTCACCAG CAAATCGCGC TGTTAGCGGG CCCATTAAGT TCTGTCTCGG
 661 CGCGTCTGCG TCTGGCTGGC TGGCATAAAT ATCTCACTCG CAATCAAATT CAGCCGATAG
 721 CGGAACGGGA AGGCGACTGG AGTGCCATGT CCGGTTTTCA ACAAACCATG CAAATGCTGA
 781 ATGAGGGCAT CGTTCCCACT GCGATGCTGG TTGCCAACGA TCAGATGGCG CTGGGCGCAA
 841 TGCGCGCCAT TACCGAGTCC GGGCTGCGCG TTGGTGCGGA TATCTCGGTA GTGGGATACG
 901 ACGATACCGA AGACACGCTCA TGTTATATCC CGCCGTTAAC CACCATCAAA CAGGATTTTC
 961 GCCTGCTGGG GCAAACCAGC GTGGACCGCT TGCTGCAACT CTCTCAGGGC CAGGCGGTGA
1021 AGGGCAATCA GCTGTTGCCC GTCTCACTGG TGAAAGAAA AACCACCCTG GCGCCCAATA
1081 CGCAAACCGC CTCTCCCCGC GCGTTGGCCG ATTCATTAAT GCAGCTGGCA CGACAGGTTT
1141 CCCGACTGGA AAGCGGGCAG TGAGCGCAAC GCAATTAATG TAAGTTAGCT CACTCATTAG
1201 GCACAATTCT CATGTTTGAC AGCTTATCAT CGACTGCACG GTGCACCAAT GCTTCTGGCG
1261 TCAGGCAGCC ATCGGAAGCT GTGGTATGGC TGTGCAGGTC GTAAATCACT GCATAATTCG
1321 TGTCGCTCAA GGCGCACTCC CGTTCTGGAT AATGTTTTTT GCGCCGACAT CATAACGGTT
1381 CTGGCAAATA TTCTGAAATG AGCTGTTGAC AATTAATCAT CGGCTCGTAT AATGTGTGGA
1441 ATTGTGAGCG GATAACAATT TCACACAGGA AACAGCCAGT CCGTTTAGGT GTTTTCACGA
1501 GCACTTCACC AACAAGGACC ATAGCATATG AAAATCGAAG AAGGTAAACT GGTAATCTGG
1561 ATTAACGGCG ATAAAGGCTA TAACGGTCTC GCTGAAGTCG GTAAGAAATT CGAGAAAGAT
1621 ACCGGAATTA AAGTCACCGT TGAGCATCCG GATAAACTGG AAGAGAAATT CCCACAGGTT
1681 GCGGCAACTG GCGATGGCCC TGACATTATC TTCTGGGCAC ACGACCGCTT TGGTGGCTAC
1741 GCTCAATCTG GCCTGTTGGC TGAAATCACC CCGGACAAAG CGTTCCAGGA CAAGCTGTAT
1801 CCGTTTACCT GGGATGCCGT ACGTTACAAC GGCAAGCTGA TTGCTTACCC GATCGCTGTT
1861 GAAGCGTTAT CGCTGATTTA TAACAAAGAT CTGCTGCCGA ACCCGCCAAA AACCTGGGAA
1921 GAGATCCCGG CGCTGGATAA AGAACTGAAA GCGAAGGTA AGAGCGCGCT GATGTTCAAC
1981 CTGCAAGAAC CGTACTTCAC CTGGCCGCTG ATTGCTGCTG ACGGGGGTTA TGCGTTCAAG
2041 TATGAAAACG GCAAGTACGA CATTAAAGAC GTGGGCGTGG ATAACGCTGG CGCGAAAGCG
2101 GGTCTGACCT TCCTGGTTGA CCTGATTAAA AACAAACACA TGAATGCAGA CACCGATTAC
2161 TCCATCGCAG AAGCTGCCTT TAATAAAGGC GAAACAGCGA TGACCATCAA CGGCCCGTGG
2221 GCATGGTCCA ACATCGACAC CAGCAAAGTG AATTATGGTG TAACGGTACT GCCGACCTTC
2281 AAGGGTCAAC CATCCAAACC GTTCGTTGGC GTGCTGAGCG CAGGTATTAA CGCCGCCAGT
2341 CCGAACAAAG AGCTGGCAAA AGAGTTCCTC GAAAACTATC TGCTGACTGA TGAAGGTCTG
2401 GAAGCGGTTA ATAAAGACAA ACCGCTGGGT GCCGTAGCGC TGAAGTCTTA CGAGGAAGAG
2461 TTGGCGAAAG ATCCACGTAT TGCCGCCACT ATGGAAAACG CCCAGAAAGG TGAAATCATG
2521 CCGAACATCC CGCAGATGTC CGCTTTCTGG TATGCCGTGC GTACTGCGGT GATCAACGCC
2581 GCCAGCGGTC GTCAGACTGT CGATGCCGCC CTGGCCGCCG CGCAGACTGC CGCCGCCGCC
2641 GCCATGGAGA CAAGGCAAAT GGCAGTGGAA CAAACCACTG GTGCGGTCAC CAACCAAACG
2701 GAAACAAGCT GGCACAGCAT AGACTGGGCC AAAGCCAACC GTGAGGTAAA GAGGCTGCAA
2761 GTGCGTATCG CAAAGGCTGT GAAGGAAGGA CGCTGGGGCA AAGTGAAAGC TTTGCAATGG
2821 CTCCTGACCC ACTCGTTCTA CGGCAAAGCC CTCGCCGTGA ACGGGTAAC TGACAACTCG
2881 GGCAGCAAAA CACCTGGTGT GGACGGGATA ACCTGGTCCA CACAAGAGCA GAAAGCCCAA
2941 GCCATAAAGT CCCTCAGGAG AAGAGGCTAC AAACCCCAAC CCCTGAGGCG GTATACATC
3001 CCGAAAGCAA GCGGCAAGCA GCGCCCGCTA GGAATCCCGA CAACGAAGGA CAGGGCAATG
3061 CAGGCATTAT ATGCCCTAGC TCTAGAACCT GTCGCGGAAA CCACAGCGGA TCGGAACTCA
3121 TACGGGTTCC GTCAAGGACG GTGCACGGCA GATGCTGCCG GGCAGTGCTT CACTGTGCTA
3181 GGCCGATCTG ACTGTGCAAA ATATATCCTT GATGCTGACA TCACCGGATG CTTTGACAAC
3241 ATTAGCCACG AATGGCTACT AGACAACATC CCGCTGGACA AAGAGGTTCT GCGGAAGTGG
3301 CTTAAATCTG GGTTCGTCTG GAAACAGCAA CTCTTCCCAA CCCATGCTGG GACACCTCAG
3361 GGAGGGGTAA TCTCCCCAAT GCTGGCCAAT ATGACCCTAG ATGGGATGGA AGAATTGCTG
3421 AAGAAACACC TCAGAAAACA AAAGTCAAC CTCATACGAT ATGCAGACGA CTTTGTCGTA
3481 ACTGGTGAAT CAAAGGAAAC CTTGGAAAAG GTTACAACTG TAATCCAAGA ATTCCTCAAG
```

FIG. 8

```
3541 GAAAGGGGCC TTACCCTATC AGAAGAAAAG ACAAAGGTCG TTCATATCGA AGAAGGATTT
3601 GACTTTCTTG GATGGAACAT TCGCAAATAT GGTGAGAAGC TTCTCATCAA ACCTGCGAAG
3661 AAGAACATCA AGGCGTTCCA CAAGAAAATC CGAGACGCAC TGAAGGAACT CAGAACAGCC
3721 ACCCAGGAAG CTGTGATAGA CACACTCAAC CCAATTATCA AAGGCTGGGC TAACTATCAC
3781 AGAAACCAGG TTTCCAAAAG AATCTTCAAC AGAGCGGATG ACAATATCTG GCATAAATTA
3841 TGGCGATGGG CAAAACGTCG GCACCCAAAC AAACCAGCCC GATGGACAAA GAACAAATAC
3901 TTCATCAAAA TCGGGAATAG GCACTGGGTG TTTGGCACAT GGAAAAAGGA CAAAGAGGGA
3961 AGGTTACGGT CCAGATACCT AATTAAAGCC GGAGATACTC GAATCCAACG TCATGTCAAA
4021 ATCAAGGCAG ACGCCAATCC GTTTCTCCCA GAGTGGGCAG AATACTTTGA GGAACGCAAG
4081 AAACTCAAAG AAGCCCCTGC TCAATATCGG CGCATCCGCC GAGAACTATG GAAGAAACAG
4141 GGTGGTATCT GTCCAGTATG CGGGGGTGAA ATTGAGCAAG ACATGCTCAC TGAAATCCAC
4201 CACATATTGC CCAAACACAA GGGTGGTTCT GACGACCTGG ATAATCTTGT CTTAATCCAC
4261 GCCAACTGTC ACAAACAGGT GCACAGCCGA GACGGTCAGC ACAGCCGGTT CCTCTTGAAA
4321 GAGGGGCTTT GACTGCAGGC AAGCTTGGCA CTGGCCGTCG TTTTACAACG TCGTGACTGG
4381 GAAAACCCTG GCGTTACCCA ACTTAATCGC CTTGCAGCAC ATCCCCCTTT CGCCAGCTGG
4441 CGTAATAGCG AAGAGGCCCG CACCGATCGC CCTTCCCAAC AGTTGCGCAG CCTGAATGGC
4501 GAATGGCAGC TTGGCTGTTT TGGCGGATGA GATAAGATTT TCAGCCTGAT ACAGATTAAA
4561 TCAGAACGCA GAAGCGGTCT GATAAACAG AATTTGCCTG GCGGCAGTAG CGCGGTGGTC
4621 CCACCTGACC CCATGCCGAA CTCAGAAGTG AAACGCCGTA GCGCCGATGG TAGTGTGGGG
4681 TCTCCCCATG CGAGAGTAGG GAACTGCCAG GCATCAAATA AAACGAAAGG CTCAGTCGAA
4741 AGACTGGGCC TTTCGTTTTA TCTGTTGTTT GTCGGTGAAC GCTCTCCTGA GTAGGACAAA
4801 TCCGCCGGGA GCGGATTTGA ACGTTGCGAA GCAACGGCCC GGAGGGTGGC GGGCAGGACG
4861 CCCGCCATAA ACTGCCAGGC ATCAAATTAA GCAGAAGGCC ATCCTGACGG ATGGCCTTTT
4921 TGCGTTTCTA CAAACTCTTT TTGTTTATTT TTCTAAATAC ATTCAAATAT GTATCCGCTC
4981 ATGAGACAAT AACCCTGATA AATGCTTCAA TAATATTGAA AAAGGAAGAG TATGAGTATT
5041 CAACATTTCC GTGTCGCCCT TATTCCCTTT TTTGCGGCAT TTTGCCTTCC TGTTTTTGCT
5101 CACCCAGAAA CGCTGGTGAA AGTAAAAGAT GCTGAAGATC AGTTGGGTGC ACGAGTGGGT
5161 TACATCGAAC TGGATCTCAA CAGCGGTAAG ATCCTTGAGA GTTTTCGCCC CGAAGAACGT
5221 TCTCCAATGA TGAGCACTTT TAAAGTTCTG CTATGTGGCG CGGTATTATC CCGTGTTGAC
5281 GCCGGGCAAG AGCAACTCGG TCGCCGCATA CACTATTCTC AGAATGACTT GGTTGAGTAC
5341 TCACCAGTCA CAGAAAAGCA TCTTACGGAT GGCATGACAG TAAGAGAATT ATGCAGTGCT
5401 GCCATAACCA TGAGTGATAA CACTGCGGCC AACTTACTTC TGACAACGAT CGGAGGACCG
5461 AAGGAGCTAA CCGCTTTTTT GCACAACATG GGGGATCATG TAACTCGCCT TGATCGTTGG
5521 GAACCGGAGC TGAATGAAGC CATACCAAAC GACGAGCGTG ACACCACGAT GCCTGTAGCA
5581 ATGGCAACAA CGTTGCGCAA ACTATTAACT GGCGAACTAC TTACTCTAGC TTCCCGGCAA
5641 CAATTAATAG ACTGGATGGA GGCGGATAAA GTTGCAGGAC CACTTCTGCG CTCGGCCCTT
5701 CCGGCTGGCT GGTTTATTGC TGATAAATCT GGAGCCGGTG AGCGTGGGTC TCGCGGTATC
5761 ATTGCAGCAC TGGGGCCAGA TGGTAAGCCC TCCCGTATCG TAGTTATCTA CACGACGGGG
5821 AGTCAGGCAA CTATGGATGA ACGAAATAGA CAGATCGCTG AGATAGGTGC CTCACTGATT
5881 AAGCATTGGT AACTGTCAGA CCAAGTTTAC TCATATATAC TTTAGATTGA TTTACCCCGG
5941 TTGATAATCA GAAAAGCCCC AAAAACAGGA AGATTGTATA AGCAAATATT TAAATTGTAA
6001 ACGTTAATAT TTTGTTAAAA TTCGCGTTAA ATTTTTGTTA AATCAGCTCA TTTTTTAACC
6061 AATAGGCCGA AATCGGCAAA ATCCCTTATA AATCAAAAGA ATAGACCGAG ATAGGGTTGA
6121 GTGTTGTTCC AGTTTGGAAC AAGAGTCCAC TATTAAAGAA CGTGGACTCC AACGTCAAAG
6181 GGCGAAAAAC CGTCTATCAG GGCGATGGCC CACTACGTGA ACCATCACCC AAATCAAGTT
6241 TTTTGGGGTC GAGGTGCCGT AAAGCACTAA ATCGGAACCC TAAAGGGAGC CCCCGATTTA
6301 GAGCTTGACG GGGAAAGCCG GCGAACGTGG CGAGAAAGGA AGGGAAGAAA GCGAAAGGAG
6361 CGGGCGCTAG GGCGCTGGCA AGTGTAGCGG TCACGCTGCG CGTAACCACC ACACCCGCCG
6421 CGCTTAATGC GCCGCTACAG GGCGCGTAAA AGGATCTAGG TGAAGATCCT TTTTGATAAT
6481 CTCATGACCA AAATCCCTTA ACGTGAGTTT TCGTTCCACT GAGCGTCAGA CCCCGTAGAA
6541 AAGATCAAAG GATCTTCTTG AGATCCTTTT TTTCTGCGCG TAATCTGCTG CTTGCAAACA
6601 AAAAACCAC CGCTACCAGC GGTGGTTTGT TGCCGGATC AAGAGCTACC AACTCTTTTT
6661 CCGAAGGTAA CTGGCTTCAG CAGAGCGCAG ATACCAAATA CTGTCCTTCT AGTGTAGCCG
6721 TAGTTAGGCC ACCACTTCAA GAACTCTGTA GCACCGCCTA CATACCTCGC TCTGCTAATC
6781 CTGTTACCAG TGGCTGCTGC CAGTGGCGAT AAGTCGTGTC TTACCGGGTT GGACTCAAGA
6841 CGATAGTTAC CGGATAAGGC GCAGCGGTCG GGCTGAACGG GGGGTTCGTG CACACAGCCC
6901 AGCTTGGAGC GAACGACCTA CACCGAACTG AGATACCTAC AGCGTGAGCT ATGAGAAAGC
6961 GCCACGCTTC CCGAAGGGAG AAAGGCGGAC AGGTATCCGG TAAGCGGCAG GGTCGGAACA
7021 GGAGAGCGCA CGAGGGAGCT TCCAGGGGGA AACGCCTGGT ATCTTTATAG TCCTGTCGGG
7081 TTTCGCCACC TCTGACTTGA GCGTCGATTT TTGTGATGCT CGTCAGGGGG GCGGAGCCTA
7141 TGGAAAAACG CCAGCAACGC GGCCTTTTTA CGGTTCCTGG CCTTTTGCTG GCCTTTTGCT
```

FIG. 8 (cont.)

```
7201 CACATGTTCT TTCCTGCGTT ATCCCCTGAT TCTGTGGATA ACCGTATTAC CGCCTTTGAG
7261 TGAGCTGATA CCGCTCGCCG CAGCCGAACG ACCGAGCGCA GCGAGTCAGT GAGCGAGGAA
7321 GCGGAAGAGC GCCTGATGCG GTATTTTCTC CTTACGCATC TGTGCGGTAT TTCACACCGC
7381 ATATATGGTG CACTCTCAGT ACAATCTGCT CTGATGCCGC ATAGTTAAGC CAGTATACAC
7441 TCCGCTATCG CTACGTGACT GGGTCATGGC TGCGCCCCGA CACCCGCCAA CACCCGCTGA
7501 CGCGCCCTGA CGGGCTTGTC TGCTCCCGGC ATCCGCTTAC AGACAAGCTG TGACCGTCTC
7561 CGGGAGCTGC ATGTGTCAGA GGTTTTCACC GTCATCACCG AAACGCGCGA GGCAGCTGCG
7621 GTAAAGCTCA TCAGCGTGGT CGTGCAGCGA TTCACAGATG TCTGCCTGTT CATCCGCGTC
7681 CAGCTCGTTG AGTTTCTCCA GAAGCGTTAA TGTCTGGCTT CTGATAAAGC GGGCCATGTT
7741 AAGGGCGGTT TTTTCCTGTT TGGTCACTGA TGCCTCCGTG TAAGGGGGAT TTCTGTTCAT
7801 GGGGGTAATG ATACCGATGA AACGAGAGAG GATGCTCACG ATACGGGTTA CTGATGATGA
7861 ACATGCCCGG TTACTGGAAC GTTGTGAGGG TAAACAACTG GCGGTATGGA TGCGGCGGGA
7921 CCAGAGAAAA ATCACTCAGG GTCAATGCCA GCGCTTCGTT AATACAGATG TAGGTGTTCC
7981 ACAGGGTAGC CAGCAGCATC CTGCGATGCA GATCCGGAAC ATAATGGTGC AGGGCGCTGA
8041 CTTCCGCGTT TCCAGACTTT ACGAAACACG GAAACCGAAG ACCATTCATG TTGTTGCTCA
8101 GGTCGCAGAC GTTTTGCAGC AGCAGTCGCT TCACGTTCGC TCGCGTATCG GTGATTCATT
8161 CTGCTAACCA GTAAGGCAAC CCCGCCAGCC TAGCCGGGTC CTCAACGACA GGAGCACGAT
8221 CATGCGCACC CGTGGCCAGG ACCCAACGCT GCCCGAAATT
```

FIG. 8 (cont.)

SEQ ID NO: 16

```
   1 CCGACACCAT CGAATGGTGC AAAACCTTTC GCGGTATGGC ATGATAGCGC CCGGAAGAGA
  61 GTCAATTCAG GGTGGTGAAT GTGAAACCAG TAACGTTATA CGATGTCGCA GAGTATGCCG
 121 GTGTCTCTTA TCAGACCGTT TCCCGCGTGG TGAACCAGGC CAGCCACGTT TCTGCGAAAA
 181 CGCGGGAAAA AGTGGAAGCG GCGATGGCGG AGCTGAATTA CATTCCCAAC CGCGTGGCAC
 241 AACAACTGGC GGGCAAACAG TCGTTGCTGA TTGGCGTTGC CACCTCCAGT CTGGCCCTGC
 301 ACGCGCCGTC GCAAATTGTC GCGGCGATTA AATCTCGCGC CGATCAACTG GGTGCCAGCG
 361 TGGTGGTGTC GATGGTAGAA CGAAGCGGCG TCGAAGCCTG TAAAGCGGCG GTGCACAATC
 421 TTCTCGCGCA ACGCGTCAGT GGGCTGATCA TTAACTATCC GCTGGATGAC CAGGATGCCA
 481 TTGCTGTGGA AGCTGCCTGC ACTAATGTTC CGGCGTTATT TCTTGATGTC TCTGACCAGA
 541 CACCCATCAA CAGTATTATT TTCTCCCATG AAGACGGTAC GCGACTGGGC GTGGAGCATC
 601 TGGTCGCATT GGGTCACCAG CAAATCGCGC TGTTAGCGGG CCCATTAAGT TCTGTCTCGG
 661 CGCGTCTGCG TCTGGCTGGC TGGCATAAAT ATCTCACTCG CAATCAAATT CAGCCGATAG
 721 CGGAACGGGA AGGCGACTGG AGTGCCATGT CCGGTTTTCA ACAAACCATG CAAATGCTGA
 781 ATGAGGGCAT CGTTCCCACT GCGATGCTGG TTGCCAACGA TCAGATGGCG CTGGGCGCAA
 841 TGCGCGCCAT TACCGAGTCC GGGCTGCGCG TTGGTGCGGA TATCTCGGTA GTGGGATACG
 901 ACGATACCGA AGACAGCTCA TGTTATATCC CGCCGTTAAC CACCATCAAA CAGGATTTTC
 961 GCCTGCTGGG GCAAACCAGC GTGGACCGCT TGCTGCAACT CTCTCAGGGC CAGGCGGTGA
1021 AGGGCAATCA GCTGTTGCCC GTCTCACTGG TGAAAAGAAA AACCACCCTG GCGCCCAATA
1081 CGCAAACCGC CTCTCCCCGC GCGTTGGCCG ATTCATTAAT GCAGCTGGCA CGACAGGTTT
1141 CCCGACTGGA AAGCGGGCAG TGAGCGCAAC GCAATTAATG TAAGTTAGCT CACTCATTAG
1201 GCACAATTCT CATGTTTGAC AGCTTATCAT CGACTGCACG GTGCACCAAT GCTTCTGGCG
1261 TCAGGCAGCC ATCGGAAGCT GTGGTATGGC TGTGCAGGTC GTAAATCACT GCATAATTCG
1321 TGTCGCTCAA GGCGCACTCC CGTTCTGGAT AATGTTTTTT GCGCCGACAT CATAACGGTT
1381 CTGGCAAATA TTCTGAAATG AGCTGTTGAC AATTAATCAT CGGCTCGTAT AATGTGTGGA
1441 ATTGTGAGCG GATAACAATT TCACACAGGA AACAGCCAGT CCGTTTAGGT GTTTTCACGA
1501 GCACTTCACC AACAAGGACC ATAGCATATG AAAATCGAAG AAGGTAAACT GGTAATCTGG
1561 ATTAACGGCG ATAAAGGCTA TAACGGTCTC GCTGAAGTCG GTAAGAAATT CGAGAAAGAT
1621 ACCGGAATTA AAGTCACCGT TGAGCATCCG GATAAACTGG AAGAGAAATT CCCACAGGTT
1681 GCGGCAACTG GCGATGGCCC TGACATTATC TTCTGGGCAC ACGACCGCTT TGGTGGCTAC
1741 GCTCAATCTG GCCTGTTGGC TGAAATCACC CCGGACAAAG CGTTCCAGGA CAAGCTGTAT
1801 CCGTTTACCT GGGATGCCGT ACGTTACAAC GGCAAGCTGA TTGCTTACCC GATCGCTGTT
1861 GAAGCGTTAT CGCTGATTTA TAACAAAGAT CTGCTGCCGA ACCCGCCAAA AACCTGGGAA
1921 GAGATCCCGG CGCTGGATAA AGAACTGAAA GCGAAAGGTA AGAGCGCGCT GATGTTCAAC
1981 CTGCAAGAAC CGTACTTCAC CTGGCCGCTG ATTGCTGCTG ACGGGGGTTA TGCGTTCAAG
2041 TATGAAAACG GCAAGTACGA CATTAAAGAC GTGGGCGTGG ATAACGCTGG CGCGAAAGCG
2101 GGTCTGACCT TCCTGGTTGA CCTGATTAAA AACAAACACA TGAATGCAGA CACCGATTAC
2161 TCCATCGCAG AAGCTGCCTT TAATAAAGGC GAAACAGCGA TGACCATCAA CGGCCCGTGG
2221 GCATGGTCCA ACATCGACAC CAGCAAAGTG AATTATGGTG TAACGGTACT GCCGACCTTC
2281 AAGGGTCAAC CATCCAAACC GTTCGTTGGC GTGCTGAGCG CAGGTATTAA CGCCGCCAGT
2341 CCGAACAAAG AGCTGGCAAA AGAGTTCCTC GAAAACTATC TGCTGACTGA TGAAGGTCTG
2401 GAAGCGGTTA ATAAAGACAA ACCGCTGGGT GCCGTAGCGC TGAAGTCTTA CGAGGAAGAG
2461 TTGGCGAAAA ATCCACGTAT TGCCGCCACT ATGGAAAACG CCCAGAAAGG TGAAATCATG
2521 CCGAACATCC CGCAGATGTC CGCTTTCTGG TATGCCGTGC GTACTGCGGT GATCAACGCC
2581 GCCAGCGGTC GTCAGACTGT CGATGCCGCC CTGGCCGCCG CGCAGACTGC CGCCGCCGCC
2641 GCCATGAAGG TAAACAAACT TGTCGTAAAA AGCGAACAGG ACTTGAGAAA CTGCTTGGAT
2701 CTTCTTTATC AAGAAGCTAA AAAGGGAAAA CATTTTTACG GCATGCTTGA GTTGCTTCAA
2761 AATGATGTTG TCATTTTAGA AGCTATTCGC AATATTAAAA GCAATAAAGG TAGCAAAACG
2821 GCGGGGATTG ATCAGAAAAT AGTAGATGAT TATTTGCTTA TGCCAACGGA AAAGGTTTTC
2881 GGGATGATAA AAGCCAAACT CAATGACTAT AAGCCTATAC CAGTGAGAAG GTGCAACAAG
2941 CCCAAAGGAA ATGCCAAAAG CTCAAAAAGA AAAGGCAATA GTCCGAATGA GGAAGGGGAA
3001 ACGAGGCCCT TAGGAATATC CGCAGTGACG GATAGAATCA TCCAAGAGAT GCTACGGATA
3061 GTGCTCGAGC CGATTTTCGA AGCCCAATTC TATCCGCACA GTTATGGGTT CAGACCGTAT
3121 CGCTCCACCG AACATGCCTT AGCCTGGATG CTGAAAATCA TCAACGGAAG CAAACTGTAT
3181 TGGGTTGTAA AAGGTGCATT TGAAAGTTAT TTTGATACACA TCAATCATAA GAAGCTTCTG
3241 AACATCATGT GGAATATGGG CGTTAGGGAT AAACGGGTAC TATGCATCGT TAAGAAAATG
3301 CTGAAGGCGG GGCAAGTGAT ACAAGGTAAA TTCTATCCAA CCGCTAAGGG GATTCCTCAG
3361 GGAGGAATTA TTAGCCCGTT GTTGGCTAAT GTATATCTCA ACAGCTTTGA CTGGATGGTT
3421 GGCCAAGAAT ATGAGTATCA CCCTAATAAC GCAAACTATC GGGAAAGAA AAACGCATTA
3481 GCGGCGTTAA GGAACAAGGG ACATCATCCC GTCTTTTACA TTCGTTATGC TGATGATTGG
```

FIG. 9

```
3541 GTTATTCTTA CGGATACGAA AGAATATGCG GAAAAAATAA GGGAGCAATG TAAGCAGTAT
3601 TTAGCCTGTG AGTTGCACTT AACTCTATCG GATGAGAAAA CGTTCATTGC AGATATCCGC
3661 GAACAACGGG TTAAGTTTCT AGGCTTTTGT ATTGAGGCAG GAAAGCGGCG TTTTCATAAA
3721 AAAGGATTCG CCGCTAGAAT GATTCCCGAT ATGGAAAAAG TCAATGCCAA GGTCAAAGAA
3781 ATTAAGCGCG ATATTCGATT GTTAAGAACG AGAAAATCGG AATTAGAGAA AGCCCTTGAT
3841 ATTGAAAACA TTAACACCAA AATTATAGGA TTAGCCAATC ATCTAAAAAT AGGCATTTCC
3901 AAGTACATTA TGGGCAAAGT AGATCGCGTC ATTGAAGAGA CAGCCTACCG CACCTGGGTT
3961 AAAATGTATG GGAAAGAAAA AGCGGCGCAA TATAAAAGGC CTGTGTCAGA GTTTCACAAT
4021 CGGATTGACA GACATAAAGG CTATCAAATG AAACATTTTT CTGTCGTCAC AGAGGATGGC
4081 ATAAGAGTAG GGATTACCCA TGCAAAAATA ACGCCTATAC AGTATGCAAC AGTATTCAAA
4141 CAAGAAATGA CCCCATACAC TGCAGACGGC AGAAAAATGT ATGAAGAAAA GCATAGAAAA
4201 ATACGATTGC CGGATAAAAT GAGTCTGTTC GATCACGATT CGATATTCAT CTACATTTTA
4261 TCTGAGCATA ATGATGGAAA ATATAATCTT GAATATTTCT TAAATAGGGT GAATGTATTT
4321 CACAGAGATA AAGGAAAATG CAAATATGT GCCGTATACT TAAGTCCCGG TAACTTCCAC
4381 TGCCATCATA TTGACCCGAG TAAACCTTTA AGTGAGATCA ATAAGACCGT TAATCTAATT
4441 AGCTTATGCA ACCAATGCCA TAGGCTTGTC CATACAACC AAGAACCGCC GTTTACAGAA
4501 CGAAAAATGT TTGACAAACT AACGAAATAT AGGAACAAGC TGAAAATATA AGGATCCTCT
4561 AGCTGCAGGC AAGCTTGGCA CTGGCCGTCG TTTTACAACG TCGTGACTGG GAAAACCCTG
4621 GCGTTACCCA ACTTAATCGC CTTGCAGCAC ATCCCCCTTT CGCCAGCTGG CGTAATAGCG
4681 AAGAGGCCCG CACCGATCGC CCTTCCCAAC AGTTGCGCAG CCTGAATGGC GAATGGCAGC
4741 TTGGCTGTTT TGGCGGATGA GATAAGATTT TCAGCCTGAT ACAGATTAAA TCAGAACGCA
4801 GAAGCGGTCT GATAAACAG AATTTGCCTG GCGGCAGTAG CGCGGTGGTC CCACCTGACC
4861 CCATGCCGAA CTCAGAAGTG AAACGCCGTA GCGCCGATGG TAGTGTGGGG TCTCCCCATG
4921 CGAGAGTAGG GAACTGCCAG GCATCAAATA AAACGAAAGG CTCAGTCGAA AGACTGGGCC
4981 TTTCGTTTTA TCTGTTGTTT GTCGGTGAAC GCTCTCCTGA GTAGGACAAA TCCGCCGGGA
5041 GCGGATTTGA ACGTTGCGAA GCAACGGCCC GGAGGGTGGC GGGCAGGACG CCCGCCATAA
5101 ACTGCCAGGC ATCAAATTAA GCAGAAGGCC ATCCTGACGG ATGGCCTTTT TGCGTTTCTA
5161 CAAACTCTTT TTGTTTATTT TTCTAAATAC ATTCAAATAT GTATCCGCTC ATGAGACAAT
5221 AACCCTGATA AATGCTTCAA TAATATTGAA AAAGGAAGAG TATGAGTATT CAACATTTCC
5281 GTGTCGCCCT TATTCCCTTT TTTGCGGCAT TTTGCCTTCC TGTTTTTGCT CACCCAGAAA
5341 CGCTGGTGAA AGTAAAAGAT GCTGAAGATC AGTTGGGTGC ACGAGTGGGT TACATCGAAC
5401 TGGATCTCAA CAGCGGTAAG ATCCTTGAGA GTTTTCGCCC CGAAGAACGT TCTCCAATGA
5461 TGAGCACTTT TAAAGTTCTG CTATGTGGCG CGGTATTATC CCGTGTTGAC GCCGGGCAAG
5521 AGCAACTCGG TCGCCGCATA CACTATTCTC AGAATGACTT GGTTGAGTAC TCACCAGTCA
5581 CAGAAAAGCA TCTTACGGAT GGCATGACAG TAAGAGAATT ATGCAGTGCT GCCATAACCA
5641 TGAGTGATAA CACTGCGGCC AACTTACTTC TGACAACGAT CGGAGGACCG AAGGAGCTAA
5701 CCGCTTTTTT GCACAACATG GGGGATCATG TAACTCGCCT TGATCGTTGG GAACCGGAGC
5761 TGAATGAAGC CATACCAAAC GACGAGCGTG ACACCACGAT GCCTGTAGCA ATGGCAACAA
5821 CGTTGCGCAA ACTATTAACT GGCGAACTAC TTACTCTAGC TTCCCGGCAA CAATTAATAG
5881 ACTGGATGGA GGCGGATAAA GTTGCAGGAC CACTTCTGCG CTCGGCCCTT CCGGCTGGCT
5941 GGTTTATTGC TGATAAATCT GGAGCCGGTG AGCGTGGGTC TCGCGGTATC ATTGCAGCAC
6001 TGGGGCCAGA TGGTAAGCCC TCCCGTATCG TAGTTATCTA CACGACGGGG AGTCAGGCAA
6061 CTATGGATGA ACGAAATAGA CAGATCGCTG AGATAGGTGC CTCACTGATT AAGCATTGGT
6121 AACTGTCAGA CCAAGTTTAC TCATATATAC TTTAGATTGA TTTACCCCGG TTGATAATCA
6181 GAAAAGCCCC AAAAACAGGA AGATTGTATA AGCAAATATT TAAATTGTAA ACGTTAATAT
6241 TTTGTTAAAA TTCGCGTTAA ATTTTTGTTA AATCAGCTCA TTTTTTAACC AATAGGCCGA
6301 AATCGGCAAA ATCCCTTATA AATCAAAAGA ATAGACCGAG ATAGGGTTGA GTGTTGTTCC
6361 AGTTTGGAAC AAGAGTCCAC TATTAAAGAA CGTGGACTCC AACGTCAAAG GGCGAAAAAC
6421 CGTCTATCAG GGCGATGGCC CACTACGTGA ACCATCACCC AAATCAAGTT TTTTGGGGTC
6481 GAGGTGCCGT AAAGCACTAA ATCGGAACCC TAAAGGGAGC CCCCGATTTA GAGCTTGACG
6541 GGGAAAGCCG GCGAACGTGG CGAGAAAGGA AGGGAAGAAA GCGAAAGGAG CGGGCGCTAG
6601 GGCGCTGGCA AGTGTAGCGG TCACGCTGCG CGTAACCACC ACACCCGCCG CGCTTAATGC
6661 GCCGCTACAG GGCGCGTAAA AGGATCTAGG TGAAGATCCT TTTTGATAAT CTCATGACCA
6721 AAATCCCTTA ACGTGAGTTT TCGTTCCACT GAGCGTCAGA CCCCGTAGAA AAGATCAAAG
6781 GATCTTCTTG AGATCCTTTT TTTCTGCGCG TAATCTGCTG CTTGCAAACA AAAAAACCAC
6841 CGCTACCAGC GGTGGTTTGT TTGCCGGATC AAGAGCTACC AACTCTTTTT CCGAAGGTAA
6901 CTGGCTTCAG CAGAGCGCAG ATACCAAATA CTGTCCTTCT AGTGTAGCCG TAGTTAGGCC
6961 ACCACTTCAA GAACTCTGTA GCACCGCCTA CATACCTCGC TCTGCTAATC CTGTTACCAG
7021 TGGCTGCTGC CAGTGGCGAT AAGTCGTGTC TTACCGGGTT GGACTCAAGA CGATAGTTAC
7081 CGGATAAGGC GCAGCGGTCG GGCTGAACGG GGGGTTCGTG CACACAGCCC AGCTTGGAGC
7141 GAACGACCTA CACCGAACTG AGATACCTAC AGCGTGAGCT ATGAGAAAGC GCCACGCTTC
```

FIG. 9 (cont.)

```
7201 CCGAAGGGAG AAAGGCGGAC AGGTATCCGG TAAGCGGCAG GGTCGGAACA GGAGAGCGCA
7261 CGAGGGAGCT TCCAGGGGGA AACGCCTGGT ATCTTTATAG TCCTGTCGGG TTTCGCCACC
7321 TCTGACTTGA GCGTCGATTT TTGTGATGCT CGTCAGGGGG GCGGAGCCTA TGGAAAAACG
7381 CCAGCAACGC GGCCTTTTTA CGGTTCCTGG CCTTTTGCTG GCCTTTTGCT CACATGTTCT
7441 TTCCTGCGTT ATCCCCTGAT TCTGTGGATA ACCGTATTAC CGCCTTTGAG TGAGCTGATA
7501 CCGCTCGCCG CAGCCGAACG ACCGAGCGCA GCGAGTCAGT GAGCGAGGAA GCGGAAGAGC
7561 GCCTGATGCG GTATTTTCTC CTTACGCATC TGTGCGGTAT TTCACACCGC ATATATGGTG
7621 CACTCTCAGT ACAATCTGCT CTGATGCCGC ATAGTTAAGC CAGTATACAC TCCGCTATCG
7681 CTACGTGACT GGGTCATGGC TGCGCCCCGA CACCCGCCAA CACCCGCTGA CGCGCCCTGA
7741 CGGGCTTGTC TGCTCCCGGC ATCCGCTTAC AGACAAGCTG TGACCGTCTC CGGGAGCTGC
7801 ATGTGTCAGA GGTTTTCACC GTCATCACCG AAACGCGCGA GGCAGCTGCG GTAAAGCTCA
7861 TCAGCGTGGT CGTGCAGCGA TTCACAGATG TCTGCCTGTT CATCCGCGTC CAGCTCGTTG
7921 AGTTTCTCCA GAAGCGTTAA TGTCTGGCTT CTGATAAAGC GGGCCATGTT AAGGGCGGTT
7981 TTTTCCTGTT TGGTCACTGA TGCCTCCGTG TAAGGGGGAT TTCTGTTCAT GGGGGTAATG
8041 ATACCGATGA AACGAGAGAG GATGCTCACG ATACGGGTTA CTGATGATGA ACATGCCCGG
8101 TTACTGGAAC GTTGTGAGGG TAAACAACTG GCGGTATGGA TGCGGCGGGA CCAGAGAAAA
8161 ATCACTCAGG GTCAATGCCA GCGCTTCGTT AATACAGATG TAGGTGTTCC ACAGGGTAGC
8221 CAGCAGCATC CTGCGATGCA GATCCGGAAC ATAATGGTGC AGGGCGCTGA CTTCCGCGTT
8281 TCCAGACTTT ACGAAACACG GAAACCGAAG ACCATTCATG TTGTTGCTCA GGTCGCAGAC
8341 GTTTTGCAGC AGCAGTCGCT TCACGTTCGC TCGCGTATCG GTGATTCATT CTGCTAACCA
8401 GTAAGGCAAC CCCGCCAGCC TAGCCGGGTC CTCAACGACA GGAGCACGAT CATGCGCACC
8461 CGTGGCCAGG ACCCAACGCT GCCCGAAATT
```

FIG. 9 (cont.)

SEQ ID NO: 17

```
   1 CCGACACCAT CGAATGGTGC AAAACCTTTC GCGGTATGGC ATGATAGCGC CCGGAAGAGA
  61 GTCAATTCAG GGTGGTGAAT GTGAAACCAG TAACGTTATA CGATGTCGCA GAGTATGCCG
 121 GTGTCTCTTA TCAGACCGTT TCCCGCGTGG TGAACCAGGC CAGCCACGTT TCTGCGAAAA
 181 CGCGGGAAAA AGTGGAAGCG GCGATGGCGG AGCTGAATTA CATTCCCAAC CGCGTGGCAC
 241 AACAACTGGC GGGCAAACAG TCGTTGCTGA TTGGCGTTGC CACCTCCAGT CTGGCCCTGC
 301 ACGCGCCGTC GCAAATTGTC GCGGCGATTA AATCTCGCGC CGATCAACTG GGTGCCAGCG
 361 TGGTGGTGTC GATGGTAGAA CGAAGCGGCG TCGAAGCCTG TAAAGCGGCG GTGCACAATC
 421 TTCTCGCGCA ACGCGTCAGT GGGCTGATCA TTAACTATCC GCTGGATGAC CAGGATGCCA
 481 TTGCTGTGGA AGCTGCCTGC ACTAATGTTC GGCGTTATT TCTTGATGTC TCTGACCAGA
 541 CACCCATCAA CAGTATTATT TTCTCCCATG AAGACGGTAC GCGACTGGGC GTGGAGCATC
 601 TGGTCGCATT GGGTCACCAG CAAATCGCGC TGTTAGCGGG CCCATTAAGT TCTGTCTCGG
 661 CGCGTCTGCG TCTGGCTGGC TGGCATAAAT ATCTCACTCG CAATCAAATT CAGCCGATAG
 721 CGGAACGGGA AGGCGACTGG AGTGCCATGT CCGGTTTTCA ACAAACCATG CAAATGCTGA
 781 ATGAGGGCAT CGTTCCCACT GCGATGCTGG TTGCCAACGA TCAGATGGCG CTGGGCGCAA
 841 TGCGCGCCAT TACCGAGTCC GGGCTGCGCG TTGGTGCGGA TATCTCGGTA GTGGGATACG
 901 ACGATACCGA AGACAGCTCA TGTTATATCC CGCCGTTAAC CACCATCAAA CAGGATTTTC
 961 GCCTGCTGGG GCAAACCAGC GTGGACCGCT TGCTGCAACT CTCTCAGGGC CAGGCGGTGA
1021 AGGGCAATCA GCTGTTGCCC GTCTCACTGG TGAAAAGAAA AACCACCCTG GCGCCCAATA
1081 CGCAAACCGC CTCTCCCCGC GCGTTGGCCG ATTCATTAAT GCAGCTGGCA CGACAGGTTT
1141 CCCGACTGGA AAGCGGGCAG TGAGCGCAAC GCAATTAATG TAAGTTAGCT CACTCATTAG
1201 GCACAATTCT CATGTTTGAC AGCTTATCAT CGACTGCACG GTGCACCAAT GCTTCTGGCG
1261 TCAGGCAGCC ATCGGAAGCT GTGGTATGGC TGTGCAGGTC GTAAATCACT GCATAATTCG
1321 TGTCGCTCAA GGCGCACTCC CGTTCTGGAT AATGTTTTTT GCGCCGACAT CATAACGGTT
1381 CTGGCAAATA TTCTGAAATG AGCTGTTGAC AATTAATCAT CGGCTCGTAT AATGTGTGGA
1441 ATTGTGAGCG GATAACAATT TCACACAGGA AACAGCCAGT CCGTTTAGGT GTTTTCACGA
1501 GCACTTCACC AACAAGGACC ATAGCATATG AAAATCGAAG AAGGTAAACT GGTAATCTGG
1561 ATTAACGGCG ATAAAGGCTA TAACGGTCTC GCTGAAGTCG GTAAGAAATT CGAGAAAGAT
1621 ACCGGAATTA AAGTCACCGT TGAGCATCCG GATAAACTGG AAGAGAAATT CCCACAGGTT
1681 GCGGCAACTG GCGATGGCCC TGACATTATC TTCTGGGCAC ACGACCGCTT TGGTGGCTAC
1741 GCTCAATCTG GCCTGTTGGC TGAAATCACC CCGGACAAAG CGTTCCAGGA CAAGCTGTAT
1801 CCGTTTACCT GGGATGCCGT ACGTTACAAC GGCAAGCTGA TTGCTTACCC GATCGCTGTT
1861 GAAGCGTTAT CGCTGATTTA TAACAAAGAT CTGCTGCCGA ACCCGCCAAA AACCTGGGAA
1921 GAGATCCCGG CGCTGGATAA AGAACTGAAA GCGAAGGTA AGAGCGCGCT GATGTTCAAC
1981 CTGCAAGAAC CGTACTTCAC CTGGCCGCTG ATTGCTGCTG ACGGGGGTTA TGCGTTCAAG
2041 TATGAAAACG GCAAGTACGA CATTAAAGAC GTGGGCGTGG ATAACGCTGG CGCGAAAGCG
2101 GGTCTGACCT TCCTGGTTGA CCTGATTAAA AACAAACACA TGAATGCAGA CACCGATTAC
2161 TCCATCGCAG AAGCTGCCTT TAATAAAGGC GAAACAGCGA TGACCATCAA CGGCCCGTGG
2221 GCATGGTCCA ACATCGACAC CAGCAAAGTG AATTATGGTG TAACGGTACT GCCGACCTTC
2281 AAGGGTCAAC CATCCAAACC GTTCGTTGGC GTGCTGAGCG CAGGTATTAA CGCCGCCAGT
2341 CCGAACAAAG AGCTGGCAAA AGAGTTCCTC GAAAACTATC TGCTGACTGA TGAAGGTCTG
2401 GAAGCGGTTA ATAAAGACAA ACCGCTGGGT GCCGTAGCGC TGAAGTCTTA CGAGGAAGAG
2461 TTGGCGAAAG ATCCACGTAT TGCCGCCACT ATGGAAAACG CCCAGAAAGG TGAAATCATG
2521 CCGAACATCC CGCAGATGTC CGCTTTCTGG TATGCCGTGC GTACTGCGGT GATCAACGCC
2581 GCCAGCGGTC GTCAGACTGT CGATGCCGCC CTGGCCGCCG CGCAGACTGC CGCCGCCGCC
2641 GCCATGGCTT TGTTGGAACG CATCTTAGCG AGAGACAACC TCATCACGGC GCTCAAACGG
2701 GTCGAAGCCA ACCAAGGAGC ACCGGGAATC GACGGAGTAT CAACCGATCA ACTCCGTGAT
2761 TACATCCGCG CTCACTGGAG CACGATCCAC GCCCAACTCT TGGCGGGAAC CTACCGGCCG
2821 GCGCCTGTCC GCAGGGTCGA AATCCCGAAA CCGGGCGGCG GCACACGGCA GCTAGGCATT
2881 CCCACCGTGG TGGACCGGCT GATCCAACAA GCCATTCTTC AAGAACTCAC ACCCATTTTC
2941 GATCCAGACT TCTCCTCTTC CAGCTTCGGA TTCCGTCCGG CCGCAACGC CCACGATGCC
3001 GTGCGGCAAG CGCAAGGCTA CATCCAGGAA GGGTATCGGT ACGTGGTCGA CATGGACCTG
3061 GAAAAGTTCT TTGATCGGGT CAACCATGAC ATCTTGATGA GTCGGGTGGC CCGAAAAGTC
3121 AAGGATAAAC GCGTGCTGAA ACTGATCCGT GCCTACCTGC AAGCCGGCGT TATGATCGAA
3181 GGGGTGAAGG TGCAGACGGA GGAAGGGACG CCGCAAGGCG GCCCCTCAG CCCCCTGCTG
3241 GCGAACATCC TTCTCGACGA TTTAGACAAG GAATTGGAGA AGCGAGGATT GAAATTCTGC
3301 CGTTACGCAG ATGACTGCAA CATCTATGTG AAAAGTCTGC GGCAGGACA ACGGGTGAAA
3361 CAAAGCATCC AACGGTTCTT GGAGAAACG CTCAAACTCA AGTAAACGA GGAGAAAAGT
3421 GCGGTGGACC GCCCGTGGAA ACGGGCCTTT CTGGGGTTTA GCTTCACACC GGAACGAAAA
3481 GCGCGAATCC GGCTCGCCCC AAGGTCGATT CAACGTCTGA AACAGCGGAT TCGACAGCTG
```

FIG. 10

```
3541 ACCAACCCAA ACTGGAGCAT ATCGATGCCA GAACGAATTC ATCGCGTCAA TCAATACGTC
3601 ATGGGATGGA TCGGGTATTT TCGGCTCGTC GAAACCCCGT CTGTCCTTCA GACCATCGAA
3661 GGATGGATTC GGAGGAGGCT TCGACTCTGT CAATGGCTTC AATGGAAACG GGTCAGAACC
3721 AGAATCCGTG AGTTAAGAGC GCTGGGGCTG AAAGAGACAG CGGTGATGGA GATCGCCAAT
3781 ACCCGAAAAG GAGCTTGGCG AACAACGAAA ACGCCGCAAC TCCACCAGGC CCTGGGCAAG
3841 ACCTACTGGA CCGCTCAAGG GCTCAAGAGT TTGACGCAAC GATATTTCGA ACTCCGTCAA
3901 GGTTGACTGC AGGCAAGCTT GGCACTGGCC GTCGTTTTAC AACGTCGTGA CTGGGAAAAC
3961 CCTGGCGTTA CCCAACTTAA TCGCCTTGCA GCACATCCCC CTTTCGCCAG CTGGCGTAAT
4021 AGCGAAGAGG CCCGCACCGA TCGCCCTTCC CAACAGTTGC GCAGCCTGAA TGGCGAATGG
4081 CAGCTTGGCT GTTTTGGCGG ATGAGATAAG ATTTTCAGCC TGATACAGAT TAAATCAGAA
4141 CGCAGAAGCG GTCTGATAAA ACAGAATTTG CCTGGCGGCA GTAGCGCGGT GGTCCCACCT
4201 GACCCCATGC CGAACTCAGA AGTGAAACGC CGTAGCGCCG ATGGTAGTGT GGGGTCTCCC
4261 CATGCGAGAG TAGGGAACTG CCAGGCATCA AATAAAACGA AAGGCTCAGT CGAAAGACTG
4321 GGCCTTTCGT TTTATCTGTT GTTTGTCGGT GAACGCTCTC CTGAGTAGGA CAAATCCGCC
4381 GGGAGCGGAT TTGAACGTTG CGAAGCAACG GCCCGGAGGG TGGCGGGCAG GACGCCCGCC
4441 ATAAACTGCC AGGCATCAAA TTAAGCAGAA GGCCATCCTG ACGGATGCC TTTTTGCGTT
4501 TCTACAAACT CTTTTTGTTT ATTTTTCTAA ATACATTCAA ATATGTATCC GCTCATGAGA
4561 CAATAACCCT GATAAATGCT TCAATAATAT TGAAAAGGA AGAGTATGAG TATTCAACAT
4621 TTCCGTGTCG CCCTTATTCC CTTTTTTGCG GCATTTTGCC TTCCTGTTTT TGCTCACCCA
4681 GAAACGCTGG TGAAAGTAAA AGATGCTGAA GATCAGTTGG GTGCACGAGT GGGTTACATC
4741 GAACTGGATC TCAACAGCGG TAAGATCCTT GAGAGTTTTC GCCCCGAAGA ACGTTCTCCA
4801 ATGATGAGCA CTTTTAAAGT TCTGCTATGT GGCGCGGTAT TATCCCGTGT TGACGCCGGG
4861 CAAGAGCAAC TCGGTCGCCG CATACACTAT TCTCAGAATG ACTTGGTTGA GTACTCACCA
4921 GTCACAGAAA AGCATCTTAC GGATGGCATG ACAGTAAGAG AATTATGCAG TGCTGCCATA
4981 ACCATGAGTG ATAACACTGC GGCCAACTTA CTTCTGACAA CGATCGGAGG ACCGAAGGAG
5041 CTAACCGCTT TTTTGCACAA CATGGGGGAT CATGTAACTC GCCTTGATCG TTGGGAACCG
5101 GAGCTGAATG AAGCCATACC AAACGACGAG CGTGACACCA CGATGCCTGT AGCAATGGCA
5161 ACAACGTTGC GCAAACTATT AACTGGCGAA CTACTTACTC TAGCTTCCCG GCAACAATTA
5221 ATAGACTGGA TGGAGGCGGA TAAAGTTGCA GGACCACTTC TGCGCTCGGC CCTTCCGGCT
5281 GGCTGGTTTA TTGCTGATAA ATCTGGAGCC GGTGAGCGTG GGTCTCGCGG TATCATTGCA
5341 GCACTGGGGC CAGATGGTAA GCCCTCCCGT ATCGTAGTTA TCTACACGAC GGGGAGTCAG
5401 GCAACTATGG ATGAACGAAA TAGACAGATC GCTGAGATAG GTGCCTCACT GATTAAGCAT
5461 TGGTAACTGT CAGACCAAGT TTACTCATAT ATACTTTAGA TTGATTTACC CCGGTTGATA
5521 ATCAGAAAAG CCCCAAAAAC AGGAAGATTG TATAAGCAAA TATTTAAATT GTAAACGTTA
5581 ATATTTTGTT AAAATTCGCG TTAAATTTTT GTTAAATCAG CTCATTTTTT AACCAATAGG
5641 CCGAAATCGG CAAAATCCCT TATAAATCAA AAGAATAGAC CGAGATAGGG TTGAGTGTTG
5701 TTCCAGTTTG GAACAAGAGT CCACTATTAA AGAACGTGGA CTCCAACGTC AAAGGGCGAA
5761 AAACCGTCTA TCAGGGCGAT GGCCCACTAC GTGAACCATC ACCCAAATCA AGTTTTTTGG
5821 GGTCGAGGTG CCGTAAAGCA CTAAATCGGA ACCCTAAAGG GAGCCCCCGA TTTAGAGCTT
5881 GACGGGGAAA GCCGGCGAAC GTGGCGAGAA AGGAAGGGAA GAAAGCGAAA GGAGCGGGCG
5941 CTAGGGCGCT GGCAAGTGTA GCGGTCACGC TGCGCGTAAC CACCACACCC GCCGCGCTTA
6001 ATGCGCCGCT ACAGGGCGCG TAAAAGGATC TAGGTGAAGA TCCTTTTTGA TAATCTCATG
6061 ACCAAAATCC CTTAACGTGA GTTTTCGTTC CACTGAGCGT CAGACCCCGT AGAAAAGATC
6121 AAAGGATCTT CTTGAGATCC TTTTTTTCTG CGCGTAATCT GCTGCTTGCA AACAAAAAAA
6181 CCACCGCTAC CAGCGGTGGT TTGTTTGCCG GATCAAGAGC TACCAACTCT TTTTCCGAAG
6241 GTAACTGGCT TCAGCAGAGC GCAGATACCA AATACTGTCC TTCTAGTGTA GCCGTAGTTA
6301 GGCCACCACT TCAAGAACTC TGTAGCACCG CCTACATACC TCGCTCTGCT AATCCTGTTA
6361 CCAGTGGCTG CTGCCAGTGG CGATAAGTCG TGTCTTACCG GGTTGGACTC AAGACGATAG
6421 TTACCGGATA AGGCGCAGCG GTCGGGCTGA ACGGGGGGTT CGTGCACACA GCCCAGCTTG
6481 GAGCGAACGA CCTACACCGA ACTGAGATAC CTACAGCGTG AGCTATGAGA AAGCGCCACG
6541 CTTCCCGAAG GGAGAAAGGC GGACAGGTAT CCGGTAAGCG GCAGGGTCGG AACAGGAGAG
6601 CGCACGAGGG AGCTTCCAGG GGGAAACGCC TGGTATCTTT ATAGTCCTGT CGGGTTTCGC
6661 CACCTCTGAC TTGAGCGTCG ATTTTTGTGA TGCTCGTCAG GGGGCGGAG CCTATGGAAA
6721 AACGCCAGCA ACGCGGCCTT TTTACGGTTC CTGGCCTTTT GCTGGCCTTT TGCTCACATG
6781 TTCTTTCCTG CGTTATCCCC TGATTCTGTG ATAACCGTA TTACCGCCTT TGAGTGAGCT
6841 GATACCGCTC GCCGCAGCCG AACGACCGAG CGCAGCGAGT CAGTGAGCGA GGAAGCGGAA
6901 GAGCGCCTGA TGCGGTATTT TCTCCTTACG CATCTGTGCG GTATTTCACA CCGCATATAT
6961 GGTGCACTCT CAGTACAATC TGCTCTGATG CCGCATAGTT AAGCCAGTAT ACACTCCGCT
7021 ATCGCTACGT GACTGGGTCA TGGCTGCGCC CCGACACCCG CCAACACCCG CTGACGCGCC
7081 CTGACGGGCT TGTCTGCTCC CGGCATCCGC TTACAGACAA GCTGTGACCG TCTCCGGGAG
7141 CTGCATGTGT CAGAGGTTTT CACCGTCATC ACCGAAACGC GCGAGGCAGC TGCGGTAAAG
```

FIG. 10 (cont.)

```
7201 CTCATCAGCG TGGTCGTGCA GCGATTCACA GATGTCTGCC TGTTCATCCG CGTCCAGCTC
7261 GTTGAGTTTC TCCAGAAGCG TTAATGTCTG GCTTCTGATA AAGCGGGCCA TGTTAAGGGC
7321 GGTTTTTTCC TGTTTGGTCA CTGATGCCTC CGTGTAAGGG GGATTTCTGT TCATGGGGGT
7381 AATGATACCG ATGAAACGAG AGAGGATGCT CACGATACGG GTTACTGATG ATGAACATGC
7441 CCGGTTACTG GAACGTTGTG AGGGTAAACA ACTGGCGGTA TGGATGCGGC GGGACCAGAG
7501 AAAAATCACT CAGGGTCAAT GCCAGCGCTT CGTTAATACA GATGTAGGTG TTCCACAGGG
7561 TAGCCAGCAG CATCCTGCGA TGCAGATCCG GAACATAATG GTGCAGGGCG CTGACTTCCG
7621 CGTTTCCAGA CTTTACGAAA CACGGAAACC GAAGACCATT CATGTTGTTG CTCAGGTCGC
7681 AGACGTTTTG CAGCAGCAGT CGCTTCACGT TCGCTCGCGT ATCGGTGATT CATTCTGCTA
7741 ACCAGTAAGG CAACCCCGCC AGCCTAGCCG GGTCCTCAAC GACAGGAGCA CGATCATGCG
7801 CACCCGTGGC CAGGACCCAA CGCTGCCCGA AATT
```

FIG. 10 (cont.)

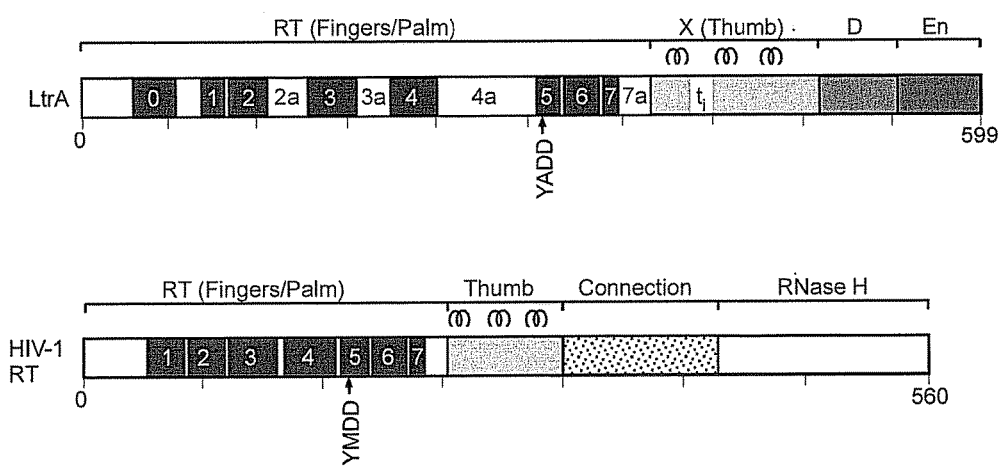
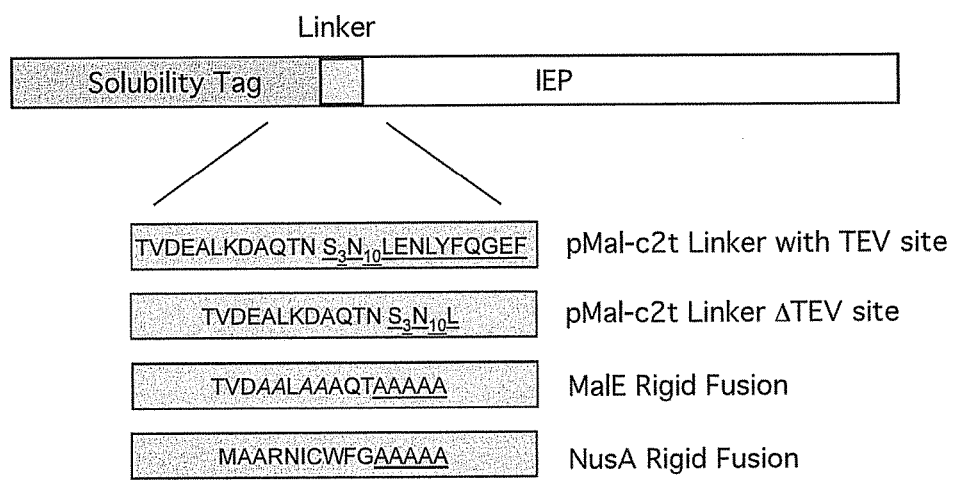
FIG. 12

SEQ ID NO: 21

5'GAATACAAGCTTGGGCGTGTCTCAAAATCTCTGATGTTACATTGCACAAGATAA
AAATATATCATCATGAACAATAAAACTGTCTGCTTACATAAACAGTAATACAAG
GGGTGTTATGAGCCATATTCAACGGGAAACGTCTTGCTCGAGGCCGCGATTAAAT
TCCAACATGGATGCTGATTTATATGGGTATAAATGGGCTCGCGATAATGTCGGGC
AATCAGGTGCGACAATCTATCGATTGTATGGGAAGCCCGATGCGCCAGAGTTGTT
TCTGAAACATGGCAAAGGTAGCGTTGCCAATGATGTTACAGATGAGATGGTCAG
ACTAAACTGGCTGACGGAATTTATGCCTCTTCCGACCATCAAGCATTTTATCCGT
ACTCCTGATGATGCATGGTTACTCACCACTGCGATCCCCGGGAAAACAGCATTCC
AGGTATTAGAAGAATATCCTGAGTCAGGTGAAAATATTGTTGATGCGCTGGCAGT
GTTCCTGCGCCGGTTGCATTCGATTCCTGTTTGTAATTGTCCTTTTAACAGCGATC
GCGTATTTCGTCTCGCTCAGGCGCAATCACGAATGAATAACGGTTTGGTTGATGC
GAGTGATTTTGATGACGAGCGTAATGGCTGGCCTGTTGAACAAGTCTGGAAAGA
AATGCATAAGCTTTTGCCATTCTCACCGGATTCAGTCGTCACTCATGGTGATTTCT
CACTTGATAACCTTATTTTTGACGAGGGGAAATTAATAGGTTGTATTGATGTTGG
ACGAGTCGGAATCGCAGACCGATACCAGGATCTTGCCATCCTATGGAACTGCCTC
GGTGAGTTTTCTCCTTCATTACAGAAACGGCTTTTTCAAAAATATGGTATTGATA
ATCCTGATATGAATAAATTGCAGTTTCATTTGATGCTCGATGAGTTTTTCTAATCA
GAATTGGTTAATTGGTTGTAACACTGGCAGAGCATTACGCTGACTTGACGGGACG
GCGGCTTTGTTGAATAAATCGAACTTTTGCTGAGTTGAAGGATCAGATCACGCAT
CTTCCCGACAACGCAGACCGTTCCGTGGCAAAGCAAAAGTTCAAAATCACCAAC
TGGTCCACCTACAACAAAGCTCTCATCAACCGTGGCGACTCTAGAGGATCCCCGG
GCGAGCTCCCAAAAAAAAAAAAAAAAAAAAAAAAAAAAAAAACCGAATT-3'

FIG. 15

SEQ ID NO: 38

MNKEILAVVEAVSNEKALPREKIFEALESALATATKKKYEQEIDVRVQIDRKSGDFD
TFRRWLVVDEVTQPTKEITLEAARYEDESLNLGDYVEDQIESVTFDRITTQTAKQVIV
QKVREAERAMVVDQFREHEGEIITGVVKKVNRDNISLDLGNNAEAVILREDMLPRE
NFRPGDRVRGVLYSVRPEARGAQLFVTRSKPEMLIELFRIEVPEIGEEVIEIKAAARDP
GSRAKIAVKTNDKRIDPVGACVGMRGARVQAVSTELGGERIDIVLWDDNPAQFVIN
AMAPADVASIVVDEDKHTMDIAVEAGNLAQAIGRNGQNVRLASQLSGWELNVMTV
DDLQAKHQAEAHAAIDTFTKYLDIDEDFATVLVEEGFSTLEELAYVPMKELLEIEGL
DEPTVEALRERAKNALATIAQAQEESLGDNKPADDLLNLEGVDRDLAFKLAARGVC
TLEDLAEQGIDDLADIEGLTDEKAGALIMAARNICWFG

FIG. 18

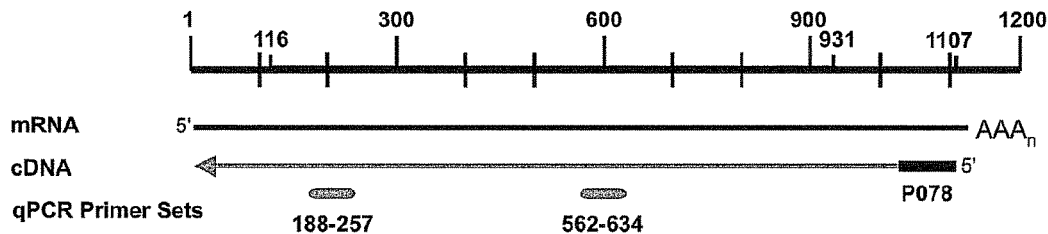
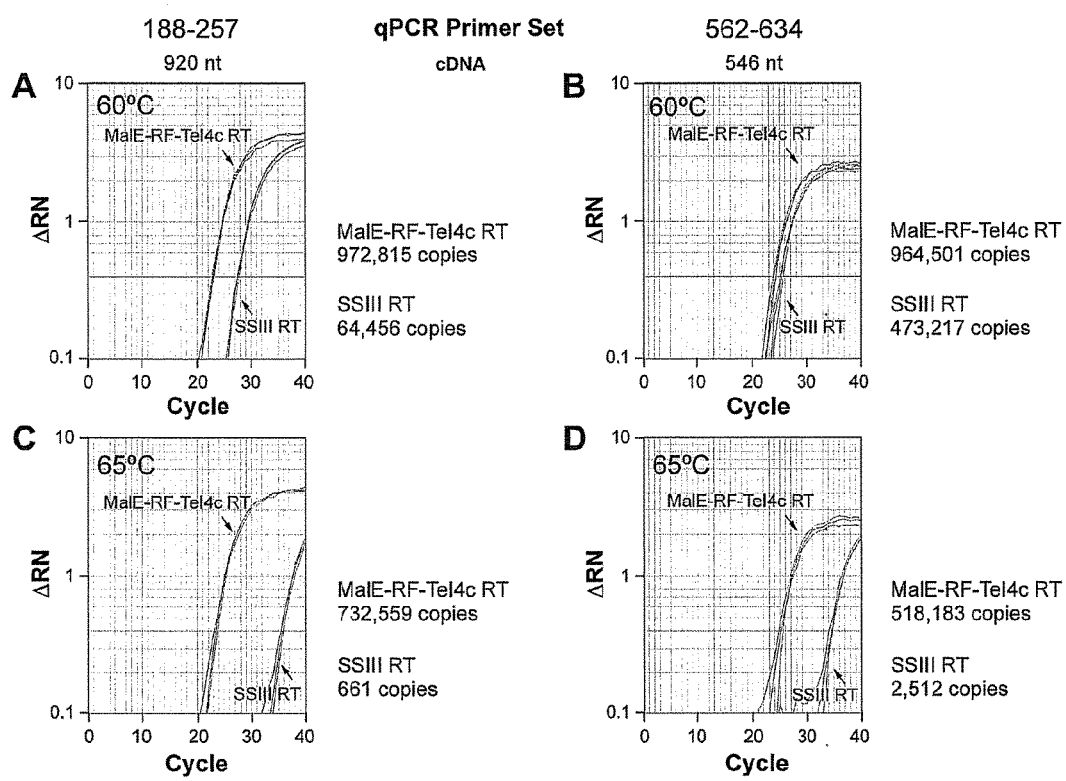
FIG. 17

STABILIZED REVERSE TRANSCRIPTASE FUSION PROTEINS

CONTINUING APPLICATION DATA

This application is the U.S. national phase entry of PCT/US10/26165 with an international filing date of Mar. 4, 2010, which claims the benefit of U.S. Provisional Application Ser. No. 61/157,332, filed Mar. 4, 2009, which is incorporated by reference herein.

GOVERNMENT FUNDING

This invention was made with government support under grant number RO1 GM037949 awarded by the National Institutes of Health. The government has certain rights in this invention.

BACKGROUND OF THE INVENTION

Reverse transcription polymerase chain reaction, abbreviated as RT-PCR, is a well known technique for amplifying RNA. In RT-PCR, an RNA strand is reverse transcribed into complementary DNA (cDNA), which is then amplified using DNA polymerase in the polymerase chain reaction. In the first step of this process, cDNA is made from an RNA template using deoxyribonucleotide phosphates and reverse transcriptase together with a DNA primer.

Synthesis of cDNA from the RNA template can be hindered by RNA secondary and tertiary structures, which consist of helices and various other kinds of kinks in the RNA strand. RNA secondary and tertiary structure can be decreased by carrying out the reaction at a higher temperature (e.g., above 50° C.) or by adding denaturing additives. However, the addition of denaturing additives is undesirable because it often reduces reverse transcriptase activity. Higher temperatures also provide the advantage of increasing the specificity of DNA synthesis by decreasing non-specific primer binding. Unfortunately, only a limited number of reverse transcriptases capable of operating at high temperature are currently available, and these exhibit relatively low fidelity DNA polymerization. For example, commercially available Avian Myeloblastosis Virus reverse transcriptase includes RNase H activity and can function at 37° C., but has a fidelity of only about $1.7\times10^{-4}$. RNase H activity competes with the DNA polymerase activity and the primer binding site and, therefore, cDNA yield is lower. Accordingly, there is a need for reverse transcriptase enzymes that are able to carry out reverse transcription at higher temperatures, including those that have high fidelity and processivity. Such enzymes are beneficial because higher temperatures decrease obstructing RNA secondary and tertiary structure and increase the specificity of reverse transcription by allowing the use of longer and more specific primers.

SUMMARY OF THE INVENTION

In one aspect, the invention provides a stabilized reverse transcriptase (RT) fusion protein that includes a thermostable reverse transcriptase connected to a stabilizer protein. In one embodiment of the stabilized reverse transcriptase fusion protein, the thermostable reverse transcriptase is a bacterial reverse transcriptase. In a further embodiment, the bacterial reverse transcriptase is a group II intron-derived reverse transcriptase. Examples of thermostable bacterial reverse transcriptases include *Thermosynechococcus elongatus* reverse transcriptase and *Geobacillus stearothermophilus* reverse transcriptase. In another embodiment, the thermostable reverse transcriptase exhibits high fidelity cDNA synthesis. In yet another embodiment, the thermostable reverse transcriptase includes a polypeptide with an amino acid sequence identity that is substantially similar to a sequence selected from the group consisting of SEQ ID NO: 1, SEQ ID NO: 2, SEQ ID NO: 3, SEQ ID NO: 4, or SEQ ID NO: 5.

The stabilized reverse transcriptase fusion protein includes a stabilizer protein that, when linked to the reverse transcriptase, enhances the shelf life and/or the thermal stability and/or the solubility of the thermostable reverse transcriptase. In certain embodiments, the stabilizer protein is an affinity protein or a solubility-enhancing protein (e.g., a maltose binding protein or N-utilization substance A protein). In additional embodiments, the stabilizer protein is modified by replacing certain charged amino acids with uncharged amino acids.

The stabilized reverse transcriptase fusion protein can also include a linker peptide that connects the thermostable reverse transcriptase to the stabilizer protein. In some embodiments, this linker peptide is a non-cleavable linker, while in other embodiments it is a non-cleavable rigid linker. In some embodiments, the linker peptide consists of 1 to 20 amino acids, while in other embodiments the linker peptide consists of 1 to 5 or 3 to 5 amino acids. For example, a rigid non-cleavable linker peptide can include 5 alanine amino acids.

In additional embodiments, the stabilized reverse transcriptase fusion protein has an amino acid sequence that includes a polypeptide with an amino acid sequence identity that is substantially similar to a sequence selected from the group consisting of SEQ ID NO: 6, SEQ ID NO: 7, SEQ ID NO: 8, SEQ ID NO: 9, or SEQ ID NO: 10. In some embodiments, the stabilized reverse transcriptase fusion protein is a high fidelity reverse transcriptase capable of carrying out reverse transcription with an error frequency of $2.0\times10^{-5}$ or less at a temperature from about 45° to about 65° C. In further embodiments, the stabilized reverse transcriptase fusion protein is capable of carrying out substantial levels of reverse transcription at temperatures up to about 81° C.

Another aspect of the invention provides a method for preparing a cDNA from an RNA molecule that includes the steps of: (a) adding a primer nucleotide sequence to an RNA molecule and (b) incubating the RNA molecule in the presence of one or more modified or unmodified deoxy or dideoxyribonucleoside triphosphates and a stabilized reverse transcriptase fusion protein that includes a thermostable reverse transcriptase connected to a stabilizer protein under conditions sufficient to synthesize a cDNA molecule complementary to all or a portion of the RNA molecule. In particular embodiments, the thermostable reverse transcriptase is connected to the stabilizer protein by a linker peptide (e.g., a non-cleavable or rigid non-cleavable linker peptide). Preferably, the reverse transcription is performed within a temperature range where RNA includes a substantially decreased amount of obstructing stable secondary or tertiary structure. Embodiments of this method include ones in which the thermostable reverse transcriptase is a group II intron-derived reverse transcriptase. In further embodiments of the method, the thermostable reverse transcriptase includes a polypeptide with an amino acid sequence identity that is substantially similar to a sequence selected from the group consisting of SEQ ID NO: 1, SEQ ID NO: 2, SEQ ID NO: 3, SEQ ID NO: 4, or SEQ ID NO: 5, a non-cleavable linker consists of 1 to 20 amino acids, and the stabilizer protein is an affinity protein or a solubility-enhancing protein. In yet further embodiments of the method, the reverse transcription is performed with an error frequency of 2.0× $10^{-5}$ or less at a temperature from about 45° to about 65° C.

Another aspect of the invention provides a DNA expression vector for producing a stabilized reverse transcriptase fusion protein that includes a nucleic acid that encodes a polypeptide with an amino acid sequence identity that is substantially similar to a sequence selected from the group consisting of SEQ ID NO: 6, SEQ ID NO: 7, SEQ ID NO: 8, SEQ ID NO: 9, or SEQ ID NO: 10.

Another aspect of the invention provides a method of producing a stabilized reverse transcriptase fusion protein that includes the steps of: (a) culturing a host cell that includes a DNA expression vector for producing a stabilized reverse transcriptase fusion protein that includes a nucleic acid that encodes a polypeptide with an amino acid sequence identity that is substantially similar to a sequence selected from the group consisting of SEQ ID NO: 6, SEQ ID NO: 7, SEQ ID NO: 8, SEQ ID NO: 9, or SEQ ID NO: 10; (b) expressing the stabilized reverse transcriptase fusion protein encoded by the DNA expression vector; and (c) isolating the stabilized reverse transcriptase fusion protein from the host cell.

The stabilized reverse transcriptase fusion protein can facilitate cDNA synthesis at higher temperature, and/or with higher processivity, and/or allow the use of longer, more stable, primers that increase the specificity (i.e., fidelity) of reverse transcription. The stabilized RT fusion protein of the invention can therefore be useful for a number of applications, such as research applications.

It is to be understood that both the foregoing general description and the following detailed description are exemplary and explanatory only and are not restrictive of the invention, as claimed.

BRIEF DESCRIPTION OF THE FIGURES

FIG. 1 is a listing of the amino acid sequence of a reverse transcriptase from *Thermosynechococcus elongatus* bound to a maltose binding protein by a rigid linker (SEQ ID NO: 6). Amino acid residues 1-367 represent the modified maltose binding protein (SEQ ID NO: 11); amino acid residues 368-372 represent the rigid linker (SEQ ID NO: 12); and amino acid residues 373-935 represent the TeI4c ORF (SEQ ID NO: 1).

FIG. 2 is a listing of the amino acid sequence of a reverse transcriptase from *Thermosynechococcus elongatus* bound to a maltose binding protein by a rigid linker (SEQ ID NO: 7). Amino acid residues 1-367 represent the maltose binding protein (SEQ ID NO: 11); amino acid residues 368-372 represent the rigid linker (SEQ ID NO: 12); and amino acid residues 373-935 represent the TeI4f ORF (SEQ ID NO: 2).

FIG. 3 is a listing of the amino acid sequence of a reverse transcriptase from *Thermosynechococcus elongatus* bound to a maltose binding protein by a rigid linker (SEQ ID NO: 8). Amino acid residues 1-367 represent the maltose binding protein (SEQ ID NO: 11); amino acid residues 368-372 represent the rigid linker (SEQ ID NO: 12); and amino acid residues 373-935 represent the TeI4h* ORF (SEQ ID NO: 3).

FIG. 4 is a listing of the amino acid sequence of a reverse transcriptase from *Geobacillus stearothermophilus* bound to a maltose binding protein by a rigid linker (SEQ ID NO: 9). Amino acid residues 1-367 represent the maltose binding protein (SEQ ID NO: 11); amino acid residues 368-372 represent the rigid linker (SEQ ID NO: 12); and amino acid residues 373-1008 represent the *Geobacillus stearothermophilus* GsI1 ORF (SEQ ID NO: 4).

FIG. 5 is a listing of the amino acid sequence of a reverse transcriptase from *Geobacillus stearothermophilus* bound to a maltose binding protein by a rigid linker (SEQ ID NO: 10). Amino acid residues 1-367 represent the maltose binding protein (SEQ ID NO: 11); amino acid residues 368-372 represent the rigid linker (SEQ ID NO: 12); and amino acid residues 373-792 represent the *Geobacillus stearothermophilus* GsI2 ORF (SEQ ID NO: 5).

FIG. 6 is a listing of the nucleotide sequence of the MalE-TeI4c open reading frame (ORF) rigid fusion of reverse transcriptase from *Thermosynechococcus elongatus* in the pMAL expression construct (SEQ ID NO: 13).

FIG. 7 is a listing of the nucleotide sequence of the MalE-TeI4f ORF rigid fusion of a reverse transcriptase from *Thermosynechococcus elongatus* in the pMAL expression construct (SEQ ID NO: 14).

FIG. 8 is a listing of the nucleotide sequence of the MalE-TeI4h* ORF rigid fusion of a reverse transcriptase from *Thermosynechococcus elongatus* in the pMAL expression construct (SEQ ID NO: 15).

FIG. 9 is a listing of the nucleotide sequence of the MalE-GsI1 ORF rigid fusion of a reverse transcriptase from *Geobacillus stearothermophilus* in the pMAL expression construct (SEQ ID NO: 16).

FIG. 10 is a listing of the nucleotide sequence of the MalE-GsI2 ORF rigid fusion of a reverse transcriptase from *Geobacillus stearothermophilus* in the pMAL expression construct (SEQ ID NO: 17).

FIG. 12 shows schematic representations of Group II intron RTs and fusion proteins. Section 12(A) provides comparison of group IT intron-encoded and retroviral RTs. Group II intron RTs exemplified by the LtrA protein encoded by the L1.LtrB intron generally contains four major domains: RT, with conserved sequence blocks RT-1-7; X/thumb; DNA binding (D), and DNA endonuclease (En). The RT and thumb domains of group II intron RTs are homologous to those of retroviral RTs exemplified by HIV-1 RT, but are larger due to an N-terminal extension and insertions upstream (RT-0) and between the conserved RT sequence blocks (e.g., RT-2a, 3a, 4a, and 7a and thumb domain insertion t, in LtrA; Blocker et al., RNA 11, 14-28, 2005). The positions of three α-helices characteristic of the thumb domains of retroviral RTs are shown for both LtrA and HIV-RT. The group II intron RTs used in this work all contain the En domain, except for the GsT2 RT, which lacks the En domain. Section 12(B) shows group II intron RT fusion proteins. Group II intron RTs (IEPs) were expressed with fused N-terminal MalE or NusA solubility tags. Initial constructs contained the MalE solubility tag in expression vector pMalE-c2t fused to the N-terminus of the RT via a flexible linker with a TEV protease cleavage site (underlined). These are shown as TVDEALKDAQTNS$_3$N$_{10}$LENLYFQGEF (SEQ ID NO: 19) and TVDEALKDAQTNS$_3$N$_{10}$L (SEQ ID NO: 44). A variant of these initial constructs tested in FIG. 11 contained the pMalE-c2t linker with the TEV protease cleavage site deleted. Improved constructs used modified MalE or NusA tags fused to the N-terminus of the RT via a rigid linker containing 5 alanine residues (underlined). These are shown as TVDAALAAAQTAAAAA (SEQ ID NO: 20) and MAARNTCWFGAAAAA (SEQ ID NO: 46) The modified MalE tag has charged amino acid residues changed to alanines (italics), and the modified NusA tag is missing the two C-terminal amino acid residues.

FIG. 15 is a listing of the nucleotide sequence of the 1.2-kb kanR RNA template (SEQ ID NO: 21).

FIG. 18 is a listing of the amino acid sequence of the NusA solubility-enhancing protein (SEQ ID NO: 38).

DETAILED DESCRIPTION OF THE INVENTION

Figure 11:
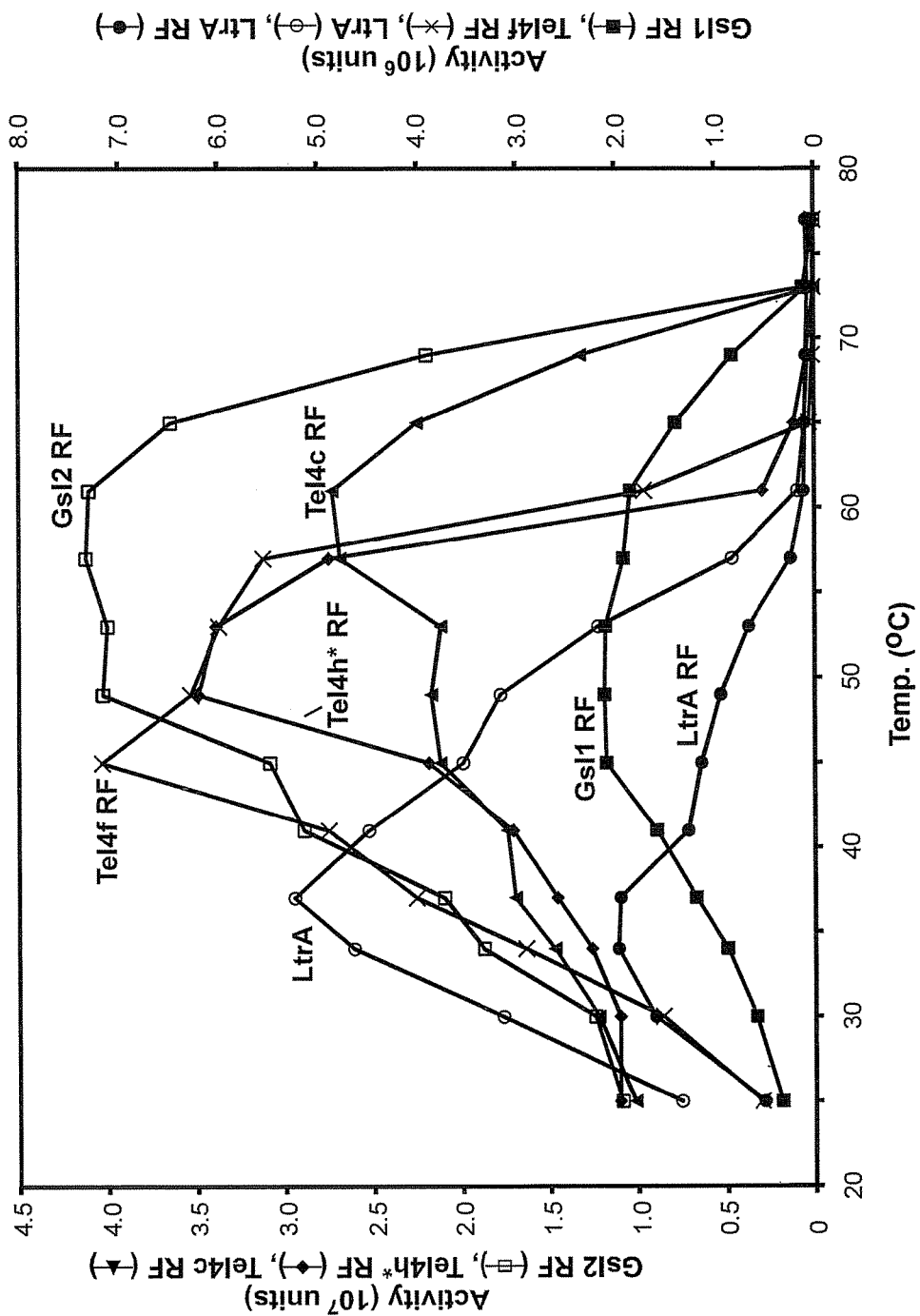
FIG. 11 provides a graph showing the poly(rA)/oligo $(dT)_{42}$ assay of reverse transcriptase (RT) activity at different temperatures. The enzymes assayed were MalE-RF-GsI1, MalE-RF-GsI2, MalE-RF-TeI4c, MalE-RF-TeI4f, MalE-RF-TeI4h*, LtrA, and MalE-RF-LtrA. Reactions were done by incubating the RT (50 nM for TeI4c and 100 nM for all other RTs) with 100 nM poly(rA)/oligo$(dT)_{42}$ and 5 μl [α-$^{32}$P]-dTTP (3,000 Ci/mmol) in 75 mM KCl, 10 mM $MgCl_2$, 20 mM Tris-HCl, pH 7.5, and 1 mM DTT. After preincubating the RT with poly(rA)/oligo$(dT)_{42}$ in the reaction medium for 1 min at the indicated temperature, the reaction was initiated by adding [α-$^{32}$P]-dTTP, incubated for times verified to be within the linear range (90 sec for TeI4c RT and 5 min for all other RTs), and stopped by adding EDTA to a final concentration of 250 mM. The polymerization of [α-$^{32}$P]-dTTP into high-molecular weight material was quantified by spotting the reaction products onto Whatman DE81 chromatography paper (GE Health care Biosciences Corp), washing with 0.3 M NaCl and 0.03 M sodium citrate, and scanning with a PhosphorImager to quantify radioactivity bound to the filter, as described in Materials and Methods. The plot shows radioactivity bound to the filter (PhosphorImager units) as a function of reaction temperature.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

As used herein, "polypeptide" refers to a polymer of amino acids and does not imply a specific length of a polymer of amino acids. Thus, for example, the terms peptide, oligopeptide, protein, antibody, and enzyme are included within the definition of polypeptide. This term also includes polypeptides with post-expression modification, such as glycosylation (e.g., the addition of a saccharide), acetylation, phosphorylation, and the like.

An "isolated" polypeptide or polynucleotide, as used herein, means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The following abbreviations are used throughout the application: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine. Unless otherwise indicated, the term "amino acid" as used herein also includes amino acid derivatives that nonetheless retain the general formula.

A nucleotide consists of a phosphate group linked by a phosphoester bond to a pentose (ribose in RNA, and deoxyribose in DNA) that is linked in turn to an organic base. The monomeric units of a nucleic acid are nucleotides. Naturally occurring DNA and RNA each contain four different nucleotides: nucleotides having adenine, guanine, cytosine and thymine bases are found in naturally occurring DNA, and nucleotides having adenine, guanine, cytosine and uracil bases found in naturally occurring RNA. The bases adenine, guanine, cytosine, thymine, and uracil often are abbreviated A, G, C, T and U, respectively.

Nucleotides include free mono-, di- and triphosphate forms (i.e., where the phosphate group has one, two or three phosphate moieties, respectively). Thus, nucleotides include ribonucleoside triphosphates (e.g., ATP, UTP, CTG and GTP) and deoxyribonucleoside triphosphates (e.g., dATP, dCTP, dITP, dGTP and dTTP), and derivatives thereof. Nucleotides also include dideoxyribonucleoside triphosphates (ddNTPs, including ddATP, ddCTP, ddGTP, ddITP and ddTTP), and derivatives thereof.

"Substantially similar" means that a given nucleic acid or amino acid sequence shares at least 85%, more preferably at least 90%, and even more preferably at least 95% identity with a reference sequence. Furthermore, only sequences describing or encoding proteins in which only conservative substitutions are made in the conserved regions are substantially similar overall. Preferable, substantially similar sequences also retain the distinctive activity of the polypeptide. Substitutions typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

A "promoter," as used herein, refers to a sequence in DNA that mediates the initiation of transcription by an RNA polymerase. Transcriptional promoters may comprise one or more of a number of different sequence elements as follows: 1) sequence elements present at the site of transcription initiation; 2) sequence elements present upstream of the transcription initiation site and; 3) sequence elements downstream of the transcription initiation site. The individual sequence elements function as sites on the DNA, where RNA polymerases and transcription factors that facilitate positioning of RNA polymerases on the DNA bind.

As used herein, the term "polymerase chain reaction" ("PCR") refers to a method for increasing the concentration of a segment of a target sequence in a mixture of genomic DNA without cloning or purification. See for example Bartlett et al., Methods Mol. Biol. 226:3-6 (2003), which provides an overview of PCR and its development. This process for amplifying the target sequence typically consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times to obtain a high concentration of an amplified segment of the desired target sequence. Unless otherwise noted, PCR, as used herein, also includes variants of PCR such as allele-specific PCR, asymmetric PCR, hot-start PCR, ligation-mediated PCR, multiplex-PCR, reverse transcription PCR, or any of the other PCR variants known to those skilled in the art.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

A "fusion protein," as used herein, refers to a protein having at least two heterologous polypeptides covalently linked in which one polypeptide comes from one protein sequence or domain and the other polypeptide comes from a second protein sequence or domain.

Stabilized Reverse Transcriptase Fusion Protein

The invention provides a stabilized reverse transcriptase fusion protein that includes a thermostable reverse transcriptase connected to a stabilizer protein. In many embodiments, the thermostable reverse transcriptase is connected to the stabilizer protein via a linker peptide. However, the thermostable reverse transcriptase and the stabilizer protein can also be directly fused to one another. The polypeptides that comprise the fusion protein are preferably linked N-terminus to C-terminus. However, the reverse transcriptase and the stabilizer protein can be connected together in either order. For example, the two peptide sequences can be connected from the C-terminus to N-terminus or N-terminus to the C-terminus. In some embodiments, a linker peptide is included between the connecting C-terminus and N-terminus of the reverse transcriptase and stabilizer protein.

Attaching a stabilizer protein to the thermostable reverse transcriptase can provide one or more advantages. A stabilized reverse transcriptase fusion protein can have one or more of the following advantages: (a) increased stability at elevated temperatures; (b) higher processivity, (c) increased solubility, and/or (d) higher fidelity. In some embodiments, a reverse transcriptase of the invention may have a plurality of the properties listed above. For example, a stabilized reverse transcriptase fusion protein may have increased thermostability and increased fidelity. The advantages may sometimes derive from one another. For example, by providing increased solubility, the stabilized reverse transcriptase fusion protein can provide a product able to provide increased fidelity of transcription as a result of solubilizing a previously insoluble high fidelity thermostable reverse transcriptase. The use of a stabilizer protein in the fusion protein can also provide other advantages such as increased protein expression and improved protein folding. Inclusion of a linker peptide between the stabilizer protein and the thermostable reverse transcriptase can further enhance these advantages.

The stabilized reverse transcriptase fusion protein includes a thermostable reverse transcriptase and a stabilizer protein, as described herein. The stabilized reverse transcriptase fusion protein can also includes a linker peptide. For example, the stabilized reverse transcriptase fusion protein can have an amino acid sequence as set forth in SEQ ID NO: 6, SEQ ID NO: 7, SEQ ID NO: 8, SEQ ID NO: 9, or SEQ ID NO: 10, shown in FIGS. 1-5, respectively. Alternately, the stabilized reverse transcriptase fusion protein can have an amino acid sequence that is substantially similar to one or more of the sequences as set forth in SEQ ID NO: 6, SEQ ID NO: 7, SEQ ID NO: 8, SEQ ID NO: 9, or SEQ ID NO: 10. A stabilized reverse transcriptase fusion protein amino acid sequence that is "substantially similar" to the fusion proteins provided by sequences 6-10 will share at least 85% identity, more preferably 90% identity and even more preferably 95% identity, and will include only conservative amino acid substitutions in conserved regions.

Thermostable Reverse Transcriptases

The present invention provides a reverse transcriptase fusion protein that includes a thermostable reverse transcriptase. The term "reverse transcriptases" (i.e., RNA-directed DNA polymerases) refers to a group of enzymes having reverse transcriptase activity (i.e., that catalyze synthesis of DNA from an RNA template). In general, such enzymes include, but are not limited to, retroviral reverse transcriptase, retrotransposon reverse transcriptase, and bacterial reverse transcriptases such as group II intron-derived reverse transcriptase, and mutants, variants or derivatives thereof. Examples of bacterial reverse transcriptase include *Lactococcus lactis* reverse transcriptase, *Thermosynechococcus elongatus* reverse transcriptase, or *Geobacillus stearothermophilus* reverse transcriptase. Further bacterial reverse transcriptases are described by Simon et al., Nucleic Acids Research, 36, p. 7219-29 (2008), and Kojima and Kanehisa, Molecular Biology and Evolution, 25, p. 1395-04 (2008) which describe many classes of reverse transcriptases (i.e., retrons, group II introns, and diversity-generating retroelements among others). Reverse transcriptase has been used primarily to transcribe RNA into cDNA, which can then be cloned into a vector for further manipulation or used in various amplification methods such as polymerase chain reaction, nucleic acid sequence-based amplification (NASBA), transcription mediated amplification (TMA), self-sustained sequence replication (3SR), diverse primer extension reactions, 5'RACE, detection of chemical modifications or other techniques that require synthesis of DNA using an RNA template.

The term "thermostable" refers to the ability of an enzyme or protein (e.g., reverse transcriptase) to be resistant to inactivation by heat. Typically such enzymes are obtained from a thermophilic organism (i.e., a thermophile) that has evolved to grow in a high temperature environment. Thermophiles, as used herein, are organisms with an optimum growth temperature of 45° C. or more, and a typical maximum growth temperature of 70° C. or more. In general, a thermostable enzyme is more resistant to heat inactivation than a typical enzyme, such as one from a mesophilic organism. Thus, the nucleic acid synthesis activity of a thermostable reverse transcriptase may be decreased by heat treatment to some extent, but not as much as would occur for a reverse transcriptase from a mesophilic organism. "Thermostable" also refers to an enzyme which is active at temperatures greater than 38° C., preferably between about 38-100° C., and more preferably between about 40-81° C. A particularly preferred temperature range is from about 45° C. to about 65° C.

In some embodiments, a thermostable reverse transcriptase retains at least 50% (e.g., at least 60%, at least 70%, at least 80%, at least 90%, or at least 95%) of its nucleic acid synthetic activity after being heated in a nucleic acid synthesis mixture at 90° C. for 30 seconds. In contrast, typical reverse transcriptases will not work at elevated temperatures, and lose most of their nucleic acid synthetic activity after such heat treatment. Thermostable reverse transcriptases typically also have a higher optimum nucleic acid polymerization temperature.

Some reverse transcriptases are thermostable and therefore remain substantially active at temperatures commonly used in PCR-based nucleic acid synthesis. This provides the advantage of being able to carry out both reverse transcription and DNA amplification in a single reaction environment. Such temperatures vary depending upon reaction parameters, including pH, template and primer nucleotide composition, primer length, and salt concentration. Thermostable reverse transcriptases include *Thermosynechococcus elongatus* (Te) RT, *Geobacillus stearothermophilus* (Gs) RT, modified forms of these RTs, and engineered variants of Avian myoblastosis virus (AMV) RT, Moloney murine leukemia virus (M-MLV) RT, and Human immunodeficiency virus (HIV) RT. A reverse transcriptase obtained from an organism living in an elevated temperature environment (i.e., greater than 37° C.) can be expected to be stable at the living temperature of the organism, and to a reasonable degree above.

A class of reverse transcriptases that is particularly suitable for use in stabilized reverse transcriptase fusion proteins are group II intron-derived reverse transcriptases. A wide variety of group II intron-derived reverse transcriptases are known. See for example the Zimmerly Lab Website for Mobile Group II Introns that describes 105 full length group II intron-derived reverse transcriptases. The use of this website is described by Dai et al., Nucleic Acids Research, 31, p. 424-26 (2003).

In certain embodiments the thermostable reverse transcriptase is one that was encoded by a group II intron. Group II intron RTs typically consist of four conserved domains: RT, which contains seven conserved sequence blocks (RT1-7) characteristic of the fingers and palm regions of retroviral RTs; X, a region required for RNA splicing activity corresponding at least in part to the thumb domain of retroviral RTs; D, a DNA-binding domain involved in DNA target site recognition; and En, a DNA endonuclease domain that cleaves the DNA target site to generate the primer for reverse transcription (FIG. 12A; Blocker et al., RNA 11, 14-28, 2005). The En domain is missing in some group II intron RTs, which instead use nascent strands at DNA replication forks to prime reverse transcription (Zhong et al., EMBO J. 22, 4555-4565, 2003). The RT and X/thumb domains of group II intron RTs are larger than those of retroviral RTs due to an N-terminal extension, an additional N-terminal conserved sequence block (RT-0), and insertions between the conserved sequence blocks in the RT and X/thumb domain, some of which are shared with non-LTR-retrotransposon RTs. It has been suggested that the larger-sized RT and thumb domains of group II intron and related RTs enable tighter binding of template RNAs leading to higher processivity and fidelity during reverse transcription. Unlike retroviral RTs, group II intron RTs lack an RNase H domain and typically have very low DNA-dependent DNA polymerase activity (Smith et al., Genes and Development 19, 2477-2487, 2005).

Group II introns encode a class of RNAs known for their self-splicing reaction. Under certain in vitro conditions, group II intron-encoded RNAs can excise themselves from precursor mRNAs and ligate together their flanking exons, without the aid of a protein. The splicing reaction mechanism is similar to the splicing of nuclear pre-mRNA introns. A number of group II introns also encode reverse transcriptase (RT) open reading frames (ORF) and are active mobile elements. The ORF is typically found in domain DIV of the group II intron encoded RNA. The group II intron RT assists RNA splicing by stabilizing the catalytically active RNA structure and then remains bound to the excised intron RNA in a ribonucleoprotein (RNP) that promotes intron mobility by a process termed "retrohoming." Retrohoming occurs by a mechanism in which the excised intron RNA in the RNPs inserts directly into a DNA target site and is reverse transcribed by the RT. During retrohoming, in which the group II intron facilitates targeting of the intron to appropriate DNA sequences, the group II intron RT must produce an accurate cDNA copy of the intron RNA, which is typically 2-2.5 kb long and folds into highly stable and compact secondary and tertiary structures. Thus, group II intron RTs must have high processivity and fidelity in order to carry out their biological function. Group II intron-derived RTs also lack RNase H activity, which can be beneficial because RNase H specifically degrades the RNA of RNA:DNA hybrids, which allows any RNA to be copied only once and can lead to reduced yields of full length cDNA.

Based on the group II intron-derived reverse transcriptases so far evaluated, these RTs typically exhibit relatively high fidelity and high processivity. The fidelity of reverse transcription refers to the reliability of nucleotide incorporation during reverse transcription of RNA to DNA, with higher fidelity describing nucleotide copying with a low number of errors (e.g., misincorporations). Higher specificity can be provided by using longer and more specific primers, which requires the ability to carry out reverse transcription at higher temperatures. For example, a group II intron reverse transcriptase can provide reverse transcription with an error frequency of $2.0 \times 10^{-5}$ or less, wherein the error frequency represents the proportion of nucleotide copying errors that occur relative to the number of nucleotide copying events that occur without error. Other examples of high fidelity transcription include error frequencies of $1 \times 10^{-4}$, $7.5 \times 5 \times 10^{-5}$, $2.5 \times 10^{-5}$, $1 \times 10^{-5}$, and $5 \times 10^{-6}$.

For further description of the high fidelity of group II intron-derived RTs, see Conlan et al., Nucleic Acids Research, 33, p. 5262-70 (2005).

Examples of suitable group II-derived intron reverse transcriptases include the reverse transcriptases set forth in SEQ ID NO: 1, SEQ ID NO: 2, SEQ ID NO: 3, SEQ ID NO: 4, and SEQ ID NO: 5, which are obtained from *Thermosynechococcus elongatus* (TeI4c, f, and h*) and *Geobacillus stearothermophilus* (GsI1 and GsI2). These sequences are shown in FIGS. 1-5. The invention also encompasses group II intron derived reverse transcriptases that are substantially similar to those set forth in SEQ ID NO: 1, SEQ ID NO: 2, SEQ ID NO: 3, SEQ ID NO: 4, and SEQ ID NO: 5. A reverse transcriptase that is "substantially similar" to the reverse transcriptases provided by sequences 1-5 will share at least 85% identity, more preferably 90% identity and even more preferably 95% identity, and will include only conservative amino acid substitutions in conserved regions. The thermostability of a number of group II intron-derived RTs is shown in FIG. 11, which demonstrates that stabilized reverse transcriptase fusion proteins including the reverse transcriptases as set forth in SEQ ID NO: 1, SEQ ID NO: 2, SEQ ID NO: 3, SEQ ID NO: 4, and SEQ ID NO: 5 have higher thermostability than mesophilic L1.LtrB reverse transcriptase, whether or not it is part of a fusion protein, when evaluated as shown in FIG. 11. The mesophilic L1.LtrB showed a temperature optimum of about 35° C. either alone or as part of a fusion protein.

As noted herein, modified forms of thermostable group II intron-derived RTs can also be used. For example, SEQ ID NO: 3, the TeI4h* RT, does not represent a native form of reverse transcriptase, but rather is a derivative in which the active site was modified from the amino acid sequence YAGD to the amino acid sequence YADD, to more closely resemble the active site of other active group II intron-derived RTs.

The amount by which a given amino acid sequence is "substantially similar" to a reference sequence can be determined for example, by comparing sequence information using sequence analysis software such as the Blastp program, version 2.2.10, of the BLAST 2 search algorithm, as described by Tatusova et al. (FEMS Microbiology Letters, 174, p. 247-50 (1999)), and available on the world wide web at the National Center for Biotechnology Information website, under BLAST in the Molecular Database section. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "similarity" and identity is referred to as "identity."

Amino acid identity is defined in the context of a comparison between a candidate polypeptides and a reference amino acid sequence, and is determined by aligning the residues of the two amino acid sequences (i.e., a candidate amino acid sequence and the reference amino acid sequence) to optimize the number of identical amino acids along the lengths of their sequences; gaps in either or both sequences are permitted in making the alignment in order to optimize the number of identical amino acids, although the amino acids in each sequence must nonetheless remain in their proper order.

Information is available to support a structure-function correlation for group II intron-derived reverse transcriptases. See for example Simon et al., Nucleic Acids Research, 36, p. 7219-29 (2008), which classifies and aligns the RT domains of bacterial reverse transcriptases, and Xiong et al., EMBO J., 9, p. 3353-62 (1990), which provides an alignment of 82 RT sequences showing seven conserved domains and 42 conserved positions. See also Blocker et al, RNA, 11, p. 14-28 (2005), which provides a three-dimensional model of *Lactococcus lactis* L1.LtrB intron RT (the LtrA protein), describes the proteolytic cleavage sites and conserved regions, and provides a sequence alignment analysis of LtrA relative to HIV-1 RT. Accordingly, a variety of stabilized reverse transcriptase fusion proteins that are substantially similar to those set forth in SEQ ID NO. 6-10 can readily be obtained by modification of amino acids outside of the conserved regions, and only conservative modification of amino acids within the known conserved regions.

In one embodiment, the present invention provides a stabilized reverse transcriptase fusion protein having a reverse transcriptase activity that has a half-life of greater than that of the corresponding unbound reverse transcriptase at an elevated temperature, i.e., greater than 37° C. In some embodiments, the half-life of a reverse transcriptase of the present invention may be 5 minutes or greater and preferably 10 minutes or greater at 50° C. In some embodiments, the reverse transcriptases of the invention may have a half-life (e.g., at 50° C.) equal to or greater than about 25 minutes, preferably equal to or greater than about 50 minutes, more preferably equal to or greater than about 100 minutes, and most preferably, equal to or greater than about 200 minutes.

Stabilizer Proteins

The stabilized reverse transcriptase fusion protein of the present invention also includes a stabilizer protein. A stabilizer protein, as defined herein, is a protein forming part of the fusion protein that functions to increase the overall stability of the fusion protein. Stability includes the ability of the protein to retain its conformation and activity. In addition, the stabilizer protein preferably enhances the solubility of the fusion protein, as further described herein with regard to solubility-enhancing proteins. This can be particularly helpful with regard to group II intron RTs, which have been found to be poorly expressed and insoluble in the absence of the intron RNA to which they are ordinarily tightly bound in RNPs. (Vellore et al. Appl. Environ. Microbiol. 70, 7140-7147, 2004; Ng et al., Gene 393, 137-144, 2007) Effective stabilizer proteins include those that include an independent folding domain and/or do not fold into long-lived misfolded intermediates that can influence the propensity of proteins to aggregate. Proteins that will provide an independent folding domain are described by Janin et al., Progress in Biophysics and Molecular Biology, 42, p. 21-78 (1983), and proteins that do not fold into long-lived misfolded intermediates are described by Idicula et al., Protein Science, 14, p. 582-592 (2005). For example, the stabilizer protein can be a protein that includes 50 or more amino acids. In other embodiments, the stabilizer protein can be a larger protein including 100 or more amino acids. As exemplified by the maltose binding protein and NusA proteins provided herein, the stabilizer proteins can also have a size from about 250 amino acids to about 400 amino acids. The stabilizer protein can also be a thermostable protein.

The stabilizer protein can also be or include an affinity protein. The term affinity protein, as used herein, refers to a protein for which there is a readily available ligand that exhibits a high binding constant (i.e., "affinity") for the protein. Affinity proteins are often used in the role of an affinity tag. Affinity proteins, as is known to those skilled in the art, can be provided in fusion proteins to facilitate the purification of the protein connected or fused to the affinity protein by techniques such as affinity purification, in which a tag binds to a ligand within an affinity column. Suitable affinity proteins are known in the art. See for example Waugh, D., Trends in Biotechnology, 23, p. 316-320 (2005), which describes a number of suitable affinity proteins, including glutathione S-transferase, maltose-binding protein, FLAG-tag peptide, biotin acceptor peptide, streptavidin-binding peptide, and calmodulin-binding peptide. For the preparation and use of fusion proteins that include an affinity protein, see for example U.S. Pat. Nos. 5,643,758, 5,654,176, and 7,001,745.

The stabilizer protein can also be a solubility-enhancing protein. Recombinantly-expressed fusion proteins can exhibit low solubility in their host cells and/or in subsequent method applications, which can be ameliorated through inclusion of a solubility-enhancing protein in the fusion protein that substantially increases the solubility of the fusion protein in aqueous environments. Some solubility-enhancing proteins used are also affinity proteins, and can therefore be described as solubility-enhancing affinity proteins. Examples of solubility-enhancing proteins include sugar binding proteins such as arabinose binding protein, chitin binding protein, cellulose binding protein, and maltose binding protein. Other examples of solubility-enhancing proteins include the NusA and Dsb solubility tags provided by Novagen®, and the solubility enhancing tag (SET) provided by Invitrogen™. Harrison has demonstrated the very high solubility provided by the NusA solubility tag, while the solubility enhancement of Dsb is described by Collins-Racie. See Harrison, R. G., inNovations, 11, p. 4-7 (2000), and Collins-Racie et al., Biotechnology, 13, p. 982-87 (1995).

In some embodiments, stabilizer proteins such as solubility-enhancing proteins or affinity proteins can be modified to improve their performance. Modification can include providing one or more substitutions, additions or deletions of amino acids within the protein sequence of the stabilizer protein as compared to the normal, wild-type sequence of the protein. For example, a stabilizer protein such as an affinity protein or a solubility-enhancing protein can be modified by replacing the charged amino acids with uncharged amino acids in certain regions of the protein. Charged amino acids include amino acids with positively or negatively charged side chains. Examples of amino acids with positively charged side chains include arginine, histidine, lysine, and the like. Examples of amino acids with negatively charged side chains include aspartic acid and glutamic acid, and the like. Uncharged amino acids include, but are not limited to, alanine, serine, threonine, glutamine, valine, leucine, isoleucine, phenylalanine, and tyrosine. For example, a maltose binding protein can be modified by replacing one or more of the charged amino acids with alanine.

Examples of suitable affinity proteins include the maltose binding protein amino acid sequence set forth in SEQ ID NO: 11, shown in FIGS. 1-5, and sequences substantially similar to SEQ ID NO: 11. Note that while modification of the affinity protein is not necessary, the maltose binding protein set forth in SEQ ID NO: 11 was modified to replace three charged amino acids with alanine near the C-terminus. Another suitable protein, in this case a solubilizing protein, is the N-utilization substance A (NusA) protein, which has the amino acid sequence set forth in SEQ ID NO: 38, shown in FIG. 18. In additional embodiments of the invention, fusion proteins described herein that include the maltose binding proteins can have the maltose binding protein replaced with N-utilization substance A proteins.

Linker Peptides

In some embodiments, the stabilized reverse transcriptase fusion protein also includes a linker peptide positioned between the stabilizer protein and the thermostable reverse transcriptase. Preferably, the linker peptide is a non-cleavable linker peptide. By "positioned between," it is meant that the linker peptide is connected by a chemical linkage (e.g., an amide linkage) to the N or C terminal of each of the stabilizer protein and the reverse transcriptase, as described in regard to fusion proteins herein. For example, the linker peptide can be connected through an amide linkage to the C terminal region of the Stabilizer protein and the N terminal region of the thermostable reverse transcriptase. By non-cleavable, it is meant that the linker peptide is not readily susceptible to cleavage by a protease.

In additional embodiments, the linker peptide is a rigid linker peptide; i.e., a relatively non-flexible peptide linker. Rigid linker peptides are not required to completely lack flexibility, but rather are significantly less flexible than flexible linker peptides such as glycine-rich peptide linkers. Rigid linker peptides, as a result of their relative lack of flexibility, decrease the movement of the two protein domains attached together by the rigid linker peptide, which in the present case are the stabilizer protein and the thermostable reverse transcriptase. Linker peptides that provide ordered chains such as alpha helical structure can provide rigid linker peptides. For example, Arginine, Leucine, Glutamate, Glutamine, and Methionine all show a relatively high propensity for helical linker formation. However, a non-helical linker including many proline residues can exhibit significant rigidity as well. Examples of rigid linkers include polylysine and poly-DL-alaninepolylysine. Further description of rigid peptide linkers is provided by Wriggers et al., Biopolymers, 80, p. 736-46 (2005). In addition, rigid linker peptides are described at the linker database described by George et al., Protein Engineering, 15, p. 871-79 (2003). Preferably, the rigid linker peptide is also a non-cleavable linker peptide; i.e., a non-cleavable, rigid linker peptide.

Relatively short polypeptides are preferred for use as linker peptides. For example, linker peptides can include from 1 to 20 amino acids. Linker peptides can also include from 1 to 15, from 1 to 10, from 1 to 5, or from 3 to 5 amino acids. Examples of specific sequences that can be used as linker peptides include dipeptides, tripeptides, tetrapeptides, and pentapeptides formed of alanine amino acids. One suitable rigid linker peptide is AAAAA (SEQ ID NO: 12), while another suitable rigid linker peptide is AAAEF (SEQ ID NO: 18). Use of a linker peptide (e.g., a rigid linker peptide) in a fusion protein can provide one or more advantages. For example, while not intending to be bound by theory, it is believed that use of a rigid linker peptide can stabilize the fusion protein by decreasing the amount of movement of the two halves of the fusion protein relative to one another. While very short (i.e., 1 or 2 amino acid) linkers can be used, it is preferable to use linkers that include from 3 to 5 amino acids.

The linker peptide can be either cleavable or non-cleavable by a protease. Affinity proteins are often associated to another protein in a fusion protein using a cleavable peptide so that the affinity protein can be removed. However, in the present invention the stabilizer protein (e.g., an affinity protein) remains bound to the reverse transcriptase, for the reasons described herein. Accordingly, it is generally preferable that the linker peptide be non-cleavable. However, cleavable linkers can be used in some embodiments. For example, cleavable linkers, including rigid cleavable linker peptides, that are susceptible to protease cleavage can be used if it is desirable to remove the stabilizer protein during a subsequent step and exposure to the cleaving protease is avoided during use of the fusion protein.

Use of Stabilized Reverse Transcriptase Fusion Proteins

The invention also provides a method for preparing a cDNA from an RNA (e.g., mRNA, rRNA, tRNA, and miRNA), which is required for other methods such as the reverse transcription polymerase chain reaction (RT-PCR). As used herein, the term "RT-PCR" refers to the replication and amplification of RNA sequences. In this method, reverse transcription is coupled to PCR, e.g., as described in U.S. Pat. No. 5,322,770. In RT-PCR, the RNA template is converted to cDNA due to the reverse transcriptase activity of an enzyme, and then amplified using the polymerizing activity of the same or a different enzyme.

In the practice of the invention, cDNA molecules may be produced by mixing one or more nucleic acid molecules (e.g., RNA) obtained from cells, tissues, or organs using methods that are well known in the art, with the composition of the invention, under conditions favoring the reverse transcription of the nucleic acid molecule by the action of the enzymes of the compositions to form a cDNA molecule (single-stranded or double-stranded). Thus, the method of the invention comprises (a) mixing one or more nucleic acid templates (preferably one or more RNA or mRNA templates, such as a population of mRNA molecules) with stabilized RT fusion protein of the invention and (b) incubating the mixture under conditions sufficient to permit cDNA synthesis of all or a portion of the one or more nucleic acid templates.

In one aspect, the method includes the steps of (a) adding a primer to an RNA molecule and (b) incubating the RNA molecule in the presence of one or more deoxy or dideoxy-ribonucleoside triphosphates and a stabilized reverse transcriptase fusion protein comprising a thermostable reverse transcriptase connected to a stabilizer protein under conditions sufficient to synthesize a cDNA molecule complementary to all or a portion of the RNA molecule. Adding the primer to an RNA molecule may include hybridizing the primer to the RNA molecule. In some embodiments, the stabilized reverse transcriptase fusion protein can also include a linker peptide connecting the stabilizer protein to the thermostable reverse transcriptase. Preferably, the reverse transcription is performed within a temperature range where the RNA includes a substantially decreased amount of obstructing stable secondary or tertiary structure. This can be a temperature from about 45° C. to about 81° C., with a more preferred temperature range being from about 45° C. to about 65° C. This can also be described as a temperature range in which the RNA does not form a significant amount of stable secondary or tertiary structure. Due to the high fidelity and other advantages of group II intron-derived RTs, their use may be preferred. For example, the stabilized reverse transcriptase fusion protein can include a group II intron-derived reverse transcriptase with an amino acid sequence identity that is substantially similar to a sequence selected from the group consisting of SEQ ID NO: 1, SEQ ID NO: 2, SEQ ID NO: 3, SEQ ID NO: 4, or SEQ ID NO: 5, a non-cleavable linker consisting of 1 to 20 amino acids, and the stabilizer protein comprises a solubility-enhancing or affinity protein. The stabilized reverse transcriptase fusion protein can also include a linker peptide between the stabilizer peptide and the reverse transcriptase, which can have a length from 1-20 amino acids, can be a non-cleavable linker, or can be rigid linker. Embodiments of the method can perform reverse transcription with an error frequency of $2.0 \times 10^{-5}$ or less. Particularly at a temperature from about 45° C. to about 65° C.

The stabilized reverse transcriptase fusion proteins can also be used in other applications. For example, stabilized RT fusion proteins can be used for the cloning of differentially expressed 5' ends of mRNAs; a process referred to as rapid amplification of cDNA ends (RACE) and variations thereof such as RNA ligase mediated RACE (RLM-RACE). Stabilized RT fusion proteins can also be used for the mapping of chemical footprints in RNA, differential display RT-PCR, which allows for the analysis of gene expression among cell populations, and in-situ PCR for medical diagnosis.

Preparation of Stabilized Reverse Transcriptase Fusion Proteins

An expression vector containing a stabilized reverse transcriptase fusion protein-encoding nucleic acid molecule may be used for high-level expression of stabilized reverse transcriptase fusion protein in a recombinant host cell. Expression vectors may include, but are not limited to, cloning vectors, modified cloning vectors, specifically designed plasmids or viruses. A variety of expression vectors may be used to express recombinant stabilized reverse transcriptase fusion sequences in appropriate cell types. For example, bacterial vectors, mammalian vectors, fungal vectors, and insect vectors may be used for expression in bacteria, mammalian cells, fungal cells, and insect cells, respectively.

Stabilized reverse transcriptase fusion proteins can be prepared by obtaining a nucleotide sequence capable of expressing a stabilized reverse transcriptase fusion protein and then expressing that nucleotide sequence in a host cell. The stabilized reverse transcriptase fusion proteins expressed by the host cell can then be purified using a variety of techniques known to those skilled in the art, depending in part on the nature of the host cell.

Nucleotide sequences capable of expressing stabilized reverse transcriptase fusion proteins of the invention can be prepared using a variety of methods known to those skilled in the art. For example, the nucleotide sequences can be prepared using recombinant plasmids in which various linkers, reverse transcriptases, and stabilizer proteins are combined, as described in Example 1 herein.

The present invention also relates to host cells transformed or transfected with vectors comprising a nucleic acid molecule capable of expressing a stabilized reverse transcriptase fusion protein. Recombinant host cells may be prokaryotic or eukaryotic, including but not limited to, bacteria such as E. coli, fungal cells such as yeast, mammalian cells including, but not limited to, cell lines of bovine, porcine, monkey and rodent origin; and insect cells including but not limited to Drosophila and silkworm derived cell lines. Such recombinant host cells can be cultured under suitable conditions to produce a stabilized reverse transcriptase fusion protein or a biologically equivalent form. As defined herein, the term "host cell" is not intended to include a host cell in the body of a transgenic human being, human fetus, or human embryo.

As noted above, an expression vector containing DNA encoding a stabilized reverse transcriptase fusion protein may be used for expression of stabilized reverse transcriptase fusion protein in a recombinant host cell. Therefore, another aspect of this invention is a process for expressing a stabilized reverse transcriptase fusion protein in a recombinant host cell, comprising: (a) introducing a vector comprising a nucleic acid comprising a sequence of nucleotides that encodes a stabilized reverse transcriptase fusion protein into a suitable host cell, wherein the stabilized reverse transcriptase fusion protein comprises a thermostable reverse transcriptase connected to a stabilizer protein directly or via a linker and (b) culturing the host cell under conditions which allow expression of the stabilized reverse transcriptase fusion protein. The stabilized reverse transcription fusion protein can be varied to include any of the features described herein, such as the inclusion of a linker peptide connecting the thermostable reverse transcriptase and the stabilizer protein.

Following expression of a stabilized reverse transcriptase fusion protein in a host cell, the stabilized reverse transcriptase fusion protein may be recovered to provide purified stable reverse transcriptase fusion protein. Several protein purification procedures are available and suitable for use. For instance, see Example 2 provided herein. Recombinant protein may be purified from cell lysates and extracts by various combinations of, or individual application of salt fractionation, ion exchange chromatography, size exclusion chromatography, hydroxylapatite adsorption chromatography and hydrophobic interaction chromatography. The use of affinity tags in some embodiments of the invention can facilitate purification of the protein. For example, the stabilized reverse transcriptase fusion protein can be separated from other cellular proteins by use of an immunoaffinity column made with monoclonal or polyclonal antibodies specific for the reverse transcriptase or stabilizer protein portion of the fusion protein. Heating can be used to separate the stabilized reverse transcriptase fusion protein from host proteins, which are not stable at elevated temperatures and will therefore precipitate.

The nucleic acids capable of expressing a stabilized RT fusion protein may be assembled into an expression cassette which comprises sequences designed to provide for efficient expression of the fusion protein in a host cell. The cassette preferably contains a stabilized reverse transcriptase fusion protein-encoding open reading frame, with related transcriptional and translations control sequences operatively linked to it, such as a promoter, and termination sequences. For example, the open reading frame can include a nucleic acid that encodes a polypeptide with an amino acid sequence identity that is substantially similar to a sequence selected from the group consisting of SEQ ID NO: 6, SEQ ID NO: 7, SEQ ID NO: 8, SEQ ID NO: 9, or SEQ ID NO: 10, as shown in FIGS. 1-5, respectively. In a preferred embodiment, the promoter is a T7 or a tac promoter for expression in E. coli, although those skilled in the art will recognize that any of a number of other known promoters may be used. E. coli also has rho independent and dependent terminators and can use T7 polymerase for rapid DNA replication. In eukaryotic cells, inclusion of a polyadenylation site will be helpful for the correct processing of mRNA.

The open reading frame can also include polynucleotide sequences as set forth in SEQ ID NO: 13, SEQ ID NO: 14, SEQ ID NO: 15, SEQ ID NO: 16, and SEQ ID NO: 17, as shown in FIGS. 6-10, respectively. Alternately, the open reading frame can include polynucleotide sequences that are substantially similar to those set forth in SEQ ID NO: 13, SEQ ID NO: 14, SEQ ID NO: 15, SEQ ID NO: 16, and SEQ ID NO: 17. In this particular context, the term "substantially similar" refers to variants in the nucleotide sequence in which codons that encode the same amino acid can be used interchangeably such that the nucleotide sequence will still result in the translation of an amino acid sequence corresponding to SEQ ID NO: 6-10. The stabilized reverse transcriptase fusion protein open reading frame polynucleotide preferably has at least about 80% identity, at least about 90% identity, at least about 95% identity, or at least about 98% identity to a polynucleotide sequence selected from the group consisting of SEQ ID NO: 13, SEQ ID NO: 14, SEQ ID NO: 15, SEQ ID NO: 16, and SEQ ID NO: 17.

Nucleotide identity is defined in the context of a comparison between a candidate stabilized reverse transcriptase fusion protein open reading frame and a polynucleotide sequence selected from the group consisting of SEQ ID NO: 13, SEQ ID NO: 14, SEQ ID NO: 15, SEQ ID NO: 16, and SEQ ID NO: 17, and is determined by aligning the residues of the two polynucleotides to optimize the number of identical nucleotides along the lengths of their sequences; gaps in either or both sequences are permitted in making the alignment in order to optimize the number of shared nucleotides, although the nucleotides in each sequence must nonetheless remain in their proper order. Preferably, two nucleotide sequences are compared using the Blastn program of the BLAST 2 search algorithm, as described by Tatusova, et al. (FEMS Microbiology Letters, 174, p. 247-50 (1999)), and available on the world wide web at the National Center for Biotechnology Information website, under BLAST in the Molecular Database section. Preferably, the default values for all BLAST 2 search parameters are used, including reward for match=1, penalty for mismatch=–2, open gap penalty=5, extension gap penalty=2, gap×dropoff=50, expect=10, wordsize=11, and optionally, filter on. In the comparison of two nucleotide sequences using the BLAST search algorithm, nucleotide identity is referred to as "identities."

With regard to protein preparation from nucleotide sequences, it is noted that a "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. Accordingly, the nucleotide sequences used to prepare the particular amino acid sequences of stabilized reverse transcriptase fusion proteins can vary considerably, depending on the particular codons used. For reasons not completely understood, alternative codons are not uniformly present in the endogenous DNA of differing types of cells, and there exists a natural hierarchy or "preference" for certain codons in certain types of cells. Accordingly, in some embodiments the choice of codons used to express a stabilized reverse transcriptase fusion protein may be optimized through use of particular codons to result in higher levels of expression.

In accordance with this invention, the stabilized reverse transcriptase fusion protein expression cassette is inserted into a vector. The vector is preferably a plasmid or adenoviral vector, although linear DNA linked to a promoter, or other vectors, such as adeno-associated virus or a modified vaccinia virus, retroviral or lentiviral vector may also be used. In particular, the use of *E. coli* plasmid vectors is preferred.

A detailed description of the work conducted by the inventors to develop and evaluate stabilized reverse transcriptase fusion proteins is provided below.

Expression and Purification of Group II Intron RTs as MalE Fusion Proteins

The expression and solubility of poorly behaved proteins can sometimes be improved by fusion of highly soluble proteins, like maltose-binding protein (MalE) or N utilization substance A (NusA) (Nallamsetty et al., Protein Expression and Purification 45, 175-182, 2005). The MalE tag additionally permits facile purification of the protein via amylose-affinity chromatography. The inventors therefore tested whether group II intron RTs could be expressed and purified as MalE fusions. Initially, a MalE tag was fused to the N-terminus of the RT via a TEV protease-cleavable linker in the expression vector pMal-c2t (FIG. 12B). The MalE-RT fusion proteins for several of the *T. elongatus* group II intron RTs expressed well in *E. coli* and could be purified by a procedure that involves polyethyleneimine (PET)-precipitation to remove nucleic acids, followed by amylose-affinity and heparin-Sepharose chromatography. Further, the uncleaved MalE-RT fusion proteins assayed soon after purification had high thermostable RT activity. However, the yields of these proteins were <0.2 mg/l for the *Thermosynechococcus* proteins. Additionally, when the MalE tag was removed by cleavage with TEV protease, the RTs immediately formed an insoluble precipitate, while if the tag was left uncleaved, the MalE-RT fusion proteins progressively lost RT activity and were degraded within days, even when stored on ice or flash frozen in 50% glycerol. The latter findings were surprising because proteins that fold properly in the presence of a solubility tag tend to remain soluble after cleavage of the tag (Nallamsetty et al., Protein Expression and Purification 45, 175-182, 2005). The group II intron RTs, which were active with but not without the attached MalE tag, appear to be an exception. The finding that the stabilizer protein must remain attached to the thermostable reverse transcriptase suggests that it plays an active role in keeping the thermostable reverse transcriptase soluble and active.

To overcome these difficulties, the inventors tested whether the group II intron RTs could be stabilized in active form by attaching the MalE tag to the protein via a non-cleavable rigid linker. Such MalE-rigid fusions typically have a linker region of 3 to 5 alanine residues combined with changes at the C-terminus of the MalE tag to replace charged amino acid residues with alanines (Smyth et al., Genes and Development 19, 2477-2487, 2003). These rigid fusion linkers reduce conformational heterogeneity, enabling crystallization of proteins with attached linkers for structure determination (Smyth et al., ibid). For the MalE-RF-RT fusions tested here, the MalE/linker region of pMal-c2t TVDEALKDAQTNS$_3$N$_{10}$LENLYFQGEF (SEQ ID NO: 19) was modified to TVDAALAAAQTAAAAA (SEQ ID NO: 20) and called a MalE-RF (rigid fusion) tag (FIG. 12B).

To rapidly assess whether the MalE-RF tag affects the activity of group II intron RTs, the inventors tested whether the MalE-RF-RTs could support retrohoming in vivo. For initial tests, the RTs chosen were the LtrA protein encoded by the *L. lactis* L1.LtrB intron, and TeI4h* RT, an activated derivative of the RT encoded by the thermostable *T. elongatus* TeI4h intron. In retrohoming assays at 37° C., the MalE-RF-LtrA protein supported retrohoming at an efficiency of 20% compared to 86% for native LtrA, while in retrohoming assays at 48° C., the MalE-RF-TeI4h* protein supported retrohoming at an efficiency of 87% compared to 100% for the unfused TeI4h* protein; see Table 1. Thus remarkably both MalE-RF-RTs retain the ability to support retrohoming with high albeit somewhat reduced efficiencies despite the presence of the attached maltose-binding protein rigid linker sequence. These findings imply that the proteins retain substantial levels of all activities required for retrohoming, including RT, RNA splicing, and DNA endonuclease activity. This mobility assay provides a convenient screen for active group II intron RTs.

TABLE 1

Retrohoming efficiencies for different RTs

| RT | Efficiency |
| --- | --- |
| TeI4h* (48° C.) | 100% |
| MalE-KF-TeI4h* (48° C.) | 87% |
| LtrA (37° C.) | 86% |
| MalE-RF-LtrA (37° C.) | 20% |

Retrohoming assays were done in E. coli HMS174(DE3) as described previously for the L1.LtrB intron (LtrA protein) (Guo et al. Science 289, 452-457, 2000, Karberg et al. Nature Biotech. 19, 1162-1167, 2001) and TeI4h*. The $Cap^R$ intron-donor plasmids use a T7lac promoter to express a ΔORF intron (I-ΔORF) with short flanking 5' and 3' exons (E1 and E2, respectively) and a T7 promoter in DIV, followed by the RT ORF downstream of E2. The $Amp^R$ recipient plasmids contain a target site for the intron (ligated E1-E2 sequences) cloned upstream of a promoterless $tet^R$ gene. Intron expression was induced with IPTG (0.1 mM for LtrA and MalE-RF-LtrA and 0.5 mM for TeI4h* and MalE-RF-TeI4h*) for 1 h at the indicated temperature. Retrohoming of the intron carrying the T7 promoter into the target site activates the expression of the $tet^R$ gene, enabling selection for $Tet^R$+$Amp^R$ colonies. Retrohoming efficiencies were calculated as the ratio of $(Amp^R+Tet^R)/Amp^R$ colonies.

Encouraged by these findings, the inventors constructed plasmids in which several group II intron RTs were expressed with a MalE tag fused to the N-terminus of the protein via a rigid linker in the vector pMal-c2t. The RTs tested included several T. elongatus group II intron RTs, whose ability to support retrohoming had been tested previously using the above plasmid assay and two G. stearothermophilus group II intron RTs related to group II intron RTs that had previously been difficult to purify with high yield and activity (Vellore et al., Appl. Environ. Microbiol. 70, 7140-7147, 2004; Ng et al., Gene 393, 137-144, 2007). In some constructs, the inventors added an additional C-terminal His6-tag to enrich for full-length protein in the purification. The MalE-RF-RT fusion proteins were expressed in E. coli and purified by a procedure that involves PEI-precipitation of nucleic acids followed by amylose-affinity and heparin-Sepharose chromatography. An additional Ni column chromatography step was included for constructs with a C-terminal His6 tag. The proteins were dialyzed against the purification buffer with 50% glycerol, flash frozen, and stored at −80° C. The final protein preparations were >95% pure with yields of 0.5-2.2 mg/ml and their RT activity was undiminished after storage for at least six months.

RT Assays

To assess their thermostability, the inventors first assayed the RT activity of fusions MalE-RF-TeI4c, TeI4h*, and TeI4f from Thermosynechococcus elongatus and MalE-RF-GsI1 and GsI2 from Geobacillus stearothermophilus at temperatures between 25 and 77° C. These initial assays were done by using poly(rA)/oligo(dT)$_{42}$ as the template-primer substrate and quantifying polymerization of $^{32}$P-dTTP into high molecular weight material. The relatively long 42-nt dT primer was used so that it would remain annealed to the poly(rA) template at higher temperatures (calculated Tm=69° C.). The LtrA protein with and without an N-terminal MalE-RF tag was assayed in parallel as a mesophilic RT control (FIG. 11). Whereas the LtrA protein had a temperature optimum of ~35° C. with or without the MalE rigid fusion tag, the other five MalE-RF-RT's had higher temperature optima ranging from 45-61° C. The two most active and thermostable RTs, MalE-RF-GsI2 and MalE-RF-TeI4c had temperature optima of 61° C. and retained substantial activity at 70° C. (where the assay may be limited by the stability of the primer-template base pairing). Of the two RTs, MalE-RF-TeI4c had the highest activity and was assayed at lower protein concentrations (50 nM) and for shorter times (90 sec) than the other RTs (100 nM, 5 min) in order to remain within the linear range. Tests with the MalE-RF-TeI4c protein showed that inclusion of maltose (10 μM to 1 mM), which can affect the conformation of the MalE tag, had little if any effect on RT activity.

Effect of Changing the Tag and Linker on RT Activity

Figure 13:
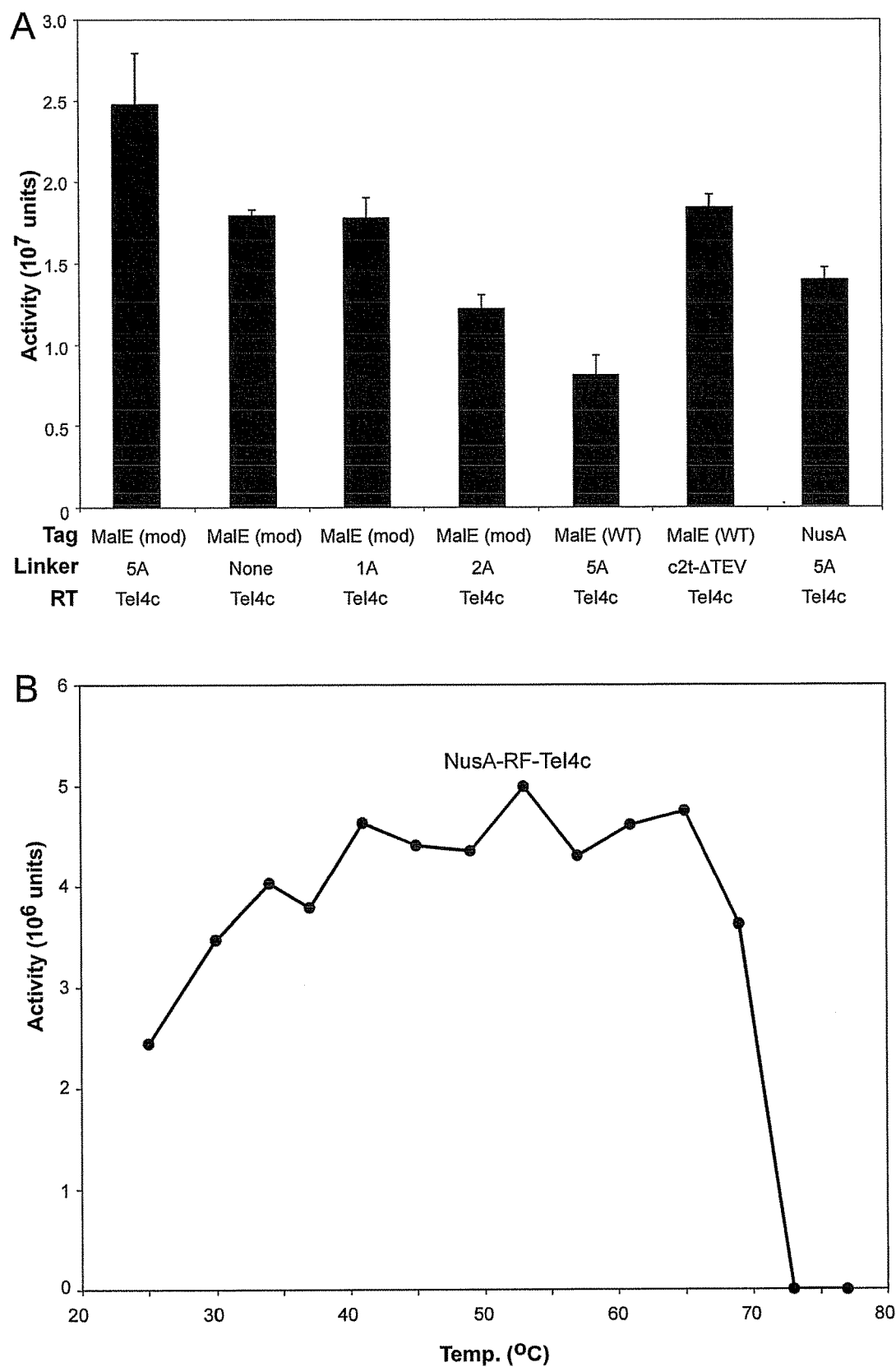
FIG. 13 provides graphs showing the RT activity of derivatives of MalE-RF-TeI4c RT with different rigid fusion linker or solubility tag sequences. Panel 13(A) provides a bar graph showing RT activity at 60° C. Reaction with MalE-RF-TeI4c RT (left bar) or variants containing different tag or linker sequences (right bars) were done as in FIG. 11 using 50 nM protein and 100 nM poly(rA)/oligo(dT)$_{42}$ and incubating for 90 sec. Values are the mean for three determinations with error bars indicating the standard deviation. Panel 13(B) provides a graph showing the temperature profile of RT activity for NusA-RF-TeI4c RT. RT activity was assayed as in FIG. 11 using 50 nM protein and 100 nM poly(rA)/oligo(dT)$_{42}$ and incubating for 2 min at the indicated temperature. The y-axis shows radioactivity bound to the filter (PhosphorImager units) for each protein (panel A) or for NusA-RF-TeI4c RT as a function of reaction temperature (panel B).

To determine optimal properties of the tag and linker, the inventors constructed variants of the MalE-RF-TeI4c RT. The MalE-RT-TeI4c RT (left bar) and variant proteins (right bars) were purified and assayed for RT activity with poly (rA)/oligo(dT)$_{42}$ as described above (FIG. 13A). MalE-RT-TeI4c has a modified MalE tag (MalE (mod)) with 3 charged amino acid residues changed to alanines and a linker of 5 alanine residues linked to the N-terminus of the RT. Variants in which the 5 alanine-residue linker was removed or shortened to 1 or 2 alanine residues had substantial but reduced RT activity, as did a variant in which the modified MalE tag was replaced with wild-type MalE (MalE (WT)) (FIG. 13A). A variant of TeI4c with the MalE (WT) tag followed by the pMal-c2t linker deleted for the TEV protease cleavage site also had substantial but reduced RT activity (FIG. 13A). A variant in which the wild-type MalE tag was attached to the C-terminus of the TeI4c RT did not express well in E. coli, presumably reflecting that the nascent TeI4c RT cannot fold properly without prior expression of the MalE tag. Finally, a variant with an N-terminal rigid fusion to NusA (N utilization substance protein) instead of MalE had substantial thermostable RT activity (FIGS. 13A and B).

Temperature Profile for cDNA Synthesis

Figure 14:
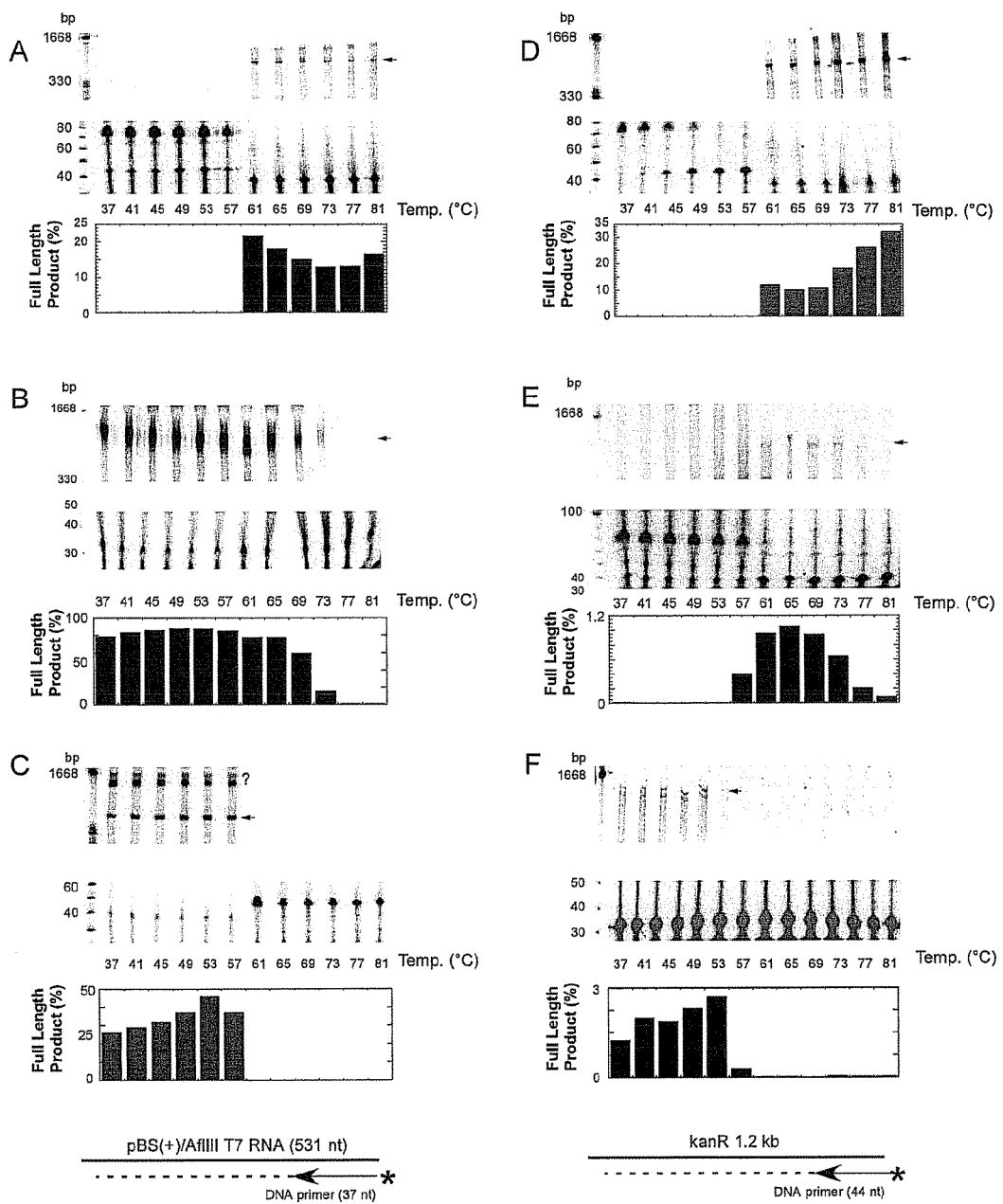
FIG. 14 provides graphs and autoradiograms that provide a comparison of cDNA synthesis by MalE-RF-TeI4c, MalE-RF-GsI2, and SuperScript III RT activity at different temperatures. In panels (A-C), the substrate was a 531-nt RNA transcribed from AflIII-digested pBS KS(+) with an annealed 5'-labeled 37-nt primer, and in panels (D-F), the substrate was a 1.2-kb kanR RNA with an annealed 5'-labeled 44-nt DNA primer. Reactions were done by incubating 100 nM of annealed template/primer with 200 nM enzyme in 100 mM KCl, 20 mM Tris HCl pH 7.5, 10 mM MgCl$_2$ and 10 mM DTT for MalE-RF-TeI4c RT (panels A and D) and MalE-RF-GsI2 RT (panels B and E) and in the manufacturer's buffer for SuperScript III RT (panels C and F). Reactions were initiated by adding dNTPs to a final concentration of 1.25 mM, incubated for 30 min at the indicated temperature, and terminated by adding 0.1% SDS/250 mM EDTA (final concentrations) followed by phenol-CIA extraction. The products were analyzed by electrophoresis in a denaturing 6% polyacrylamide gel, which was dried and quantified with a PhosphorImager. In each panel, the top and bottom autoradiograms show portions of the gel containing the full-length product (arrow) and unextended or partially extended primer, respectively, and the bar graphs show the percentage of primer that was extended to full-length cDNA based on PhosphorImager quantitation. "?" indicates unidentified bands not used in quantitation of full-length product. A 5'-labeled 10-bp ladder (Invitrogen™) was used as size markers. Schematics of two template primer substrates are shown at the bottom of the figure.

FIG. 14 shows assays of cDNA synthesis at different temperatures using in vitro transcribed RNA templates with DNA primers annealed to their 3' ends comparing two of the thermostable group II intron RTs (MalE-RF-TeI4c and MalE-RF-GsI2) with a commercially available RT, SuperScript III (Invitrogen™), which has been reported to be active at 55° C. (Potter et al. Focus (Invitrogen Newsletter) 25.1, 19-24, 2003). One template was a 531-nt in vitro transcript synthesized from AflIII-digested pBS KS(+) with a $^{32}$P-labeled 37-nt DNA primer annealed (FIGS. 14A-C) and the other was a 1.2-kb kanR RNA (SEQ ID NO: 21; shown in FIG. 15) with a $^{32}$P-labeled 44-nt DNA primer (FIG. 14D-E). The reaction was incubated for 30 min at the indicated temperature, and the products were analyzed by electrophoresis in a denaturing 6% polyacrylamide gel. In each panel, the top and bottom autoradiograms show portions of the gel containing the full-length product and unextended or partially extended primers, respectively, and the bar graphs show the percentage of primer that was extended to full-length cDNA.

With the 531-nt RNA template, the MalE-RF-TeI4c RT had a temperature optimum for full-length cDNA synthesis of 61-81° C. The MalE-RF-GsI2 RT synthesized full-length cDNA at temperatures between 37 and 69° C., whereas SuperScript III RT had no activity at temperatures higher than 57° C. (FIG. 14A-C). With the 1.2-kb RNA template, the MalE-RF-TeI4c and MalE-RF-GsI2 RT had temperature optima of 61-81° C. and 61-69° C., respectively, while SuperScript III RT again had no activity at temperatures higher than 57° C. (FIG. 14D-E).

Analysis of cDNA Synthesis by qRT-PCR

Figure 16:
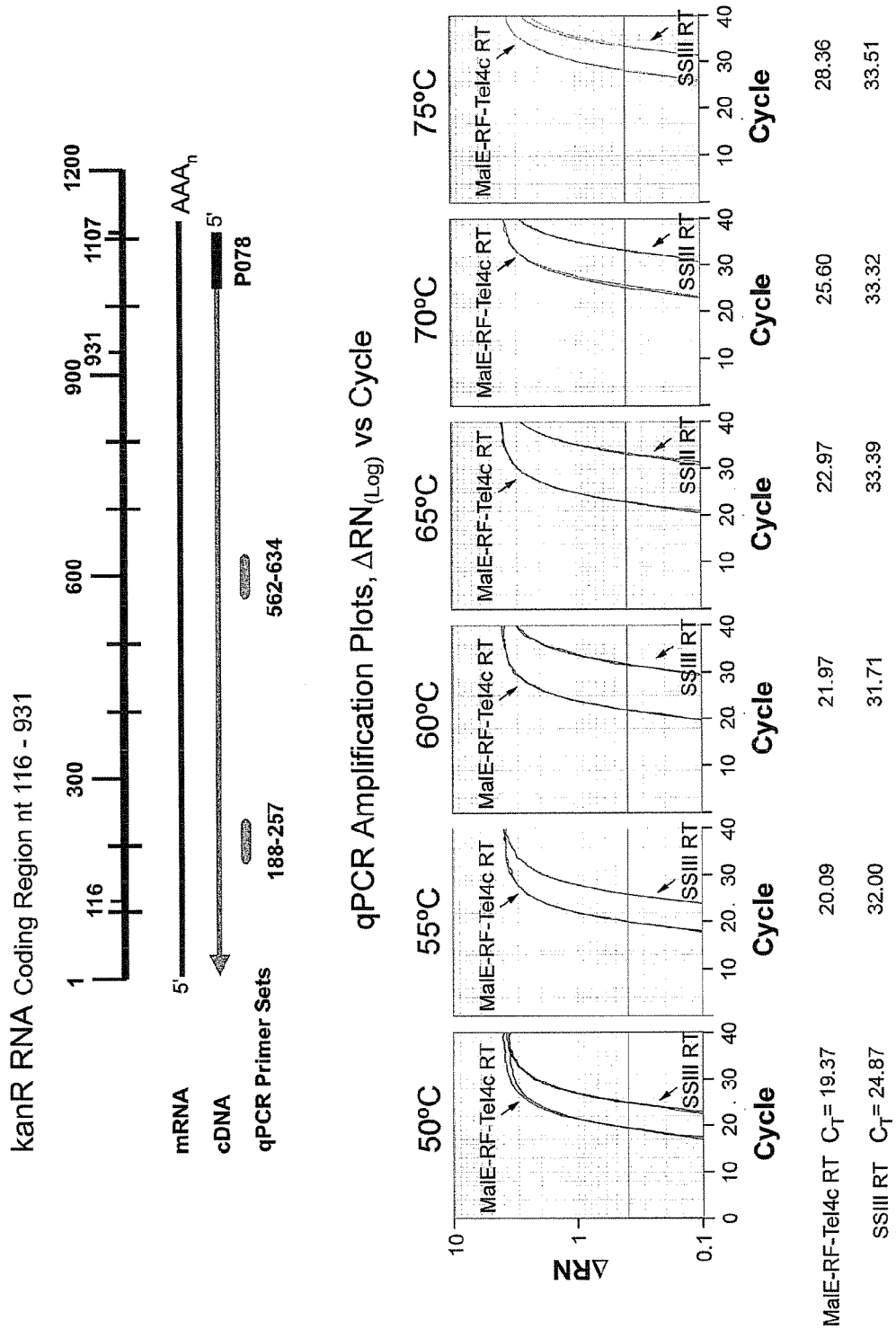
FIG. 16 provides semi-log plots obtained from qRT-PCR to compare amounts of cDNA synthesis at different temperatures by MalE-RF-TeI4c RT and SuperScript III RT. cDNA was synthesized with MalE-RF-TeI4c RT or SuperScript III RT (SSIII RT) using the 1.2-kb kanR RNA with annealed primer P078 (Tm=80° C.) and detected with primer/probe sets at nt 188-257 and nt 562-634 (the data for detection with primer set nt 188-257 are shown in the figure; the data obtained with the primer set nt 562-634 are shown in FIG. 17). The qPCR amplification curves show a semi-log plot of fluorescence (ΔRN) versus cycle number. For each sample, duplicate wells were analyzed and are depicted in each amplification plot. The cycle threshold ($C_T$) values (the cycle at which the fluorescence crosses the threshold 0.4) for each cDNA synthesis reaction by MalE-RF-TeI4c or SuperScript III RT are indicated below the curves. Lower $C_T$ values indicate a larger number of cDNAs synthesized FIG. 17 provides semi-log plots obtained from qRT-PCR to compare processivity of cDNA synthesis by MalE-RF-TeI4c RT and SuperScript III RT. cDNA was synthesized with MalE-RF-TeI4c or SuperScript III RT using the 1.2-kb kanR RNA with annealed primer P078 (Tm=80° C.) and detected with primer/probe sets at nt 188-257 and nt 562-634. cDNA samples were obtained at 60° C. (A, B) and 65° C. (C, D). For each sample, triplicates were analyzed and are depicted in each amplification plot. Average copy numbers are derived from a standard curve of quantitated and diluted pET9 plasmid. Detection of similar numbers of cDNA copies with the two primer sets, as seen for MalE-RF-TeI4c RT, shows that most cDNAs extend to near the end of the RNA template, indicative of high processivity. A lower number of cDNA copies detected with the primer set near the 5' end (nt 188-257) compared to the primer set closer to the 3' end (nt 562-634), as seen for SuperScript III RT, indicates that the RT falls off or is in some other way impeded from reaching the 5' end of the RNA template.

In addition to gel analysis, the inventors used qRT-PCR to compare the amounts of cDNAs synthesized by the MalE-RF-TeI4c and SuperScript III RTs using the 1.2-kb RNA template. The inventors first compared the amounts of full-length cDNA produced at temperatures between 50 and 75° C. (FIG. 16). The cDNAs for qPCR were synthesized in reactions containing 5×10$^8$ copies of kanR RNA as a template, 200 nM MalE-RT-TeI4c or 200 U of SuperScript III RT for 30 min at six different temperatures. Reactions with SuperScript III were done according to the manufacturer's specifications. The reaction mix containing all components except for dNTPs was preincubated at the desired temperatures for 2 min and started by adding the dNTPs. After 30 min, the reactions were terminated by quickly freezing on dry ice. A 5-µl portion of each cDNA synthesis was used in qPCR reactions containing TaqMan® Gene Expression mix and two forward, reverse, and dual-labeled primer probe mixes located at nt 188-257 and 562-634 of the kanamycin RNA. With the primer set closest to the 5' end of the RNA (nt 188-257), the cycle threshold ($C_T$) values were significantly lower for the MalE-RF-TeI4c RT than for SuperScript III RT at all temperatures tested (FIG. 16), indicating that MalE-RF-TeI4c had synthesized larger amounts of cDNAs extending to near the 5' end of the RNA template. Notably, the difference in amounts of cDNAs synthesized was most pronounced at temperatures between 55 and 65° C., where the activity of SuperScript III falls off rapidly.

To compare the processivity of cDNA synthesis by MalE-RF-TeI4c and SuperScript III RTs, the same cDNA samples obtained at 60 and 65° C. were analyzed with two different amplicon primer/probe sets: 188-257, which detects cDNAs that are 920-nt long, and 562-634, which detects cDNAs that are 546 nt long (FIG. 17). In this case, cycle threshold results for cDNA samples were plotted against a standard curve obtained with Novagen® double-stranded DNA plasmid vector pET9a to determine copy numbers equivalents. With the 188-257 amplicon primer/probe set, 972,815 copies were detected with the MalE-RF-4-c TeI4c RT versus 64,456 copies with SuperScript RT at 60° C. (~15 fold difference), and that ratio increased to 732,559 versus 661 at 65° C. (~1100 fold difference). Further, at both temperatures, the MalE-RF-TeI4c RT shows little difference in the copy numbers of cDNAs detected by the two primer sets, showing that the MalE-RF-TeI4c RT synthesizes mostly full-length cDNAs, indicative of high processivity. By contrast, SuperScript III RT showed lower numbers of longer cDNAs detected by the 188-257 primer set than the 562-634 primer set at both temperatures, indicating that this RT falls off or is otherwise impeded before reaching the 5' end of the RNA, resulting in synthesis of shorter cDNAs.

Fidelity of Nucleotide Incorporation by TeI4c and TeI4h* RTs

The inherent fidelity of the TeI4h* and TeI4c RTs (i.e., the native group II intron RT, not a stabilized RT fusion protein) was assessed initially by sequencing introns that had undergone retrohoming in *E. coli* plasmid assays (Table 2). The maximum error frequencies for the TeI4h* RNA promoting retrohoming of a TeI4h*-ΔORF intron RNA at 37 and 48° C. were 1.6×10$^{-5}$ and 4.1×10$^{-6}$, respectively. The TeI4c RT is encoded by the outer intron of a "twintron", a configuration in which one group II intron (TeI3c) has inserted into another (TeI4c), and can efficiently mobilize both introns. The maximum error frequencies for the TeI4c RT promoting retrohoming of TeI3c or TeI4c at 48° C. were 1.1×10$^{-5}$ and 2.2×10$^{-5}$. These error frequencies are comparable to that estimated previously for the L1.LtrB intron RT (LtrA) promoting retrohoming of the L1.LtrB intron, ~10$^{-5}$ at 37° C. (Conlan et al., Nucl. Acids Res. 33, 5262-5270, 2005).

TABLE 2

Fidelity of group II intron RTs as measured by frequency of nucleotide misincorporation during retrohoming

| RT | TeI4h* | TeI4h* | TeI4c | TeI4c |
|---|---|---|---|---|
| Intron | TeI4h*-ΔORF | TeI4h*-ΔORF | TeI3c-ΔORF | TeI4c-ΔORF |
| Temp. (° C.) | 37 | 48 | 48 | 48 |
| Nts sequenced | 244,253 | 244,980 | 265,858 | 537,354 |
| Mutations | 4 | 1 | 3 | 12 |
| Error Frequency | 1.6 × 10$^{-5}$ | 4.1 × 10$^{-6}$ | 1.1 × 10$^{-5}$ | 2.2 × 10$^{-5}$ |

Retrohoming was done in *E. coli* HMS174(DE3) with donor plasmids expressing the indicated intron and RT and recipient plasmids containing the intron target site (ligated E1-E2) sequences cloned upstream of a promoterless tet$^R$ gene. After selection of Tet$^R$ colonies, introns that had integrated into the target site in recipient plasmid were amplified by colony PCR using the primers Rsense (5'-ACAAATAGGGGTTCCGCGCAC; SEQ ID NO: 22) and Te680rc (5'-GTTGGTGACCGCACCAGT; SEQ ID NO: 23) and Te420f (5'-AACGCGGTAAGCCCGTA; SEQ ID NO: 24) and Rev2pBRR (5'-AATGGACGATATCCCGCA; SEQ ID NO: 25) for the 5'- and 3'-integration junctions, respectively. The PCR fragments were then sequenced. Table 2 indicates the induction temperature for retrohoming, the total number of intron nucleotides sequenced, the number of mutations (errors), and the error frequency.

The following examples of methods for preparing and characterizing stabilized RT fusion proteins are included for purposes of illustration and are not intended to limit the scope of the invention.

EXAMPLES

Example 1: Recombinant Plasmids pMalE-TeI4c, pMalE-TeI4f, pMalE-TeI4h* contain the RT ORF of the indicated mobile group II intron with a fused N-terminal MalE tag cloned behind the tac promoter in the expression vector pMal-c2t. The latter is a derivative of pMal-c2x (New England Biolabs, Ipswich Mass.) in which the factor Xa protease-cleavage site between MalE and the expressed protein was replaced by a TEV protease-cleavage site (Kristelly et al., Acta Crystallogr D Biol Crystallogr. 59, 1859-1862, 2003). The TeI4h* RT is a derivative of the native TeI4h RT with the YAGD motif in RT-5 changed to YADD. Recombinant plasmids containing group II introns from *T. elongatus* strain BP1 cloned in pET11 (TeI4f), pUC19 (TeI4c), or pACD2X (TeI4h*) were described previously. pMalE-RT plasmids were derived from these initial constructs by PCR amplifying the RT ORF with primers that append restriction sites, and then cloning the PCR products into the corresponding sites of pMal-c2t (TeI4c RT, EcoRI and PstI sites; TeI4f RT, BamHI site; TeI4h* RT, BamHI and PstI sites). Recombinant plasmids denoted pMalE-RF-protein (e.g., pMalE-RF-TeI4c) were derived from the corresponding pMalE-RT plasmids by replacing the TEV-protease cleavable linker (TVDEALKDAQTNS$_3$N$_{10}$LENLYFQG; SEQ ID NO: 19) with a rigid linker (TVDAALAAAQTAAAAA; SEQ ID NO: 20) by the QuikChange PCR procedure using the Accuprime polymerase (Invitrogen, Makarova et al., BioTechniques 29, 970-972, 2000).

Derivatives of pMalE-RF-TeI4c with different linkers were constructed by PCR mutagenesis using the QuikChange procedure. The MalE tag was fused to the C-terminus of the TeI4c ORF in pMal-c2t by amplifying the MalE segment of pMal-c2t with primers that introduce a 5' EcoRI site and a 3' PstI site, and the TeI4c ORF of pMalE-TeI4c with gene specific primers that introduce a 5' NdeI site and a 3' EcoRI site, respectively, and cloning the fragments into pMal-c2t digested with NdeI and PstI.

pNusA-RF-TeI4c-His, which expresses the TeI4c RT with an N-terminal NusA tag fused to the protein via a rigid linker and a C-terminal His6 tag, was constructed by PCR amplifying the TeI4c RT ORF from pMAL-TeI4c with primers that append SacII and KpnI sites and cloning the resulting PCR product between the corresponding sites of pET-50b(+) (Novagen). PCR mutagenesis was then used to replace the last two charged residues (D and E) of NusA, the existing linker, and one of the two N-terminal His6 tags (NICWF-GDEATSGSGH$_6$; SEQ ID NO: 26) with a rigid linker sequence (NICWFGAAAAA; SEQ ID NO: 27). The second N-terminal His6 tag was removed by PCR mutagenesis and a His6 tag was fused to the C-terminus of TeI4c RT by QuikChange PCR.

pMalE-GsI1 and pMalE-GsI2 were constructed by PCR amplifying the RT ORFs from *G. stearothermophilus* strain 10 genomic DNA (obtained from Greg Davis (SigmaAldrich)) by PCR with primers that amplify the introns and appended BamHI and XbaI sites (GsI1) or BamHI sites (GsI2) and then cloning the PCR products between the corresponding sites of pMal-c2t. GsI1 is a subgroup IIB2 intron that is inserted in the *G. stearothermophilus* recA gene and is related to the previously described RT-encoding group II introns in the recA genes of *Geobacillus kaustophilus* (Chee et al., Gene 363, 211-220, 2005) and *Bacillus caldolyticus* (Ng et al., Gene 393, 137-144, 2007). The cloned GsI1 RT ORF was verified to correspond to the genomic sequence (CP001794). GsI2 is a group IIC intron found in multiple copies in the *G. stearothermophilus* genome. The cloned GsI2 RT ORF corresponds to the genomic sequence of one of six full-length copies of GsI2 in the *G. stearothermophilus* genome (CP001794) and has three amino acid sequence changes from the RT ORF cloned by Vellore et al. (Appl. Environ. Microbiol. 70, 7140-7147, 2004). The corresponding pMalE-RF-RT constructs were derived from the pMalE-RT constructs by QuikChange PCR, as described above.

pMalE-LtrA was constructed by PCR amplifying the LtrA ORF of pImp-2 (Saldanha et al., Biochemistry 38, 9069-9083, 1999) using primers that append BamHI and HindIII sites and then cloning the PCR product between the corresponding sites of pMal-c2t, and pMalE-RF-LtrA was derived from pMalE-LtrA by QuikChange PCR, as described above.

Example 2: Protein Purification

For expression of pMalE-RT or pMalE-RF-RT constructs, *E. coli* Rosetta 2/pRARE (Novagen, EMD Biosciences, Gibbstown N.J.) or ScarabXpress/pRARE T7lac (Scarabgenomics, Madison Wis.) were transformed with the expression plasmid and grown at 37° C. in TB or LB medium to mid-log phase (O.D.$_{600}$=0.8). Expression was induced either by adding isopropyl β-D-1-thiogalactopyranoside (IPTG; 1 mM final) to mid-log phase cells (pMalE-RF-TeI4c, TeI4f, TeI4h*, GsI1, and GsI2) or by growing cells in autoinduction medium (LB containing 0.2% lactose, 0.05% glucose, 0.5% glycerol, 24 mM (NH$_4$)$_2$SO$_4$, 50 mM KH$_2$PO$_4$, 50 mM Na$_2$HPO$_4$) (pMalE-LtrA and pMalE-RF-LtrA). In either case, induction was for ~24 h at 18-25° C., after which cells were pelleted by centrifugation, resuspended in buffer A (20 mM Tris-HCl, pH 7.5, 0.5 M KCl or NaCl, 1 mM EDTA, 1 mM dithiothreitol (DTT)), and frozen at −80° C.

For purification of MalE-RF-TeI4c, TeI4f, TeI4h* and their derivatives, the cell suspension was thawed, treated with lysozyme (1 mg/ml; Sigma) for 15 min on ice, freezethawed three times on dry ice, sonicated (Branson 450 Sonifier, Branson Ultrasonics, Danbury Conn.) three or four 10 sec bursts or one 30 sec burst on ice at an amplitude of 60%, with 10 sec between bursts, and centrifuged for 30 min at 18,500×g at 4° C. Nucleic acids were precipitated by adding polyethyleneimine (PEI) to a final concentration of 0.1% and centrifuging for 15 min at 15,000×g at 4° C. in a J16.25 rotor in an Avanti J-E centrifuge (Beckman Coulter, Brea Calif.). The resulting supernatant was applied to an amylose column (10-ml column volume; Amylose HighFlow (New England Biolabs), equilibrated in buffer A), which was washed with five column volumes each of buffer A containing 0.5 M, 1.5 M, or 0.5 M KCl, and then eluted with buffer A containing 10 mM maltose. Protein fractions were pooled and purified further via a heparin-Sepharose column (3 tandem 1-ml columns; GE Healthcare Biosciences Corp.) which had been pre-equilibrated in 20 mM Tris-HCl, pH 7.5 containing KCl (100 mM for MalE-RF-4-c, 4f, 4h*, MalE-LtrA and MalE-RF-LtrA; 50 mM for MalE-RF-GsI1 or GsI2), 1 mM EDTA, 1 mM DTT, 10% glycerol. The proteins were applied to the column in the same buffer and eluted with a 40-column volume gradient from the loading concentration to 2 M KCl. The proteins eluted at ~800 mM KCl. The peak fractions were pooled and dialyzed against 20 mM Tris-HCl, pH 7.5, 0.5 M KCl, 1 mM EDTA, 1 mM DTT, and 50% glycerol for storage. The frozen proteins showed no decrease in RT activity for at least six months.

The MalE-RF-GsI1 protein, which has an N-terminal MalE tag and a C-terminal His6-tag, was purified similarly, except that nucleic acids were precipitated with 0.2% PEI, and the protein eluted from the amylose column was purified further on a nickel column prior to the final heparinSepharose column. The nickel column (5 ml HisTrap™ HP Nickel Sepharose; GE Healthcare Biosciences, Piscataway N.J.) equilibrated with binding buffer (500 mM KCl, 20 mM Tris-HCl pH 7.5, 40 mM imidazole, and 10% glycerol) was loaded with pooled protein fractions from the amylose column, washed with 10 column volumes of binding buffer, eluted with five column volumes of elution buffer (500 mM KCl, 20 mM Tris-HCl pH 7.5, 400 mM imidazole and 10% glycerol), and the supernatant loaded directly onto the heparin-Sepharose column. The peak fractions from the heparin-Sepharose column were pooled, dialyzed against 20 mM Tris-HCl, pH 7.5, 0.5 M KCl, 50% glycerol, and stored as described above.

For the NusA fusions, *E. coli* ScarabXpress/pRARE T7lac cells were induced with 0.5 mM IPTG for 48 h at 18° C. and resuspended in nickel buffer A (20 mM Tris pH 7.5, 500 mM KCl, 30 mM imidazole, 10% glycerol). After disrupting the cells as described above, nucleic acids were precipitated from the lysate by adding a final concentration of 0.2% polyethyleneimine, followed by centrifugation at 10,000×g for 15 min. The supernatant was applied to a 5-ml nickelSepharose column pre-equilibrated with nickel buffer A, and then eluted with nickel buffer A containing 500 mM imidazole. The protein fractions were pooled and loaded directly onto two connected 1-ml heparin-Sepharose columns that had been pre-equilibrated in 20 mM Tris pH 7.5, 100 mM KCl, 1 mM DTT, 1 mM EDTA, and 20% glycerol. The protein was eluted with a 20-column volume gradient of 0.1 to 1.5 M KCl, and peak fractions were pooled, dialyzed against 20 mM Tris-HCl, pH 7.5, 0.5 M KCl, 1 mM EDTA, 1 mM DTT, 50% glycerol, and stored as described above.

Example 3: Reverse Transcriptase Assays

RT activity at different temperatures was assayed by quantifying incorporation of $^{32}$P-dTTP using poly(rA)/oligo $(dT)_{42}$ as the template-primer. The RT (50 nM MalE-RF-TeI4c RT or 100 nM of all other RTs) was pre-incubated with 100 nM poly(rA)/oligo$(dT)_{42}$ in 1×RT buffer (75 mM KCl, 10 mM MgCl$_2$, 20 mM Tris-HCl, pH 7.5, and 1 mM DTT) at different temperatures (ranging from 25-77° C.), and reactions were initiated by adding 5 µCi [α-$^{32}$P]-dTTP (3,000 Ci/mmol; Perkin Elmer, Waltham Mass.). The reactions were incubated for times within the linear range and stopped by adding EDTA to a final concentration of 250 mM. Reaction products were spotted onto Whatman DE81 chromatography paper (10×7.5-cm sheets; GE Healthcare), washed 3 times in 0.3 M NaCl and 0.03 M sodium citrate, and scanned with a PhosphorImager (Typhoon Trio Variable Mode Imager; GE Healthcare) to quantify bound radioactivity.

Other RT assays used RNA templates with annealed DNA oligonucleotide primers. The RNA template was either a 531-nt in vitro transcript synthesized from pBluescript KS (+) digested with AflIII transcribed using T7 Megscript kits (Ambion, Applied Biosystems, Austin, Tex.) or a 1.2-kb kanR RNA purchased from Promega (Promega, Madison Wis.). In vitro transcription was done according to the manufacturer's instructions for 4 h at 37° C. After digesting the DNA template with Turbo DNase I (5 min, 37° C.), RNAs were extracted with phenol:chloroform:isoamyl alcohol (25:24:1; phenol-CIA) and purified by two cycles of gel filtration through Sephadex G-50 (Sigma, St Louis, Mo.) spin columns. The RNA concentration was determined by using a Nanodrop (Thermo Scientific, Wilmington, Del.). RNAs were stored in Milli-Q-grade H$_2$O and stored at −20° C.

DNA oligonucleotide primers complementary to the 3' ends of the RNAs were synthesized by IDT (Coralville, Iowa; AflIII primer: 5'-CCGCCTTTGAGTGAGCTGA-TACCGCTCGCCGCAGCCG; SEQ ID NO: 28; P078 Kanamycin Rev 5'-GGTGGACCAGTTGGTGATTTT-GAACTTTTGCTTTGCCACGGAAC; SEQ ID NO: 29). Primer concentrations were determined by A$_{260}$. The primers were 5' $^{32}$P-labeled with T4 polynucleotide kinase (New England Biolabs) according to the manufacturer's instructions, and free nucleotides were removed by gel filtration through a Sephadex G-25 column. The primers were mixed with the template at a molar ratio of 1.0:1.1 and annealed by heating to 82° C. for 2 min and then cooling to room temperature in a GeneAmp 9700 PCR cycler with the ramp setting of 10%.

For gel analysis of cDNA synthesis, 100 nM of annealed template/primer was incubated with 200 nM enzyme in 100 mM KCl, 20 mM Tris HCl pH 7.5, 10 mM MgCl$_2$ and 1 mM DTT for MalE-RF-TeI4c RT and in 10 mM NaCl, 20 mM Tris HCl pH 7.5, 10 mM MgCl$_2$ and 1 mM DTT for MalE-RF-GsI2 RT. Reactions were initiated by adding dNTPs and MgCl$_2$ to final concentrations of 1.25 mM and 10 mM, respectively, incubated for 30 min at the indicated temperature, and terminated by adding 0.1% SDS/250 mM EDTA (final concentrations) followed by phenol-CIA extraction. The products were analyzed by electrophoresis in a denaturing 6% polyacrylamide gel, which was dried and quantified with a PhosphorImager. A 5'-labeled 10-bp ladder (Invitrogen™) was used as size markers.

Example 4: Quantitative Real-Time Polymerase Chain Reaction (qPCR)

cDNAs for qPCR analysis were generated in 20 µl reactions containing 1×RT buffer (75 mM KCl, 10 mM MgCl$_2$, 20 mM Tris-HCl, pH 7.5), 1 mM DTT, 5×10$^8$ copies of kanR RNA, 200 nM MalE-RF-TeI4c RT and 1 mM dNTPs for 30 min at temperatures specified for individual experiments. Parallel reactions with SuperScript III (Invitrogen) were done according to the manufacturers specifications. Reactions were incubated at the different temperatures for 2 min and started by adding dNTPs. After incubating for 30 min, the reactions were quickly frozen on dry ice to stop the reactions. 5 µl of cDNA reaction were used for the qPCR.

qPCR analysis was done in 96-well plates with optical caps with each well containing 25 µl of reaction mix consisting of 12.5 µl of 2×TaqMan® Gene Expression Master Mix (Applied Biosystems, Foster City, Calif.), 7.5 µl of forward, reverse, and dual-labeled probe mix (oligonucleotides purchased individually from Integrated DNA Technologies, Coralville, Iowa), and 5 µl cDNA template. The mixture was incubated in the 7900HT Fast Real-Time PCR System (Applied Biosystems), using the 9600 emulation mode protocol (50° C. for 2 min, 95° C. for 10 min, then cycled for a total of 45 cycles at 95° C. for 15 sec and 60° C. for 60 sec). Data were collected and analyzed using the Applied Biosystems Sequence Detection System Software, Versions 2.2 or 2.3.

The Novagen® double-stranded DNA plasmid vector pET9a (EMD Chemicals) was used to quantitate kanR cDNA levels. The pET9a vector contains the kanR coding sequence (bases 3523-4335) and has 100% sequence homology at each primer/probe binding site with the Promega 1.2-kb kanR RNA. Purified and quantitated pET9a DNA vector was initially diluted to 1×10$^9$ copies/µl stock aliquots and stored at −20° C. For each run, fresh stocks were thawed and then serially diluted to generate a quantitative standard curve used in qPCR. Cycle threshold results for cDNA samples were then plotted against the standard curve to determine copy numbers equivalents.

Primers used were:

P078 Kanamycin RT-1107R

SEQ ID NO: 29
5'-GGTGGACCAGTTGGTGATTTTGAACTTTTGCTTTGCCACGGAAC-3';
(Tm = 80° C.)

primer sets nt 188-257:

Forward--P029 kan-188F:

SEQ ID NO: 30
5'-GGGTATAAATGGGCTCGCG-3';

```
Reverse--P030 kan-257R:
                                     SEQ ID NO: 31
5'-CGGGCTTCCCATACAATCG-3';

Taqman Probe--P031 kan-213T:
                                     SEQ ID NO: 32
5'(6-carboxyfluorescein (6FAM))-TCGGGCAATCAGGTGCGACAATC-3';
(Iowa Black FQ; a dark non-fluorescent quencher);
```

Amplicon 70 bp:

```
                                     SEQ ID NO: 33
5'GGGTATAAATGGGCTCGCGATAATGTCGGGCAATCAGGTGCGAC

AATCTATCGATTGTATGGGAAGCCCG-3';
```

Primer Set (nt 562-634):

```
Forward--P001 kan-562F:
                                     SEQ ID NO: 34
5'-CGCTCAGGCGCAATCAC-3';

Reverse--P002 kan-634R:
                                     SEQ ID NO: 35
5'-CCAGCCATTACGCTCGTCAT-3';

Taqman Probe--P003 kan-581T:
                                     SEQ ID NO: 36
5'(6-FAM)-ATGAATAACGGTTTGGTTGATGCGAGTGA-3'-(TAMRA);
```

Amplicon 73 bp

```
                                     SEQ ID NO: 37
5'CGCTCAGGCGCAATCACGAATGAATAACGGTTTGGTTGATGCGA

GTGATTTTGATGACGAGCGTAATGGCTGG-3';
```

Example 5: Retrohoming Assays

Retrohoming assays were done in K coli HMS174(DE3) (Novagen™) grown on LB medium, with antibiotics added at the following concentrations: ampicillin, 100 µg/ml; chloramphenicol, 25 µg/ml; tetracycline, 25 µg/ml. The intron-donor plasmids, derivatives of pACD2X (San Filippo et al., Journal of Molecular Biology, 324, 933-951, 2002), carry a $cap^R$ marker and use a T7lac promoter to express a ΔORF intron (I-ΔORF) with short flanking 5' and 3' exons (E1 and E2, respectively) and a T7 promoter in DIV, followed by the RT ORF downstream of E2. The recipient plasmids, derivatives of pBRR-tet (Guo et al., Science 289, 452-457, 2000; Karberg et al., Nature Biotech. 19, 1162-1167, 2001), carry an $amp^R$ marker and contain a target site for the intron (ligated E1-E2 sequences) cloned upstream of a promoterless $tet^R$ gene. The latter is activated by insertion of the intron carrying the T7 promoter, enabling selection for $Tet^R+Amp^R$ colonies. For the assays, cells were co-transformed with the $Cap^R$ donor and $Amp^R$ recipient plasmids, inoculated into 5 ml of LB medium containing chloramphenicol and ampicillin, and grown with shaking (200 rpm) overnight at 37° C. A small portion (50 µl) of the overnight culture was inoculated into 5 ml of fresh LB medium containing the same antibiotics and grown for 1 h as above. The cells were then induced with IPTG for 1 h under conditions specified in the legend of Table 1 for individual experiments. The cultures were then placed on ice, diluted with ice-cold LB, and plated at different dilutions onto LB agar containing ampicillin or ampicillin+tetracycline. After incubating the plates overnight at 37° C., the mobility efficiency was calculated as the ratio of $(Tet^R+Amp^R)/Amp^R$ colonies.

---

What is claimed is:

1. A stabilized reverse transcriptase fusion protein comprising a thermostable group-II intron-derived reverse transcriptase connected at its N-terminus by a linker peptide to the C-terminus of a stabilizer protein including 50 or more amino acids, wherein the fusion protein exhibits increased solubility and stability in solution.

2. The stabilized reverse transcriptase fusion protein of claim 1, wherein the thermostable reverse transcriptase is a *Thermosynechococcus elongatus* reverse transcriptase, or *Geobacillus stearothermophilus* reverse transcriptase.

3. The stabilized reverse transcriptase fusion protein of claim 1, wherein the thermostable reverse transcriptase comprises a polypeptide with at least 85% amino acid sequence identity to a sequence selected from the group consisting of SEQ ID NO: 1, SEQ ID NO: 2, SEQ ID NO: 3, SEQ ID NO: 4, or SEQ ID NO: 5.

4. The stabilized reverse transcriptase fusion protein of claim 1, wherein the stabilizer protein comprises an affinity protein or a solubility-enhancing protein.

5. The stabilized reverse transcriptase fusion protein of claim 4, wherein the stabilizer protein comprises a maltose binding protein or an N-utilization substance A protein.

6. The stabilized reverse transcriptase fusion protein of claim 4, wherein the stabilizer protein has been modified by replacing charged amino acids with uncharged amino acids.

7. The stabilized reverse transcriptase fusion protein of claim 1, wherein the linker peptide is a non-cleavable linker peptide.

8. The stabilized reverse transcriptase fusion protein of claim 7, wherein the non-cleavable linker peptide is a rigid linker peptide.

9. The stabilized reverse transcriptase fusion protein of claim 7, wherein the linker peptide consists of 1 to 20 amino acids.

10. The stabilized reverse transcriptase fusion protein of claim 7, wherein the linker peptide consists of 1 to 5 amino acids.

11. The stabilized reverse transcriptase fusion protein of claim 7, wherein the linker peptide consists of 3 to 5 amino acids.

12. The stabilized reverse transcriptase fusion protein of claim 8, wherein the rigid linker peptide consists of SEQ ID NO: 12.

13. The stabilized reverse transcriptase fusion protein of claim 1, wherein the fusion protein has an amino acid sequence comprising a polypeptide with at least 85% amino acid sequence identity to a sequence selected from the group consisting of SEQ ID NO: 6, SEQ ID NO: 7, SEQ ID NO: 8, SEQ ID NO: 9, or SEQ ID NO: 10.

14. The stabilized reverse transcriptase fusion protein of claim 1, wherein the stabilized reverse transcriptase fusion protein is capable of carrying out reverse transcription with an error frequency of $2.0 \times 10^{-5}$ or less at a temperature from about 45° to about 65° C.

15. A stabilized reverse transcriptase fusion protein comprising a thermostable group-II intron-derived reverse transcriptase connected at its N-terminus by a linker peptide to the C-terminus of a stabilizer protein including 50 or more amino acids, wherein the fusion protein exhibits increased solubility and stability in solution.

16. The stabilized reverse transcriptase fusion protein of claim 1, wherein the stabilizer protein includes an independent folding domain and/or does not fold into long-lived misfolded intermediates.

* * * * *

UNITED STATES PATENT AND TRADEMARK OFFICE
CERTIFICATE OF CORRECTION

PATENT NO. : 10,113,156 B2
APPLICATION NO. : 13/254223
DATED : October 30, 2018
INVENTOR(S) : Lambowitz et al.

Page 1 of 1

It is certified that error appears in the above-identified patent and that said Letters Patent is hereby corrected as shown below:

In the Claims

Column 120, Line 65 to Column 121, Line 3, cancel the text in Line 67 of Claim 15 that recites "by a linker peptide"

Signed and Sealed this
Fifth Day of May, 2020

Andrei Iancu
*Director of the United States Patent and Trademark Office*

SEQUENCE LISTING

```
<160> NUMBER OF SEQ ID NOS: 46

<210> SEQ ID NO 1
<211> LENGTH: 562
<212> TYPE: PRT
<213> ORGANISM: Thermosynechococcus elongatus

<400> SEQUENCE: 1

Met Glu Thr Arg Gln Met Thr Val Asp Gln Thr Thr Gly Ala Val Thr
1               5                   10                  15

Asn Gln Thr Glu Thr Ser Trp His Ser Ile Asn Trp Thr Lys Ala Asn
            20                  25                  30

Arg Glu Val Lys Arg Leu Gln Val Arg Ile Ala Lys Ala Val Lys Glu
        35                  40                  45

Gly Arg Trp Gly Lys Val Lys Ala Leu Gln Trp Leu Leu Thr His Ser
    50                  55                  60

Phe Tyr Gly Lys Ala Leu Ala Val Lys Arg Val Thr Asp Asn Ser Gly
65                  70                  75                  80

Ser Arg Thr Pro Gly Val Asp Gly Ile Thr Trp Ser Thr Gln Glu Gln
                85                  90                  95
```

-continued

```
Lys Thr Gln Ala Ile Lys Ser Leu Arg Arg Gly Tyr Lys Pro Gln
                100                 105                 110

Pro Leu Arg Arg Val Tyr Ile Pro Lys Ala Asn Gly Lys Gln Arg Pro
            115                 120                 125

Leu Gly Ile Pro Thr Met Lys Asp Arg Ala Met Gln Ala Leu Tyr Ala
        130                 135                 140

Leu Ala Leu Glu Pro Val Ala Glu Thr Thr Ala Asp Arg Asn Ser Tyr
145                 150                 155                 160

Gly Phe Arg Arg Gly Arg Cys Thr Ala Asp Ala Ala Gly Gln Cys Phe
                165                 170                 175

Leu Ala Leu Ala Lys Ala Lys Ser Ala Glu His Val Leu Asp Ala Asp
            180                 185                 190

Ile Ser Gly Cys Phe Asp Asn Ile Ser His Glu Trp Leu Leu Ala Asn
        195                 200                 205

Thr Pro Leu Asp Lys Gly Ile Leu Arg Lys Trp Leu Lys Ser Gly Phe
    210                 215                 220

Val Trp Lys Gln Gln Leu Phe Pro Thr His Ala Gly Thr Pro Gln Gly
225                 230                 235                 240

Gly Val Ile Ser Pro Val Leu Ala Asn Ile Thr Leu Asp Gly Met Glu
                245                 250                 255

Glu Leu Leu Ala Lys His Leu Arg Gly Gln Lys Val Asn Leu Ile Arg
            260                 265                 270

Tyr Ala Asp Asp Phe Val Val Thr Gly Lys Asp Glu Thr Leu Glu
        275                 280                 285

Lys Ala Arg Asn Leu Ile Gln Glu Phe Leu Lys Glu Arg Gly Leu Thr
    290                 295                 300

Leu Ser Pro Glu Lys Thr Lys Ile Val His Ile Glu Glu Gly Phe Asp
305                 310                 315                 320

Phe Leu Gly Trp Asn Ile Arg Lys Tyr Asn Gly Val Leu Leu Ile Lys
                325                 330                 335

Pro Ala Lys Lys Asn Val Lys Ala Phe Leu Lys Lys Ile Arg Asp Thr
            340                 345                 350

Leu Arg Glu Leu Arg Thr Ala Thr Gln Glu Ile Val Ile Asp Thr Leu
        355                 360                 365

Asn Pro Ile Ile Arg Gly Trp Ala Asn Tyr His Lys Gly Gln Val Ser
    370                 375                 380

Lys Glu Thr Phe Asn Arg Val Asp Phe Ala Thr Trp His Lys Leu Trp
385                 390                 395                 400

Arg Trp Ala Arg Arg His Pro Asn Lys Pro Ala Gln Trp Val Lys
                405                 410                 415

Asp Lys Tyr Phe Ile Lys Asn Gly Ser Arg Asp Trp Val Phe Gly Met
            420                 425                 430

Val Met Lys Asp Lys Asn Gly Glu Leu Arg Thr Lys Arg Leu Ile Lys
        435                 440                 445

Thr Ser Asp Thr Arg Ile Gln Arg His Val Lys Ile Lys Ala Asp Ala
    450                 455                 460

Asn Pro Phe Leu Pro Glu Trp Ala Glu Tyr Phe Glu Lys Arg Lys Lys
465                 470                 475                 480

Leu Lys Lys Ala Pro Ala Gln Tyr Arg Arg Ile Arg Arg Glu Leu Trp
                485                 490                 495

Lys Lys Gln Gly Gly Ile Cys Pro Val Cys Gly Gly Glu Ile Glu Gln
            500                 505                 510
```

```
Asp Met Leu Thr Asp Ile His His Ile Leu Pro Lys His Lys Gly Gly
            515                 520                 525

Ser Asp Asp Leu Asp Asn Leu Val Leu Ile His Ala Asn Cys His Lys
            530                 535                 540

Gln Val His Ser Arg Asp Gly Gln His Ser Arg Ser Leu Leu Lys Glu
545                 550                 555                 560

Gly Leu

<210> SEQ ID NO 2
<211> LENGTH: 562
<212> TYPE: PRT
<213> ORGANISM: Thermosynechococcus elongatus

<400> SEQUENCE: 2

Met Glu Thr Arg Gln Met Ala Val Gln Thr Thr Gly Ala Val Thr
1               5                   10                  15

Asn Gln Thr Glu Thr Ser Trp His Ser Ile Asp Trp Ala Lys Ala Asn
            20                  25                  30

Arg Glu Val Lys Arg Leu Gln Val Arg Ile Ala Lys Ala Val Lys Glu
            35                  40                  45

Gly Arg Trp Gly Lys Val Lys Ala Leu Gln Trp Leu Leu Thr His Ser
50                  55                  60

Phe Tyr Gly Lys Ala Leu Ala Val Lys Arg Val Thr Asp Asn Ser Gly
65                  70                  75                  80

Ser Lys Thr Pro Gly Val Asp Gly Ile Thr Trp Ser Thr Gln Glu Gln
            85                  90                  95

Lys Ala Gln Ala Ile Lys Ser Leu Arg Arg Arg Gly Tyr Lys Pro Gln
            100                 105                 110

Pro Leu Arg Arg Val Tyr Ile Pro Lys Ala Asn Gly Lys Gln Arg Pro
            115                 120                 125

Leu Gly Ile Pro Thr Met Lys Asp Arg Ala Met Gln Ala Leu Tyr Ala
130                 135                 140

Leu Ala Leu Glu Pro Val Ala Glu Thr Thr Ala Asp Arg Asn Ser Tyr
145                 150                 155                 160

Gly Phe Arg Arg Gly Arg Cys Ile Ala Asp Ala Ala Thr Gln Cys His
            165                 170                 175

Ile Thr Leu Ala Lys Thr Asp Arg Ala Gln Tyr Val Leu Asp Ala Asp
            180                 185                 190

Ile Ala Gly Cys Phe Asp Asn Ile Ser His Glu Trp Leu Leu Ala Asn
            195                 200                 205

Ile Pro Leu Asp Lys Arg Ile Leu Arg Lys Trp Leu Lys Ser Gly Phe
210                 215                 220

Val Trp Lys Gln Gln Leu Phe Pro Ile His Ala Gly Thr Pro Gln Gly
225                 230                 235                 240

Gly Val Ile Ser Pro Met Leu Ala Asn Met Thr Leu Asp Gly Met Glu
            245                 250                 255

Glu Leu Leu Asn Lys Phe Pro Arg Ala His Lys Val Lys Leu Ile Arg
            260                 265                 270

Tyr Ala Asp Asp Phe Val Val Thr Gly Glu Thr Lys Glu Val Leu Tyr
            275                 280                 285

Ile Ala Gly Ala Val Ile Gln Ala Phe Leu Lys Glu Arg Gly Leu Thr
            290                 295                 300

Leu Ser Lys Glu Lys Thr Lys Ile Val His Ile Glu Glu Gly Phe Asp
305                 310                 315                 320
```

Phe Leu Gly Trp Asn Ile Arg Lys Tyr Asp Gly Lys Leu Ile Lys
                    325                 330                 335

Pro Ala Lys Lys Asn Val Lys Ala Phe Leu Lys Lys Ile Arg Asp Thr
                340                 345                 350

Leu Arg Glu Leu Arg Thr Ala Pro Gln Glu Ile Val Ile Asp Thr Leu
            355                 360                 365

Asn Pro Ile Ile Arg Gly Trp Thr Asn Tyr His Lys Asn Gln Ala Ser
370                 375                 380

Lys Glu Thr Phe Val Gly Val Asp His Leu Ile Trp Gln Lys Leu Trp
385                 390                 395                 400

Arg Trp Ala Arg Arg His Pro Ser Lys Ser Val Arg Trp Val Lys
                405                 410                 415

Ser Lys Tyr Phe Ile Gln Ile Gly Asn Arg Lys Trp Met Phe Gly Ile
                420                 425                 430

Trp Thr Lys Asp Lys Asn Gly Asp Pro Trp Ala Lys His Leu Ile Lys
                435                 440                 445

Ala Ser Glu Ile Arg Ile Gln Arg Arg Gly Lys Ile Lys Ala Asp Ala
            450                 455                 460

Asn Pro Phe Leu Pro Glu Trp Ala Glu Tyr Phe Glu Gln Arg Lys Lys
465                 470                 475                 480

Leu Lys Glu Ala Pro Ala Gln Tyr Arg Arg Thr Arg Arg Glu Leu Trp
                485                 490                 495

Lys Lys Gln Gly Gly Ile Cys Pro Val Cys Gly Gly Glu Ile Glu Gln
            500                 505                 510

Asp Met Leu Thr Glu Ile His His Ile Leu Pro Lys His Lys Gly Gly
            515                 520                 525

Thr Asp Asp Leu Asp Asn Leu Val Leu Ile His Thr Asn Cys His Lys
530                 535                 540

Gln Val His Asn Arg Asp Gly Gln His Ser Arg Phe Leu Leu Lys Glu
545                 550                 555                 560

Gly Leu

<210> SEQ ID NO 3
<211> LENGTH: 562
<212> TYPE: PRT
<213> ORGANISM: Thermosynechococcus elongatus

<400> SEQUENCE: 3

Met Glu Thr Arg Gln Met Ala Val Glu Gln Thr Thr Gly Ala Val Thr
1               5                   10                  15

Asn Gln Thr Glu Thr Ser Trp His Ser Ile Asp Trp Ala Lys Ala Asn
                20                  25                  30

Arg Glu Val Lys Arg Leu Gln Val Arg Ile Ala Lys Ala Val Lys Glu
            35                  40                  45

Gly Arg Trp Gly Lys Val Lys Ala Leu Gln Trp Leu Leu Thr His Ser
        50                  55                  60

Phe Tyr Gly Lys Ala Leu Ala Val Lys Arg Val Thr Asp Asn Ser Gly
65                  70                  75                  80

Ser Lys Thr Pro Gly Val Asp Gly Ile Thr Trp Ser Thr Gln Glu Gln
                85                  90                  95

Lys Ala Gln Ala Ile Lys Ser Leu Arg Arg Gly Tyr Lys Pro Gln
            100                 105                 110

Pro Leu Arg Arg Val Tyr Ile Pro Lys Ala Ser Gly Lys Gln Arg Pro
        115                 120                 125

```
Leu Gly Ile Pro Thr Thr Lys Asp Arg Ala Met Gln Ala Leu Tyr Ala
130                 135                 140

Leu Ala Leu Glu Pro Val Ala Glu Thr Thr Ala Asp Arg Asn Ser Tyr
145                 150                 155                 160

Gly Phe Arg Gln Gly Arg Cys Thr Ala Asp Ala Ala Gly Gln Cys Phe
                165                 170                 175

Thr Val Leu Gly Arg Ser Asp Cys Ala Lys Tyr Ile Leu Asp Ala Asp
            180                 185                 190

Ile Thr Gly Cys Phe Asp Asn Ile Ser His Glu Trp Leu Leu Asp Asn
        195                 200                 205

Ile Pro Leu Asp Lys Glu Val Leu Arg Lys Trp Leu Lys Ser Gly Phe
210                 215                 220

Val Trp Lys Gln Gln Leu Phe Pro Thr His Ala Gly Thr Pro Gln Gly
225                 230                 235                 240

Gly Val Ile Ser Pro Met Leu Ala Asn Met Thr Leu Asp Gly Met Glu
                245                 250                 255

Glu Leu Leu Lys Lys His Leu Arg Lys Gln Lys Val Asn Leu Ile Arg
            260                 265                 270

Tyr Ala Asp Asp Phe Val Val Thr Gly Glu Ser Lys Glu Thr Leu Glu
        275                 280                 285

Lys Val Thr Thr Val Ile Gln Glu Phe Leu Lys Glu Arg Gly Leu Thr
290                 295                 300

Leu Ser Glu Glu Lys Thr Lys Val Val His Ile Glu Glu Gly Phe Asp
305                 310                 315                 320

Phe Leu Gly Trp Asn Ile Arg Lys Tyr Gly Glu Lys Leu Leu Ile Lys
                325                 330                 335

Pro Ala Lys Lys Asn Ile Lys Ala Phe His Lys Lys Ile Arg Asp Ala
            340                 345                 350

Leu Lys Glu Leu Arg Thr Ala Thr Gln Glu Ala Val Ile Asp Thr Leu
        355                 360                 365

Asn Pro Ile Ile Lys Gly Trp Ala Asn Tyr His Arg Asn Gln Val Ser
370                 375                 380

Lys Arg Ile Phe Asn Arg Ala Asp Asp Asn Ile Trp His Lys Leu Trp
385                 390                 395                 400

Arg Trp Ala Lys Arg Arg His Pro Asn Lys Pro Ala Arg Trp Thr Lys
                405                 410                 415

Asn Lys Tyr Phe Ile Lys Ile Gly Asn Arg His Trp Val Phe Gly Thr
            420                 425                 430

Trp Lys Lys Asp Lys Glu Gly Arg Leu Arg Ser Arg Tyr Leu Ile Lys
        435                 440                 445

Ala Gly Asp Thr Arg Ile Gln Arg His Val Lys Ile Lys Ala Asp Ala
450                 455                 460

Asn Pro Phe Leu Pro Glu Trp Ala Glu Tyr Phe Glu Glu Arg Lys Lys
465                 470                 475                 480

Leu Lys Glu Ala Pro Ala Gln Tyr Arg Ile Arg Arg Glu Leu Trp
                485                 490                 495

Lys Lys Gln Gly Gly Ile Cys Pro Val Cys Gly Gly Glu Ile Glu Gln
            500                 505                 510

Asp Met Leu Thr Glu Ile His His Ile Leu Pro Lys His Lys Gly Gly
        515                 520                 525

Ser Asp Asp Leu Asp Asn Leu Val Leu Ile His Ala Asn Cys His Lys
530                 535                 540

Gln Val His Ser Arg Asp Gly Gln His Ser Arg Phe Leu Leu Lys Glu
```

<210> SEQ ID NO 4
<211> LENGTH: 635
<212> TYPE: PRT
<213> ORGANISM: Geobacillus stearothermophilus

<400> SEQUENCE: 4

```
Met Lys Val Asn Lys Leu Val Val Lys Ser Glu Gln Asp Leu Arg Asn
1               5                   10                  15

Cys Leu Asp Leu Leu Tyr Gln Glu Ala Lys Lys Gly Lys His Phe Tyr
            20                  25                  30

Gly Met Leu Glu Leu Leu Gln Asn Asp Val Val Ile Leu Glu Ala Ile
        35                  40                  45

Arg Asn Ile Lys Ser Asn Lys Gly Ser Lys Thr Ala Gly Ile Asp Gln
    50                  55                  60

Lys Ile Val Asp Asp Tyr Leu Leu Met Pro Thr Glu Lys Val Phe Gly
65                  70                  75                  80

Met Ile Lys Ala Lys Leu Asn Asp Tyr Lys Pro Ile Pro Val Arg Arg
                85                  90                  95

Cys Asn Lys Pro Lys Gly Asn Ala Lys Ser Ser Lys Arg Lys Gly Asn
            100                 105                 110

Ser Pro Asn Glu Glu Gly Glu Thr Arg Pro Leu Gly Ile Ser Ala Val
        115                 120                 125

Thr Asp Arg Ile Ile Gln Glu Met Leu Arg Ile Val Leu Glu Pro Ile
    130                 135                 140

Phe Glu Ala Gln Phe Tyr Pro His Ser Tyr Gly Phe Arg Pro Tyr Arg
145                 150                 155                 160

Ser Thr Glu His Ala Leu Ala Trp Met Leu Lys Ile Ile Asn Gly Ser
                165                 170                 175

Lys Leu Tyr Trp Val Val Lys Gly Asp Ile Glu Ser Tyr Phe Asp His
            180                 185                 190

Ile Asn His Lys Lys Leu Leu Asn Ile Met Trp Asn Met Gly Val Arg
        195                 200                 205

Asp Lys Arg Val Leu Cys Ile Val Lys Lys Met Leu Lys Ala Gly Gln
    210                 215                 220

Val Ile Gln Gly Lys Phe Tyr Pro Thr Ala Lys Gly Ile Pro Gln Gly
225                 230                 235                 240

Gly Ile Ile Ser Pro Leu Leu Ala Asn Val Tyr Leu Asn Ser Phe Asp
                245                 250                 255

Trp Met Val Gly Gln Glu Tyr Glu Tyr His Pro Asn Asn Ala Asn Tyr
            260                 265                 270

Arg Glu Lys Lys Asn Ala Leu Ala Ala Leu Arg Asn Lys Gly His His
        275                 280                 285

Pro Val Phe Tyr Ile Arg Tyr Ala Asp Asp Trp Val Ile Leu Thr Asp
    290                 295                 300

Thr Lys Glu Tyr Ala Glu Lys Ile Arg Glu Gln Cys Lys Gln Tyr Leu
305                 310                 315                 320

Ala Cys Glu Leu His Leu Thr Leu Ser Asp Glu Lys Thr Phe Ile Ala
                325                 330                 335

Asp Ile Arg Glu Gln Arg Val Lys Phe Leu Gly Phe Cys Ile Glu Ala
            340                 345                 350

Gly Lys Arg Arg Phe His Lys Lys Gly Phe Ala Ala Arg Met Ile Pro
```

```
                355                 360                 365
Asp Met Glu Lys Val Asn Ala Lys Val Lys Glu Ile Lys Arg Asp Ile
370                 375                 380

Arg Leu Leu Arg Thr Arg Lys Ser Glu Leu Glu Lys Ala Leu Asp Ile
385                 390                 395                 400

Glu Asn Ile Asn Thr Lys Ile Ile Gly Leu Ala Asn His Leu Lys Ile
                405                 410                 415

Gly Ile Ser Lys Tyr Ile Met Gly Lys Val Asp Arg Val Ile Glu Glu
                420                 425                 430

Thr Ala Tyr Arg Thr Trp Val Lys Met Tyr Gly Lys Glu Lys Ala Ala
                435                 440                 445

Gln Tyr Lys Arg Pro Val Ser Glu Phe His Asn Arg Ile Asp Arg His
                450                 455                 460

Lys Gly Tyr Gln Met Lys His Phe Ser Val Val Thr Glu Asp Gly Ile
465                 470                 475                 480

Arg Val Gly Ile Thr His Ala Lys Ile Thr Pro Ile Gln Tyr Ala Thr
                485                 490                 495

Val Phe Lys Gln Glu Met Thr Pro Tyr Thr Ala Asp Gly Arg Lys Met
                500                 505                 510

Tyr Glu Glu Lys His Arg Lys Ile Arg Leu Pro Asp Lys Met Ser Leu
                515                 520                 525

Phe Asp His Asp Ser Ile Phe Ile Tyr Ile Leu Ser Glu His Asn Asp
530                 535                 540

Gly Lys Tyr Asn Leu Glu Tyr Phe Leu Asn Arg Val Asn Val Phe His
545                 550                 555                 560

Arg Asp Lys Gly Lys Cys Lys Ile Cys Ala Val Tyr Leu Ser Pro Gly
                565                 570                 575

Asn Phe His Cys His His Ile Asp Pro Ser Lys Pro Leu Ser Glu Ile
                580                 585                 590

Asn Lys Thr Val Asn Leu Ile Ser Leu Cys Asn Gln Cys His Arg Leu
                595                 600                 605

Val His Ser Asn Gln Glu Pro Pro Phe Thr Glu Arg Lys Met Phe Asp
610                 615                 620

Lys Leu Thr Lys Tyr Arg Asn Lys Leu Lys Ile
625                 630                 635

<210> SEQ ID NO 5
<211> LENGTH: 420
<212> TYPE: PRT
<213> ORGANISM: Geobacillus stearothermophilus

<400> SEQUENCE: 5

Met Ala Leu Leu Glu Arg Ile Leu Ala Arg Asp Asn Leu Ile Thr Ala
1               5                   10                  15

Leu Lys Arg Val Glu Ala Asn Gln Gly Ala Pro Gly Ile Asp Gly Val
                20                  25                  30

Ser Thr Asp Gln Leu Arg Asp Tyr Ile Arg Ala His Trp Ser Thr Ile
                35                  40                  45

His Ala Gln Leu Leu Ala Gly Thr Tyr Arg Pro Ala Pro Val Arg Arg
                50                  55                  60

Val Glu Ile Pro Lys Pro Gly Gly Gly Thr Arg Gln Leu Gly Ile Pro
65                  70                  75                  80

Thr Val Val Asp Arg Leu Ile Gln Gln Ala Ile Leu Gln Glu Leu Thr
                85                  90                  95
```

```
Pro Ile Phe Asp Pro Asp Phe Ser Ser Ser Phe Gly Phe Arg Pro
            100                 105                 110

Gly Arg Asn Ala His Asp Ala Val Arg Gln Ala Gln Gly Tyr Ile Gln
        115                 120                 125

Glu Gly Tyr Arg Tyr Val Val Asp Met Asp Leu Glu Lys Phe Phe Asp
        130                 135                 140

Arg Val Asn His Asp Ile Leu Met Ser Arg Val Ala Arg Lys Val Lys
145                 150                 155                 160

Asp Lys Arg Val Leu Lys Leu Ile Arg Ala Tyr Leu Gln Ala Gly Val
                165                 170                 175

Met Ile Glu Gly Val Lys Val Gln Thr Glu Glu Gly Thr Pro Gln Gly
            180                 185                 190

Gly Pro Leu Ser Pro Leu Leu Ala Asn Ile Leu Leu Asp Asp Leu Asp
        195                 200                 205

Lys Glu Leu Glu Lys Arg Gly Leu Lys Phe Cys Arg Tyr Ala Asp Asp
210                 215                 220

Cys Asn Ile Tyr Val Lys Ser Leu Arg Ala Gly Gln Arg Val Lys Gln
225                 230                 235                 240

Ser Ile Gln Arg Phe Leu Glu Lys Thr Leu Lys Leu Lys Val Asn Glu
                245                 250                 255

Glu Lys Ser Ala Val Asp Arg Pro Trp Lys Arg Ala Phe Leu Gly Phe
            260                 265                 270

Ser Phe Thr Pro Glu Arg Lys Ala Arg Ile Arg Leu Ala Pro Arg Ser
        275                 280                 285

Ile Gln Arg Leu Lys Gln Arg Ile Arg Gln Leu Thr Asn Pro Asn Trp
    290                 295                 300

Ser Ile Ser Met Pro Glu Arg Ile His Arg Val Asn Gln Tyr Val Met
305                 310                 315                 320

Gly Trp Ile Gly Tyr Phe Arg Leu Val Glu Thr Pro Ser Val Leu Gln
                325                 330                 335

Thr Ile Glu Gly Trp Ile Arg Arg Arg Leu Arg Leu Cys Gln Trp Leu
            340                 345                 350

Gln Trp Lys Arg Val Arg Thr Arg Ile Arg Glu Leu Arg Ala Leu Gly
        355                 360                 365

Leu Lys Glu Thr Ala Val Met Glu Ile Ala Asn Thr Arg Lys Gly Ala
370                 375                 380

Trp Arg Thr Thr Lys Thr Pro Gln Leu His Gln Ala Leu Gly Lys Thr
385                 390                 395                 400

Tyr Trp Thr Ala Gln Gly Leu Lys Ser Leu Thr Gln Arg Tyr Phe Glu
                405                 410                 415

Leu Arg Gln Gly
            420

<210> SEQ ID NO 6
<211> LENGTH: 934
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30
```

```
Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Ala Ala Leu Ala Ala Gln Thr Ala
            355                 360                 365

Ala Ala Ala Ala Met Glu Thr Arg Gln Met Thr Val Asp Gln Thr Thr
        370                 375                 380

Gly Ala Val Thr Asn Gln Thr Glu Thr Ser Trp His Ser Ile Asn Trp
385                 390                 395                 400

Thr Lys Ala Asn Arg Glu Val Lys Arg Leu Gln Val Arg Ile Ala Lys
                405                 410                 415

Ala Val Lys Glu Gly Arg Trp Gly Lys Val Lys Ala Leu Gln Trp Leu
                420                 425                 430

Leu Thr His Ser Phe Tyr Gly Lys Ala Leu Ala Val Lys Arg Val Thr
            435                 440                 445
```

-continued

```
Asp Asn Ser Gly Ser Arg Thr Pro Gly Val Asp Gly Ile Thr Trp Ser
450                 455                 460
Thr Gln Glu Gln Lys Thr Gln Ala Ile Lys Ser Leu Arg Arg Arg Gly
465                 470                 475                 480
Tyr Lys Pro Gln Pro Leu Arg Arg Val Tyr Ile Pro Lys Ala Asn Gly
                485                 490                 495
Lys Gln Arg Pro Leu Gly Ile Pro Thr Met Lys Asp Arg Ala Met Gln
            500                 505                 510
Ala Leu Tyr Ala Leu Ala Leu Glu Pro Val Ala Glu Thr Thr Ala Asp
            515                 520                 525
Arg Asn Ser Tyr Gly Phe Arg Arg Gly Arg Cys Thr Ala Asp Ala Ala
530                 535                 540
Gly Gln Cys Phe Leu Ala Leu Ala Lys Ala Lys Ser Ala Glu His Val
545                 550                 555                 560
Leu Asp Ala Asp Ile Ser Gly Cys Phe Asp Asn Ile Ser His Glu Trp
                565                 570                 575
Leu Leu Ala Asn Thr Pro Leu Asp Lys Gly Ile Leu Arg Lys Trp Leu
            580                 585                 590
Lys Ser Gly Phe Val Trp Lys Gln Gln Leu Phe Pro Thr His Ala Gly
            595                 600                 605
Thr Pro Gln Gly Gly Val Ile Ser Pro Val Leu Ala Asn Ile Thr Leu
610                 615                 620
Asp Gly Met Glu Glu Leu Leu Ala Lys His Leu Arg Gly Gln Lys Val
625                 630                 635                 640
Asn Leu Ile Arg Tyr Ala Asp Asp Phe Val Val Thr Gly Lys Asp Glu
                645                 650                 655
Glu Thr Leu Glu Lys Ala Arg Asn Leu Ile Gln Glu Phe Leu Lys Glu
            660                 665                 670
Arg Gly Leu Thr Leu Ser Pro Glu Lys Thr Lys Ile Val His Ile Glu
            675                 680                 685
Glu Gly Phe Asp Phe Leu Gly Trp Asn Ile Arg Lys Tyr Asn Gly Val
690                 695                 700
Leu Leu Ile Lys Pro Ala Lys Lys Asn Val Lys Ala Phe Leu Lys Lys
705                 710                 715                 720
Ile Arg Asp Thr Leu Arg Glu Leu Arg Thr Ala Thr Gln Glu Ile Val
                725                 730                 735
Ile Asp Thr Leu Asn Pro Ile Ile Arg Gly Trp Ala Asn Tyr His Lys
            740                 745                 750
Gly Gln Val Ser Lys Glu Thr Phe Asn Arg Val Asp Phe Ala Thr Trp
            755                 760                 765
His Lys Leu Trp Arg Trp Ala Arg Arg Arg His Pro Asn Lys Pro Ala
770                 775                 780
Gln Trp Val Lys Asp Lys Tyr Phe Ile Lys Asn Gly Ser Arg Asp Trp
785                 790                 795                 800
Val Phe Gly Met Val Met Lys Asp Lys Asn Gly Glu Leu Arg Thr Lys
                805                 810                 815
Arg Leu Ile Lys Thr Ser Asp Thr Arg Ile Gln Arg His Val Lys Ile
            820                 825                 830
Lys Ala Asp Ala Asn Pro Phe Leu Pro Glu Trp Ala Glu Tyr Phe Glu
            835                 840                 845
Lys Arg Lys Lys Leu Lys Ala Pro Ala Gln Tyr Arg Arg Ile Arg
850                 855                 860
Arg Glu Leu Trp Lys Lys Gln Gly Gly Ile Cys Pro Val Cys Gly Gly
```

```
                865                 870                 875                 880
Glu Ile Glu Gln Asp Met Leu Thr Asp Ile His His Ile Leu Pro Lys
                    885                 890                 895
His Lys Gly Gly Ser Asp Asp Leu Asp Asn Leu Val Leu Ile His Ala
                    900                 905                 910
Asn Cys His Lys Gln Val His Ser Arg Asp Gly Gln His Ser Arg Ser
                    915                 920                 925
Leu Leu Lys Glu Gly Leu
                    930

<210> SEQ ID NO 7
<211> LENGTH: 934
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Lys Ile Glu Glu Gly Lys Leu Val Ile Trp Ile Asn Gly Asp Lys
1               5                   10                  15
Gly Tyr Asn Gly Leu Ala Glu Val Gly Lys Lys Phe Glu Lys Asp Thr
                20                  25                  30
Gly Ile Lys Val Thr Val Glu His Pro Asp Lys Leu Glu Glu Lys Phe
            35                  40                  45
Pro Gln Val Ala Ala Thr Gly Asp Gly Pro Asp Ile Ile Phe Trp Ala
    50                  55                  60
His Asp Arg Phe Gly Gly Tyr Ala Gln Ser Gly Leu Leu Ala Glu Ile
65                  70                  75                  80
Thr Pro Asp Lys Ala Phe Gln Asp Lys Leu Tyr Pro Phe Thr Trp Asp
                85                  90                  95
Ala Val Arg Tyr Asn Gly Lys Leu Ile Ala Tyr Pro Ile Ala Val Glu
                100                 105                 110
Ala Leu Ser Leu Ile Tyr Asn Lys Asp Leu Leu Pro Asn Pro Pro Lys
            115                 120                 125
Thr Trp Glu Glu Ile Pro Ala Leu Asp Lys Glu Leu Lys Ala Lys Gly
    130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
                180                 185                 190
Leu Thr Phe Leu Val Asp Leu Ile Lys Asn Lys His Met Asn Ala Asp
            195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
            275                 280                 285
```

-continued

```
Glu Gly Leu Glu Ala Val Asn Lys Asp Lys Pro Leu Gly Ala Val Ala
    290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                    325                 330                 335
Met Ser Ala Phe Trp Tyr Ala Val Arg Thr Ala Val Ile Asn Ala Ala
                340                 345                 350
Ser Gly Arg Gln Thr Val Asp Ala Leu Ala Ala Gln Thr Ala
            355                 360                 365
Ala Ala Ala Met Glu Thr Arg Gln Met Ala Val Glu Gln Thr Thr
370                 375                 380
Gly Ala Val Thr Asn Gln Thr Glu Thr Ser Trp His Ser Ile Asp Trp
385                 390                 395                 400
Ala Lys Ala Asn Arg Glu Val Lys Arg Leu Gln Val Arg Ile Ala Lys
                    405                 410                 415
Ala Val Lys Glu Gly Arg Trp Gly Lys Val Lys Ala Leu Gln Trp Leu
                420                 425                 430
Leu Thr His Ser Phe Tyr Gly Lys Ala Leu Ala Val Lys Arg Val Thr
            435                 440                 445
Asp Asn Ser Gly Ser Lys Thr Pro Gly Val Asp Gly Ile Thr Trp Ser
450                 455                 460
Thr Gln Glu Gln Lys Ala Gln Ala Ile Lys Ser Leu Arg Arg Gly
465                 470                 475                 480
Tyr Lys Pro Gln Pro Leu Arg Arg Val Tyr Ile Pro Lys Ala Asn Gly
                    485                 490                 495
Lys Gln Arg Pro Leu Gly Ile Pro Thr Met Lys Asp Arg Ala Met Gln
                500                 505                 510
Ala Leu Tyr Ala Leu Ala Leu Glu Pro Val Ala Glu Thr Thr Ala Asp
            515                 520                 525
Arg Asn Ser Tyr Gly Phe Arg Arg Gly Arg Cys Ile Ala Asp Ala Ala
530                 535                 540
Thr Gln Cys His Ile Thr Leu Ala Lys Thr Asp Arg Ala Gln Tyr Val
545                 550                 555                 560
Leu Asp Ala Asp Ile Ala Gly Cys Phe Asp Asn Ile Ser His Glu Trp
                    565                 570                 575
Leu Leu Ala Asn Ile Pro Leu Asp Lys Arg Ile Leu Arg Lys Trp Leu
                580                 585                 590
Lys Ser Gly Phe Val Trp Lys Gln Gln Leu Phe Pro Ile His Ala Gly
            595                 600                 605
Thr Pro Gln Gly Gly Val Ile Ser Pro Met Leu Ala Asn Met Thr Leu
610                 615                 620
Asp Gly Met Glu Glu Leu Leu Asn Lys Phe Pro Arg Ala His Lys Val
625                 630                 635                 640
Lys Leu Ile Arg Tyr Ala Asp Asp Phe Val Thr Gly Glu Thr Lys
                    645                 650                 655
Glu Val Leu Tyr Ile Ala Gly Ala Val Ile Gln Ala Phe Leu Lys Glu
                660                 665                 670
Arg Gly Leu Thr Leu Ser Lys Glu Lys Thr Lys Ile Val His Ile Glu
            675                 680                 685
Glu Gly Phe Asp Phe Leu Gly Trp Asn Ile Arg Lys Tyr Asp Gly Lys
690                 695                 700
Leu Leu Ile Lys Pro Ala Lys Lys Asn Val Lys Ala Phe Leu Lys Lys
```

```
            705                 710                 715                 720
Ile Arg Asp Thr Leu Arg Glu Leu Arg Thr Ala Pro Gln Glu Ile Val
                725                 730                 735

Ile Asp Thr Leu Asn Pro Ile Ile Arg Gly Trp Thr Asn Tyr His Lys
                740                 745                 750

Asn Gln Ala Ser Lys Glu Thr Phe Val Gly Val Asp His Leu Ile Trp
                755                 760                 765

Gln Lys Leu Trp Arg Trp Ala Arg Arg His Pro Ser Lys Ser Val
    770                 775                 780

Arg Trp Val Lys Ser Lys Tyr Phe Ile Gln Ile Gly Asn Arg Lys Trp
785                 790                 795                 800

Met Phe Gly Ile Trp Thr Lys Asp Lys Asn Gly Asp Pro Trp Ala Lys
                805                 810                 815

His Leu Ile Lys Ala Ser Glu Ile Arg Ile Gln Arg Arg Gly Lys Ile
                820                 825                 830

Lys Ala Asp Ala Asn Pro Phe Leu Pro Glu Trp Ala Glu Tyr Phe Glu
                835                 840                 845

Gln Arg Lys Lys Leu Lys Glu Ala Pro Ala Gln Tyr Arg Arg Thr Arg
    850                 855                 860

Arg Glu Leu Trp Lys Lys Gln Gly Gly Ile Cys Pro Val Cys Gly Gly
865                 870                 875                 880

Glu Ile Glu Gln Asp Met Leu Thr Glu Ile His His Ile Leu Pro Lys
                885                 890                 895

His Lys Gly Gly Thr Asp Asp Leu Asp Asn Leu Val Leu Ile His Thr
                900                 905                 910

Asn Cys His Lys Gln Val His Asn Arg Asp Gly Gln His Ser Arg Phe
                915                 920                 925

Leu Leu Lys Glu Gly Leu
    930

<210> SEQ ID NO 8
<211> LENGTH: 934
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125
```

```
Thr Trp Glu Glu Ile Pro Ala Leu Asp Lys Glu Leu Lys Ala Lys Gly
    130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
    290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Ala Ala Leu Ala Ala Ala Gln Thr Ala
        355                 360                 365
Ala Ala Ala Ala Met Glu Thr Arg Gln Met Ala Val Glu Gln Thr Thr
    370                 375                 380
Gly Ala Val Thr Asn Gln Thr Glu Thr Ser Trp His Ser Ile Asp Trp
385                 390                 395                 400
Ala Lys Ala Asn Arg Glu Val Lys Arg Leu Gln Val Arg Ile Ala Lys
                405                 410                 415
Ala Val Lys Glu Gly Arg Trp Gly Lys Val Lys Ala Leu Gln Trp Leu
            420                 425                 430
Leu Thr His Ser Phe Tyr Gly Lys Ala Leu Ala Val Lys Arg Val Thr
        435                 440                 445
Asp Asn Ser Gly Ser Lys Thr Pro Gly Val Asp Gly Ile Thr Trp Ser
    450                 455                 460
Thr Gln Glu Gln Lys Ala Gln Ala Ile Lys Ser Leu Arg Arg Arg Gly
465                 470                 475                 480
Tyr Lys Pro Gln Pro Leu Arg Arg Val Tyr Ile Pro Lys Ala Ser Gly
                485                 490                 495
Lys Gln Arg Pro Leu Gly Ile Pro Thr Thr Lys Asp Arg Ala Met Gln
            500                 505                 510
Ala Leu Tyr Ala Leu Ala Leu Glu Pro Val Ala Glu Thr Thr Ala Asp
        515                 520                 525
Arg Asn Ser Tyr Gly Phe Arg Gln Gly Arg Cys Thr Ala Asp Ala Ala
    530                 535                 540
Gly Gln Cys Phe Thr Val Leu Gly Arg Ser Asp Cys Ala Lys Tyr Ile
```

```
            545                 550                 555                 560
Leu Asp Ala Asp Ile Thr Gly Cys Phe Asp Asn Ile Ser His Glu Trp
                565                 570                 575
Leu Leu Asp Asn Ile Pro Leu Asp Lys Glu Val Leu Arg Lys Trp Leu
            580                 585                 590
Lys Ser Gly Phe Val Trp Lys Gln Gln Leu Phe Pro Thr His Ala Gly
        595                 600                 605
Thr Pro Gln Gly Gly Val Ile Ser Pro Met Leu Ala Asn Met Thr Leu
    610                 615                 620
Asp Gly Met Glu Glu Leu Leu Lys Lys His Leu Arg Lys Gln Lys Val
625                 630                 635                 640
Asn Leu Ile Arg Tyr Ala Asp Asp Phe Val Val Thr Gly Glu Ser Lys
                645                 650                 655
Glu Thr Leu Glu Lys Val Thr Thr Val Ile Gln Glu Phe Leu Lys Glu
            660                 665                 670
Arg Gly Leu Thr Leu Ser Glu Glu Lys Thr Lys Val Val His Ile Glu
        675                 680                 685
Glu Gly Phe Asp Phe Leu Gly Trp Asn Ile Arg Lys Tyr Gly Glu Lys
    690                 695                 700
Leu Leu Ile Lys Pro Ala Lys Lys Asn Ile Lys Ala Phe His Lys Lys
705                 710                 715                 720
Ile Arg Asp Ala Leu Lys Glu Leu Arg Thr Ala Thr Gln Glu Ala Val
                725                 730                 735
Ile Asp Thr Leu Asn Pro Ile Ile Lys Gly Trp Ala Asn Tyr His Arg
            740                 745                 750
Asn Gln Val Ser Lys Arg Ile Phe Asn Arg Ala Asp Asp Asn Ile Trp
        755                 760                 765
His Lys Leu Trp Arg Trp Ala Lys Arg Arg His Pro Asn Lys Pro Ala
    770                 775                 780
Arg Trp Thr Lys Asn Lys Tyr Phe Ile Lys Ile Gly Asn Arg His Trp
785                 790                 795                 800
Val Phe Gly Thr Trp Lys Lys Asp Lys Glu Gly Arg Leu Arg Ser Arg
                805                 810                 815
Tyr Leu Ile Lys Ala Gly Asp Thr Arg Ile Gln Arg His Val Lys Ile
            820                 825                 830
Lys Ala Asp Ala Asn Pro Phe Leu Pro Glu Trp Ala Glu Tyr Phe Glu
        835                 840                 845
Glu Arg Lys Lys Leu Lys Glu Ala Pro Ala Gln Tyr Arg Arg Ile Arg
    850                 855                 860
Arg Glu Leu Trp Lys Lys Gln Gly Gly Ile Cys Pro Val Cys Gly Gly
865                 870                 875                 880
Glu Ile Glu Gln Asp Met Leu Thr Glu Ile His His Ile Leu Pro Lys
                885                 890                 895
His Lys Gly Gly Ser Asp Asp Leu Asp Asn Leu Val Leu Ile His Ala
            900                 905                 910
Asn Cys His Lys Gln Val His Ser Arg Asp Gly Gln His Ser Arg Phe
        915                 920                 925
Leu Leu Lys Glu Gly Leu
    930

<210> SEQ ID NO 9
<211> LENGTH: 1007
<212> TYPE: PRT
<213> ORGANISM: Artificial Sequence
```

<220> FEATURE:
<223> OTHER INFORMATION: Description of Artificial Sequence: Synthetic
     polypeptide

<400> SEQUENCE: 9

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Ala Ala Leu Ala Ala Ala Gln Thr Ala
        355                 360                 365

Ala Ala Ala Ala Met Lys Val Asn Lys Leu Val Val Lys Ser Glu Gln
    370                 375                 380

Asp Leu Arg Asn Cys Leu Asp Leu Leu Tyr Gln Glu Ala Lys Lys Gly
```

```
                385                 390                 395                 400
Lys His Phe Tyr Gly Met Leu Glu Leu Leu Gln Asn Asp Val Val Ile
                    405                 410                 415

Leu Glu Ala Ile Arg Asn Ile Lys Ser Asn Lys Gly Ser Lys Thr Ala
                    420                 425                 430

Gly Ile Asp Gln Lys Ile Val Asp Asp Tyr Leu Leu Met Pro Thr Glu
                    435                 440                 445

Lys Val Phe Gly Met Ile Lys Ala Lys Leu Asn Asp Tyr Lys Pro Ile
                    450                 455                 460

Pro Val Arg Arg Cys Asn Lys Pro Lys Gly Asn Ala Lys Ser Ser Lys
465                 470                 475                 480

Arg Lys Gly Asn Ser Pro Asn Glu Glu Gly Glu Thr Arg Pro Leu Gly
                    485                 490                 495

Ile Ser Ala Val Thr Asp Arg Ile Ile Gln Glu Met Leu Arg Ile Val
                    500                 505                 510

Leu Glu Pro Ile Phe Glu Ala Gln Phe Tyr Pro His Ser Tyr Gly Phe
                    515                 520                 525

Arg Pro Tyr Arg Ser Thr Glu His Ala Leu Ala Trp Met Leu Lys Ile
                    530                 535                 540

Ile Asn Gly Ser Lys Leu Tyr Trp Val Val Lys Gly Asp Ile Glu Ser
545                 550                 555                 560

Tyr Phe Asp His Ile Asn His Lys Lys Leu Leu Asn Ile Met Trp Asn
                    565                 570                 575

Met Gly Val Arg Asp Lys Arg Val Leu Cys Ile Val Lys Lys Met Leu
                    580                 585                 590

Lys Ala Gly Gln Val Ile Gln Gly Lys Phe Tyr Pro Thr Ala Lys Gly
                    595                 600                 605

Ile Pro Gln Gly Gly Ile Ile Ser Pro Leu Leu Ala Asn Val Tyr Leu
                    610                 615                 620

Asn Ser Phe Asp Trp Met Val Gly Gln Glu Tyr Glu Tyr His Pro Asn
625                 630                 635                 640

Asn Ala Asn Tyr Arg Glu Lys Lys Asn Ala Leu Ala Ala Leu Arg Asn
                    645                 650                 655

Lys Gly His His Pro Val Phe Tyr Ile Arg Tyr Ala Asp Asp Trp Val
                    660                 665                 670

Ile Leu Thr Asp Thr Lys Glu Tyr Ala Glu Lys Ile Arg Glu Gln Cys
                    675                 680                 685

Lys Gln Tyr Leu Ala Cys Glu Leu His Leu Thr Leu Ser Asp Glu Lys
                    690                 695                 700

Thr Phe Ile Ala Asp Ile Arg Glu Gln Arg Val Lys Phe Leu Gly Phe
705                 710                 715                 720

Cys Ile Glu Ala Gly Lys Arg Arg Phe His Lys Gly Phe Ala Ala
                    725                 730                 735

Arg Met Ile Pro Asp Met Glu Lys Val Asn Ala Lys Val Lys Glu Ile
                    740                 745                 750

Lys Arg Asp Ile Arg Leu Leu Arg Thr Arg Lys Ser Glu Leu Glu Lys
                    755                 760                 765

Ala Leu Asp Ile Glu Asn Ile Asn Thr Lys Ile Gly Leu Ala Asn
                    770                 775                 780

His Leu Lys Ile Gly Ile Ser Lys Tyr Ile Met Gly Lys Val Asp Arg
785                 790                 795                 800

Val Ile Glu Glu Thr Ala Tyr Arg Thr Trp Val Lys Met Tyr Gly Lys
                    805                 810                 815
```

```
Glu Lys Ala Ala Gln Tyr Lys Arg Pro Val Ser Glu Phe His Asn Arg
            820                 825                 830

Ile Asp Arg His Lys Gly Tyr Gln Met Lys His Phe Ser Val Val Thr
            835                 840                 845

Glu Asp Gly Ile Arg Val Gly Ile Thr His Ala Lys Ile Thr Pro Ile
850                 855                 860

Gln Tyr Ala Thr Val Phe Lys Gln Glu Met Thr Pro Tyr Thr Ala Asp
865                 870                 875                 880

Gly Arg Lys Met Tyr Glu Lys His Arg Lys Ile Arg Leu Pro Asp
            885                 890                 895

Lys Met Ser Leu Phe Asp His Asp Ser Ile Phe Ile Tyr Ile Leu Ser
            900                 905                 910

Glu His Asn Asp Gly Lys Tyr Asn Leu Glu Tyr Phe Leu Asn Arg Val
            915                 920                 925

Asn Val Phe His Arg Asp Lys Gly Lys Cys Lys Ile Cys Ala Val Tyr
            930                 935                 940

Leu Ser Pro Gly Asn Phe His Cys His His Ile Asp Pro Ser Lys Pro
945                 950                 955                 960

Leu Ser Glu Ile Asn Lys Thr Val Asn Leu Ile Ser Leu Cys Asn Gln
            965                 970                 975

Cys His Arg Leu Val His Ser Asn Gln Glu Pro Pro Phe Thr Glu Arg
            980                 985                 990

Lys Met Phe Asp Lys Leu Thr Lys Tyr Arg Asn Lys Leu Lys Ile
            995                 1000                1005

<210> SEQ ID NO 10
<211> LENGTH: 792
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
```

```
                    165                 170                 175
Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Ala Ala Leu Ala Ala Ala Gln Thr Ala
        355                 360                 365

Ala Ala Ala Ala Met Ala Leu Leu Glu Arg Ile Leu Ala Arg Asp Asn
    370                 375                 380

Leu Ile Thr Ala Leu Lys Arg Val Glu Ala Asn Gln Gly Ala Pro Gly
385                 390                 395                 400

Ile Asp Gly Val Ser Thr Asp Gln Leu Arg Asp Tyr Ile Arg Ala His
                405                 410                 415

Trp Ser Thr Ile His Ala Gln Leu Leu Ala Gly Thr Tyr Arg Pro Ala
            420                 425                 430

Pro Val Arg Arg Val Glu Ile Pro Lys Pro Gly Gly Gly Thr Arg Gln
        435                 440                 445

Leu Gly Ile Pro Thr Val Asp Arg Leu Ile Gln Gln Ala Ile Leu
    450                 455                 460

Gln Glu Leu Thr Pro Ile Phe Asp Pro Asp Phe Ser Ser Ser Phe
465                 470                 475                 480

Gly Phe Arg Pro Gly Arg Asn Ala His Asp Ala Val Arg Gln Ala Gln
                485                 490                 495

Gly Tyr Ile Gln Glu Gly Tyr Arg Tyr Val Val Asp Met Asp Leu Glu
            500                 505                 510

Lys Phe Phe Asp Arg Val Asn His Asp Ile Leu Met Ser Arg Val Ala
        515                 520                 525

Arg Lys Val Lys Asp Lys Arg Val Leu Lys Leu Ile Arg Ala Tyr Leu
    530                 535                 540

Gln Ala Gly Val Met Ile Glu Gly Val Lys Val Gln Thr Glu Glu Gly
545                 550                 555                 560

Thr Pro Gln Gly Gly Pro Leu Ser Pro Leu Leu Ala Asn Ile Leu Leu
                565                 570                 575

Asp Asp Leu Asp Lys Glu Leu Glu Lys Arg Gly Leu Lys Phe Cys Arg
            580                 585                 590
```

```
Tyr Ala Asp Asp Cys Asn Ile Tyr Val Lys Ser Leu Arg Ala Gly Gln
            595                 600                 605

Arg Val Lys Gln Ser Ile Gln Arg Phe Leu Glu Lys Thr Leu Lys Leu
        610                 615                 620

Lys Val Asn Glu Glu Lys Ser Ala Val Asp Arg Pro Trp Lys Arg Ala
625                 630                 635                 640

Phe Leu Gly Phe Ser Phe Thr Pro Glu Arg Lys Ala Arg Ile Arg Leu
                645                 650                 655

Ala Pro Arg Ser Ile Gln Arg Leu Lys Gln Arg Ile Arg Gln Leu Thr
            660                 665                 670

Asn Pro Asn Trp Ser Ile Ser Met Pro Glu Arg Ile His Arg Val Asn
        675                 680                 685

Gln Tyr Val Met Gly Trp Ile Gly Tyr Phe Arg Leu Val Glu Thr Pro
    690                 695                 700

Ser Val Leu Gln Thr Ile Glu Gly Trp Ile Arg Arg Arg Leu Arg Leu
705                 710                 715                 720

Cys Gln Trp Leu Gln Trp Lys Arg Val Arg Thr Arg Ile Arg Glu Leu
                725                 730                 735

Arg Ala Leu Gly Leu Lys Glu Thr Ala Val Met Glu Ile Ala Asn Thr
            740                 745                 750

Arg Lys Gly Ala Trp Arg Thr Thr Lys Thr Pro Gln Leu His Gln Ala
        755                 760                 765

Leu Gly Lys Thr Tyr Trp Thr Ala Gln Gly Leu Lys Ser Leu Thr Gln
    770                 775                 780

Arg Tyr Phe Glu Leu Arg Gln Gly
785                 790

<210> SEQ ID NO 11
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65              70                  75                  80

Thr Pro Asp Lys Ala Phe Gln Asp Lys Leu Tyr Pro Phe Thr Trp Asp
            85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
```

```
            145                 150                 155                 160
Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Ala Ala Leu Ala Ala Ala Gln Thr
            355                 360                 365

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Ala Ala Ala
1               5

<210> SEQ ID NO 13
<211> LENGTH: 8260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg    360
tggtggtgtc gatggtagaa cgaagcggcg tcgaagcctg taaagcggcg gtgcacaatc    420
```

```
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggatttc    960 gcctgctggg gcaaaccagc gtggaccgct tgctgcaact ctctcagggc caggcggtga   1020
agggcaatca gctgttgccc gtctcactgg tgaaaagaaa aaccaccctg cgcccaata    1080 cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgttttt gcgccgacat cataacggtt   1380
ctggcaaata ttctgaaatg agctgttgac aattaatcat cggctcgtat aatgtgtgga   1440
attgtgagcg gataacaatt tcacacagga acagccagt ccgtttaggt gttttcacga    1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt ggtggctac   1740 gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga acccgccaaa aacctgggaa   1920
gagatcccgg cgctggataa agaactgaaa gcgaaaggta agagcgcgct gatgttcaac   1980
ctgcaagaac cgtacttcac ctggccgctg attgctgctg acggggtta tgcgttcaag   2040 tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccact atggaaaacg cccagaaagg tgaaatcatg   2520
ccgaacatcc gcagatgtc cgctttctgg tatgccgtgc gtactgcggt gatcaacgcc   2580
gccagcggtc gtcagactgt cgatgccgcc ctggccgccg cgcagactgc gccgccgcc   2640 gccatggaga caaggcaaat gacggtggac caaaccactg gtgcggtcac caaccaaacg   2700
gaaacaagct ggcacagcat aaactggacc aaagccaacc gtgaggtaaa gaggctgcaa   2760
```

```
gtgcgtatcg caaaggctgt gaaggaagga cgctggggca aagtgaaagc tttgcaatgg   2820
ctcctgaccc actcgttcta cggcaaagcc ctcgccgtga acgggtaac tgacaactca    2880 ggcagtagaa cacctggtgt ggacgggata acctggtcca cacaagagca gaaaacccaa   2940
gccataaagt ccctcaggag aagaggctat aaaccccaac ccctgaggcg ggtatacatc   3000
ccgaaagcaa acggcaaaca gcgcccgcta ggaatcccga caatgaagga cagggcaatg   3060
caggcactat atgccctagc cctagaacca gtcgcgaaaa ccacagcgga ccggaactcc   3120
tatgggttcc gccgagggcg atgtacggca gatgcggcag acaatgcttc ccttgctctg   3180
gcaaaagcca agtcggctga acacgtcctt gacgctgaca tatccggatg ctttgataac   3240
atcagccatg agtggctact agccaacact ccactggaca aagggatctt acggaaatgg   3300
cttaaatctg ggttcgtctg gaaacagcaa ctcttcccca cccatgctgg gacacctcag   3360
ggaggggtaa tctccccagt tcttgccaat ataaccctag atgggatgga agaactgttg   3420
gccaaacacc tcagaggtca aaagtcaac ctcatccgat atgctgacga ttttgtcgtg   3480
acgggaaaag atgaggaaac cctggagaaa gccagaaacc taatccagga gttcctaaaa   3540
gaacggggct tgaccctgtc ccccgagaag acaaaaatcg tccatattga ggaaggcttc   3600
gactttctcg gatggaacat tcgcaagtac aacgggttc ttctcatcaa acccgcgaag   3660
aagaacgtga aagcgttcct caagaaaatc cgagacactc taagggaact taggacagca   3720
acccaggaaa tcgtgataga cacactcaac ccaatcatta gaggttgggc caactatcac   3780
aaaggacaag tctctaagga aaccttcaac cgagtggact cgccacctg gcacaaattg   3840 tggcgatggg caaggcgccg gcacccaaac aaacctgccc aatgggtgaa ggacaaatac   3900
ttcatcaaaa acggaagcag agactgggtg ttcggtatgg tgatgaaaga caagaacggg   3960
gaactgagga ccaaacgcct aatcaaaacc tctgacaccc gaatccaacg ccacgtcaaa   4020
atcaaggcag acgccaatcc gtttctccca gagtgggcag aatactttga gaaacgcaag   4080
aaactcaaaa aagcccctgc tcaatatcgg cgcatccgcc gagaactatg gaagaaacag   4140
ggtggtatct gtccagtatg cggggtgaa attgagcaag acatgctcac tgacatccac   4200
cacatattgc ccaaacacaa gggtggttct gacgacctgg ataatcttgt cttaatccac   4260
gccaactgcc acaaacaggt gcacagccga gatggtcagc acagccggtc cctcttgaaa   4320
gaggggcttt gactgcaggc aagcttggca ctggccgtcg ttttacaacg tcgtgactgg   4380
gaaaaccctg gcgttaccca acttaatcgc cttgcagcac atccccctt cgccagctgg   4440 cgtaatagcg aagaggcccg caccgatcgc ccttcccaac agttgcgcag cctgaatggc   4500
gaatggcagc ttggctgttt tggcggatga gataagattt tcagcctgat acagattaaa   4560
tcagaacgca gaagcggtct gataaaacag aatttgcctg gcggcagtag cgcggtggtc   4620
ccacctgacc ccatgccgaa ctcagaagtg aaacgccgta gcgccgatgg tagtgtgggg   4680
tctccccatg cgagagtagg gaactgccag gcatcaaata aaacgaaagg ctcagtcgaa   4740
agactgggcc tttcgtttta tctgttgttt gtcggtgaac gctctcctga gtaggacaaa   4800
tccgccggga gcggatttga acgttgcgaa gcaacggccc ggagggtggc gggcaggacg   4860
cccgccataa actgccaggc atcaaattaa gcagaaggcc atcctgacgg atggcctttt   4920
tgcgtttcta caaactcttt tgtttatttt tctaaatac attcaaatat gtatccgctc   4980
atgagacaat aaccctgata aatgcttcaa taatattgaa aaaggaagag tatgagtatt   5040
caacatttcc gtgtcgccct tattccctt tttgcggcat tttgccttcc tgttttgct    5100 cacccagaaa cgctggtgaa agtaaaagat gctgaagatc agttgggtgc acgagtgggt   5160
```

```
tacatcgaac tggatctcaa cagcggtaag atccttgaga gttttcgccc cgaagaacgt   5220
tctccaatga tgagcacttt taaagttctg ctatgtggcg cggtattatc ccgtgttgac   5280
gccgggcaag agcaactcgg tcgccgcata cactattctc agaatgactt ggttgagtac   5340
tcaccagtca cagaaaagca tcttacggat ggcatgacag taagagaatt atgcagtgct   5400
gccataacca tgagtgataa cactgcggcc aacttacttc tgacaacgat cggaggaccg   5460
aaggagctaa ccgcttttt gcacaacatg ggggatcatg taactcgcct tgatcgttgg   5520
gaaccggagc tgaatgaagc cataccaaac gacgagcgtg acaccacgat gcctgtagca   5580
atggcaacaa cgttgcgcaa actattaact ggcgaactac ttactctagc ttcccggcaa   5640
caattaatag actggatgga ggcggataaa gttgcaggac cacttctgcg ctcggccctt   5700
ccggctggct ggtttattgc tgataaatct ggagccggtg agcgtgggtc tcgcggtatc   5760
attgcagcac tggggccaga tggtaagccc tcccgtatcg tagttatcta cacgacgggg   5820
agtcaggcaa ctatggatga acgaaataga cagatcgctg agataggtgc ctcactgatt   5880
aagcattggt aactgtcaga ccaagtttac tcatatatac tttagattga tttaccccgg   5940
ttgataatca gaaaagcccc aaaaacagga agattgtata agcaaatatt taaattgtaa   6000
acgttaatat tttgttaaaa ttcgcgttaa attttgtta aatcagctca ttttttaacc   6060
aataggccga atcggcaaa atcccttata aatcaaaaga atagaccgag atagggttga   6120
gtgttgttcc agtttggaac aagagtccac tattaaagaa cgtggactcc aacgtcaaag   6180
ggcgaaaaac cgtctatcag ggcgatggcc cactacgtga accatcaccc aaatcaagtt   6240
ttttggggtc gaggtgccgt aaagcactaa atcggaaccc taaagggagc ccccgattta   6300
gagcttgacg gggaaagccg cgaacgtgg cgagaaagga agggaagaaa gcgaaaggag   6360
cgggcgctag ggcgctggca agtgtagcgg tcacgctgcg cgtaaccacc acccgccg    6420 cgcttaatgc gccgctacag ggcgcgtaaa aggatctagg tgaagatcct tttgataat    6480 ctcatgacca aaatccctta acgtgagttt tcgttccact gagcgtcaga ccccgtagaa   6540
aagatcaaag gatcttcttg agatcctttt tttctgcgcg taatctgctg cttgcaaaca   6600
aaaaaaccac cgctaccagc ggtggtttgt ttgccggatc aagagctacc aactcttttt   6660
ccgaaggtaa ctggcttcag cagagcgcag ataccaaata ctgtccttct agtgtagccg   6720
tagttaggcc accacttcaa gaactctgta gcaccgccta catacctcgc tctgctaatc   6780
ctgttaccag tggctgctgc cagtggcgat aagtcgtgtc ttaccgggtt ggactcaaga   6840
cgatagttac cggataaggc gcagcggtcg ggctgaacgg ggggttcgtg cacacagccc   6900
agcttggagc gaacgaccta caccgaactg agatacctac agcgtgagct atgagaaagc   6960
gccacgcttc ccgaagggag aaaggcggac aggtatccgg taagcggcag gtcggaaca    7020 ggagagcgca cgagggagct tccaggggga aacgcctggt atctttatag tcctgtcggg   7080
tttcgccacc tctgacttga gcgtcgattt tgtgatgct cgtcaggggg gcggagccta    7140
tggaaaaacg ccagcaacgc ggccttttta cggttcctgg ccttttgctg gccttttgct   7200
cacatgttct ttcctgcgtt atcccctgat tctgtggata accgtattac cgcctttgag   7260
tgagctgata ccgctcgccg cagccgaacg accgagcgca gcgagtcagt gagcgaggaa   7320
gcggaagagc gcctgatgcg gtattttctc cttacgcatc tgtgcggtat ttcacaccgc   7380
atatatggtg cactctcagt acaatctgct ctgatgccgc atagttaagc cagtatacac   7440
tccgctatcg ctacgtgact gggtcatggc tgcgccccga cacccgccaa cacccgctga   7500
```

| | |
|---|---|
| cgcgccctga cgggcttgtc tgctcccggc atccgcttac agacaagctg tgaccgtctc | 7560 |
| cgggagctgc atgtgtcaga ggttttcacc gtcatcaccg aaacgcgcga ggcagctgcg | 7620 |
| gtaaagctca tcagcgtggt cgtgcagcga ttcacagatg tctgcctgtt catccgcgtc | 7680 |
| cagctcgttg agtttctcca gaagcgttaa tgtctggctt ctgataaagc gggccatgtt | 7740 |
| aagggcggtt ttttcctgtt tggtcactga tgcctccgtg taagggggat ttctgttcat | 7800 |
| gggggtaatg ataccgatga aacgagagag gatgctcacg atacgggtta ctgatgatga | 7860 |
| acatgcccgg ttactggaac gttgtgaggg taaacaactg gcggtatgga tgcggcggga | 7920 |
| ccagagaaaa atcactcagg gtcaatgcca gcgcttcgtt aatacagatg taggtgttcc | 7980 |
| acagggtagc cagcagcatc ctgcgatgca gatccggaac ataatggtgc agggcgctga | 8040 |
| cttccgcgtt tccagacttt acgaaacacg gaaaccgaag accattcatg ttgttgctca | 8100 |
| ggtcgcagac gttttgcagc agcagtcgct tcacgttcgc tcgcgtatcg gtgattcatt | 8160 |
| ctgctaacca gtaaggcaac cccgccagcc tagccgggtc ctcaacgaca ggagcacgat | 8220 |
| catgcgcacc cgtggccagg acccaacgct gcccgaaatt | 8260 |

<210> SEQ ID NO 14
<211> LENGTH: 8260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | |
|---|---|
| ccgacaccat cgaatggtgc aaaacctttc gcggtatggc atgatagcgc ccggaagaga | 60 |
| gtcaattcag ggtggtgaat gtgaaaccag taacgttata cgatgtcgca gagtatgccg | 120 |
| gtgtctctta tcagaccgtt tcccgcgtgg tgaaccaggc cagccacgtt tctgcgaaaa | 180 |
| cgcgggaaaa agtggaagcg gcgatggcgg agctgaatta cattcccaac cgcgtggcac | 240 |
| aacaactggc gggcaaacag tcgttgctga ttggcgttgc cacctccagt ctggccctgc | 300 |
| acgcgccgtc gcaaattgtc gcggcgatta atctcgcgc cgatcaactg ggtgccagcg | 360 |
| tggtggtgtc gatggtagaa cgaagcggcg tcgaagcctg taaagcggcg gtgcacaatc | 420 |
| ttctcgcgca acgcgtcagt gggctgatca ttaactatcc gctggatgac caggatgcca | 480 |
| ttgctgtgga agctgcctgc actaatgttc cggcgttatt tcttgatgtc tctgaccaga | 540 |
| cacccatcaa cagtattatt ttctcccatg aagacggtac gcgactgggc gtggagcatc | 600 |
| tggtcgcatt gggtcaccag caaatcgcgc tgttagcggg cccattaagt tctgtctcgg | 660 |
| cgcgtctgcg tctggctggc tggcataaat atctcactcg caatcaaatt cagccgatag | 720 |
| cggaacggga aggcgactgg agtgccatgt ccggttttca acaaaccatg caaatgctga | 780 |
| atgagggcat cgttcccact gcgatgctgg ttgccaacga tcagatggcg ctgggcgcaa | 840 |
| tgcgcgccat taccgagtcc gggctgcgcg ttggtgcgga tatctcggta gtgggatacg | 900 |
| acgataccga agacagctca tgttatatcc cgccgttaac caccatcaaa caggattttc | 960 |
| gcctgctggg gcaaaccagc gtggaccgct tgctgcaact ctctcagggc caggcggtga | 1020 |
| agggcaatca gctgttgccc gtctcactgg tgaaaagaaa accaccctg cgcccaata | 1080 |
| cgcaaaccgc ctctccccgc gcgttggccg attcattaat gcagctggca cgacaggttt | 1140 |
| cccgactgga aagcgggcag tgagcgcaac gcaattaatg taagttagct cactcattag | 1200 |
| gcacaattct catgtttgac agcttatcat cgactgcacg gtgcaccaat gcttctggcg | 1260 |

-continued

```
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt  ccgtttaggt gttttcacga    1500
gcacttcacc aacaaggacc atagcatatg aaaatcgaag aaggtaaact ggtaatctgg    1560
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt tggtggctac    1740
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta taacaaagat ctgctgccga acccgccaaa aacctgggaa    1920
gagatcccgg cgctggataa agaactgaaa gcgaaaggta agagcgcgct gatgttcaac    1980
ctgcaagaac cgtacttcac ctggccgctg attgctgctg acgggggtta tgcgttcaag    2040
tatgaaaacg gcaagtacga cattaaagac gtgggcgtgg ataacgctgg cgcgaaagcg    2100
ggtctgacct tcctggttga cctgattaaa acaaacaca  tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gccgtagcgc tgaagtctta cgaggaagag    2460
ttggcgaaag atccacgtat tgccgccact atggaaaacg cccagaaagg tgaaatcatg    2520
ccgaacatcc cgcagatgtc cgctttctgg tatgccgtgc gtactgcggt gatcaacgcc    2580
gccagcggtc gtcagactgt cgatgccgcc ctggccgccg cgcagactgc cgccgccgcc    2640
gccatggaga caaggcaaat ggcagtggaa caaaccactg gtgcggtcac caaccaaacg    2700
gaaacaagct ggcacagcat agactgggcc aaagccaacc gtgaggtaaa gaggctgcaa    2760
gtgcgtatcg caaaggctgt gaaggaagga cgctggggca aagtgaaagc tttgcaatgg    2820
ctcctgaccc actcgttcta cggcaaagcc ctcgccgtga acgggtaac  tgacaactcg    2880 ggcagcaaaa cacctggtgt ggacgggata acctggtcca cacaagagca gaaagcccaa    2940
gccataaagt ccctcaggag aagaggctat aaacccaaac ccctgaggcg ggtatacatc    3000
ccgaaagcaa acggcaaaca gcgcccgcta ggaatcccga caatgaagga cagggcaatg    3060
caggcactat atgccctagc cctagaacca gtcgcgaaaa ccacagcaga ccggaactcc    3120
tatgggttcc ggcgaggacg atgcatagcc gatgcagcga cgcagtgtca catcacgcta    3180
gccaaaacag accgtgcaca atacgttctc gacgccgata ttgctgggtg ctttgacaac    3240
atcagccatg agtggctact agctaacatt ccactagaca aaagaattct acggaaatgg    3300
cttaaatctg ggtttgtctg gaagcagcaa ctcttcccca tccatgctgg aacacctcag    3360
ggaggggtaa tctccccgat gcttgccaac atgacactgg atgggatgga agaattgtta    3420
aacaagtttc ccagggcgca caaggtcaaa ctcatccgat atgccgacga cttcgtcgta    3480
accggtgaaa cgaaggaagt gctctatatt gccggtgcgg taatacaagc attcctcaag    3540 gaaagggggcc ttaccctatc aaaggaaaag acgaagatcg tacacattga agaagggttt    3600
gactttctcg gatggaacat tcgcaaatat gatgggaaac tgctcatcaa acctgcgaag    3660
```

```
aagaacgtta aagcgttcct caagaaaatc cgagacacct taagagaact taggacagca  3720
ccccaggaga ttgtgataga cacactcaac ccaatcatca gaggttggac taactatcac  3780
aaaaatcagg catccaaaga aaccttcgtc ggagtggacc acctcatatg gcaaaaatta  3840
tggcgatggg caaggcgccg cacccaagc aaatctgtcc gatgggtgaa gagtaagtac  3900
ttcatccaaa tcgggaacag aaaatggatg ttcggaatat ggacgaaaga caaaaacgga  3960
gacccgtggg ccaagcattt aatcaaagcc tcggaaatcc gaatccaacg tcgcggtaaa  4020
atcaaggcag acgccaaccc gtttctccca gaatgggcag aatactttga gcagcgcaag  4080
aaactcaaag aggcccctgc ccaataccgg cgcacccgtc gggaattgtg aagaaacaa  4140 ggcggcatct gtccagtatg tgggggagaa attgagcaag acatgctcac cgaaatccac  4200
cacatactgc ccaaacacaa gggtggtact gacgacctgg acaatcttgt cctaatccac  4260
actaactgcc acaaacaggt gcacaaccga gatggtcagc cagccggtt cctcttgaaa  4320 gaggggcttt gactgcaggc aagcttggca ctggccgtcg ttttacaacg tcgtgactgg  4380
gaaaaccctg gcgttaccca acttaatcgc cttgcagcac atccccttt cgccagctgg  4440 cgtaatagcg aagaggcccg caccgatcgc ccttcccaac agttgcgcag cctgaatggc  4500
gaatggcagc ttggctgttt tggcggatga gataagattt tcagcctgat acagattaaa  4560
tcagaacgca gaagcggtct gataaaacag aatttgcctg gcggcagtag cgcggtggtc  4620
ccacctgacc ccatgccgaa ctcagaagtg aaacgccgta gcgccgatgg tagtgtgggg  4680 tctcccatg cgagagtagg gaactgccag gcatcaaata aaacgaaagg ctcagtcgaa  4740
agactgggcc tttcgtttta tctgttgttt gtcggtgaac gctctcctga gtaggacaaa  4800
tccgccggga gcggatttga acgttgcgaa gcaacggccc ggagggtggc gggcaggacg  4860
cccgccataa actgccaggc atcaaattaa gcagaaggcc atcctgacgg atggcctttt  4920 tgcgttcta caaactcttt ttgtttattt ttctaaatac attcaaatat gtatccgctc  4980
atgagacaat aaccctgata aatgcttcaa taatattgaa aaaggaagag tatgagtatt  5040
caacatttcc gtgtcgccct tattccctt tttgcggcat tttgccttcc tgttttgct  5100 cacccagaaa cgctggtgaa agtaaaagat gctgaagatc agttgggtgc acgagtgggt  5160
tacatcgaac tggatctcaa cagcggtaag atccttgaga gttttcgccc cgaagaacgt  5220
tctccaatga tgagcacttt taaagttctg ctatgtggcg cggtattatc ccgtgttgac  5280
gccgggcaag agcaactcgg tcgccgcata cactattctc agaatgactt ggttgagtac  5340
tcaccagtca cagaaaagca tcttacggat ggcatgacag taagagaatt atgcagtgct  5400
gccataacca tgagtgataa cactgcggcc aacttacttc tgacaacgat cggaggaccg  5460
aaggagctaa ccgcttttt gcacaacatg ggggatcatg taactcgcct tgatcgttgg  5520
gaaccggagc tgaatgaagc cataccaaac gacgagcgtg acaccacgat gcctgtagca  5580
atggcaacaa cgttgcgcaa actattaact ggcgaactac ttactctagc ttcccggcaa  5640
caattaatag actggatgga ggcggataaa gttgcaggac cacttctgcg ctcggccctt  5700
ccggctggct ggtttattgc tgataaatct ggagccggtg agcgtgggtc tcgcggtatc  5760
attgcagcac tggggccaga tggtaagccc tcccgtatcg tagttatcta cacgacgggg  5820
agtcaggcaa ctatggatga acgaaataga cagatcgctg agataggtgc ctcactgatt  5880
aagcattggt aactgtcaga ccaagtttac tcatatatac tttagattga tttacccccgg  5940 ttgataatca gaaaagcccc aaaaacagga agattgtata agcaaatatt taaattgtaa  6000
```

```
acgttaatat tttgttaaaa ttcgcgttaa attttgtta aatcagctca ttttttaacc    6060
aataggccga aatcggcaaa atcccttata aatcaaaaga atagaccgag atagggttga    6120
gtgttgttcc agtttggaac aagagtccac tattaaagaa cgtggactcc aacgtcaaag    6180
ggcgaaaaac cgtctatcag ggcgatggcc cactacgtga accatcaccc aaatcaagtt    6240
ttttggggtc gaggtgccgt aaagcactaa atcggaaccc taagggagc ccccgattta     6300
gagcttgacg gggaaagccg gcgaacgtgg cgagaaagga agggaagaaa gcgaaaggag    6360
cgggcgctag ggcgctggca agtgtagcgg tcacgctgcg cgtaaccacc acacccgccg    6420
cgcttaatgc gccgctacag ggcgcgtaaa aggatctagg tgaagatcct ttttgataat    6480
ctcatgacca aaatccctta acgtgagttt tcgttccact gagcgtcaga ccccgtagaa    6540
aagatcaaag gatcttcttg agatcctttt tttctgcgcg taatctgctg cttgcaaaca    6600
aaaaaaccac cgctaccagc ggtggtttgt ttgccggatc aagagctacc aactctttt    6660
ccgaaggtaa ctggcttcag cagagcgcag ataccaaata ctgtccttct agtgtagccg    6720
tagttaggcc accacttcaa gaactctgta gcaccgccta catacctcgc tctgctaatc    6780
ctgttaccag tggctgctgc cagtggcgat aagtcgtgtc ttaccgggtt ggactcaaga    6840
cgatagttac cggataaggc gcagcggtcg ggctgaacgg ggggttcgtg cacacagccc    6900
agcttggagc gaacgaccta caccgaactg agatacctac agcgtgagct atgagaaagc    6960
gccacgcttc ccgaagggag aaaggcggac aggtatccgg taagcggcag ggtcggaaca    7020
ggagagcgca cgagggagct tccagggga acgcctggt atctttatag tcctgtcggg    7080
tttcgccacc tctgacttga gcgtcgattt ttgtgatgct cgtcaggggg gcggagccta    7140
tggaaaaacg ccagcaacgc ggcctttta cggttcctgg ccttttgctg gccttttgct    7200
cacatgttct ttcctgcgtt atcccctgat tctgtggata accgtattac cgcctttgag    7260
tgagctgata ccgctcgccg cagccgaacg accgagcgca gcgagtcagt gagcgaggaa    7320
gcggaagagc gcctgatgcg gtattttctc cttacgcatc tgtgcggtat ttcacaccgc    7380
atatatggtg cactctcagt acaatctgct ctgatgccgc atagttaagc cagtatacac    7440
tccgctatcg ctacgtgact gggtcatggc tgcgccccga caccgcaa cacccgctga     7500
cgcgccctga cgggcttgtc tgctcccggc atccgcttac agacaagctg tgaccgtctc    7560
cgggagctgc atgtgtcaga ggttttcacc gtcatcaccg aaacgcgcga ggcagctgcg    7620
gtaaagctca tcagcgtggt cgtgcagcga ttcacagatg tctgcctgtt catccgcgtc    7680
cagctcgttg agtttctcca gaagcgttaa tgtctggctt ctgataaagc gggccatgtt    7740
aagggcggtt ttttcctgtt tggtcactga tgcctccgtg taaggggat ttctgttcat     7800
gggggtaatg ataccgatga acgagagag atgctcacg atacgggtta ctgatgatga     7860
acatgcccgg ttactggaac gttgtgaggg taaacaactg gcggtatgga tgcggcggga    7920
ccagagaaaa atcactcagg gtcaatgcca gcgcttcgtt aatacagatg taggtgttcc    7980
acagggtagc cagcagcatc ctgcgatgca gatccggaac ataatggtgc agggcgctga    8040
cttccgcgtt tccagacttt acgaaacacg gaaaccgaag accattcatg ttgttgctca    8100
ggtcgcagac gttttgcagc agcagtcgct tcacgttcgc tcgcgtatcg gtgattcatt    8160
ctgctaacca gtaaggcaac cccgccagcc tagccgggtc ctcaacgaca ggagcacgat    8220
catgcgcacc cgtggccagg acccaacgct gcccgaaatt                          8260
```

<210> SEQ ID NO 15
<211> LENGTH: 8260

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta aatctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatctcggta gtgggatacg     900
acgataccga agacagctca tgttatatcc gccgttaac caccatcaaa caggatttc      960
gcctgctggg gcaaaccagc gtggaccgct tgctgcaact ctctcagggc caggcggtga    1020
agggcaatca gctgttgccc gtctcactgg tgaaagaaa aaccaccctg cgcccaata     1080
cgcaaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt cgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga    1500
gcacttcacc aacaaggacc atagcatatg aaaatcgaag aaggtaaact ggtaatctgg    1560
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt tggtggctac    1740
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta taacaaagat ctgctgccga cccgccaaa aacctgggaa    1920
gagatcccgg cgctggataa agaactgaaa gcgaaggta agagcgcgct gatgttcaac    1980
ctgcaagaac cgtacttcac ctggccgctg attgctgctg acgggggtta tgcgttcaag    2040
tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
```

```
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gccgtagcgc tgaagtctta cgaggaagag    2460
ttggcgaaag atccacgtat tgccgccact atggaaaacg cccagaaagg tgaaatcatg    2520
ccgaacatcc cgcagatgtc cgctttctgg tatgccgtgc gtactgcggt gatcaacgcc    2580
gccagcggtc gtcagactgt cgatgccgcc ctggccgccg cgcagactgc cgccgccgcc    2640
gccatggaga caaggcaaat ggcagtggaa caaccactg gtgcggtcac caaccaaacg    2700
gaaacaagct ggcacagcat agactgggcc aagccaacc gtgaggtaaa gaggctgcaa    2760
gtgcgtatcg caaaggctgt gaaggaagga cgctgggca aagtgaaagc tttgcaatgg    2820
ctcctgaccc actcgttcta cggcaaagcc ctcgccgtga acgggtaac tgacaactcg    2880 ggcagcaaaa cacctggtgt ggacgggata acctggtcca cacaagagca gaaagcccaa    2940
gccataaagt ccctcaggag aagaggctac aaaccccaac ccctgaggcg ggtatacatc    3000
ccgaaagcaa gcggcaagca gcgcccgcta ggaatcccga caacgaagga cagggcaatg    3060
caggcattat atgccctagc tctagaacct gtcgcgaaaa ccacagcgga tcggaactca    3120
tacgggttcc gtcaaggacg gtgcacggca gatgctgccg ggcagtgctt cactgtgcta    3180
ggccgatctg actgtgcaaa atatatcctt gatgctgaca tcaccggatg ctttgacaac    3240
attagccacg aatggctact agacaacatc ccgctggaca agaggttct gcggaagtgg    3300 cttaaatctg ggttcgtctg gaaacagcaa ctcttcccaa cccatgctgg gacacctcag    3360
ggaggggtaa tctccccaat gctggccaat atgaccctag atgggatgga agaattgctg    3420
aagaaacacc tcagaaaaca aaagtcaac ctcatacgat atgcagacga ctttgtcgta    3480
actggtgaat caaggaaac cttggaaaag gttacaactg taatccaaga attcctcaag    3540
gaaaggggcc ttaccctatc agaagaaag acaaaggtcg ttcatatcga agaaggattt    3600
gactttcttg gatggaacat tcgcaaatat ggtgagaagc ttctcatcaa acctgcgaag    3660
aagaacatca aggcgttcca caagaaaatc cgagacgcac tgaaggaact cagaacagcc    3720
acccaggaag ctgtgataga cacactcaac ccaattatca aggctgggc taactatcac    3780 agaaaccagg tttccaaaag aatcttcaac agagcggatg acaatatctg gcataaatta    3840
tggcgatggg caaaacgtcg gcacccaaac aaaccagccc gatggacaaa gaacaaatac    3900
ttcatcaaaa tcgggaatag gcactgggtg tttggcacat ggaaaaagga caaagaggga    3960
aggttacggt ccagatacct aattaaagcc ggagatactc gaatccaacg tcatgtcaaa    4020
atcaaggcag acgccaatcc gtttctccca gagtgggcag aatactttga ggaacgcaag    4080
aaactcaaag aagcccctgc tcaatatcgg cgcatccgcc gagaactatg gaagaaacag    4140
ggtggtatct gtccagtatg cggggtgaa attgagcaag acatgctcac tgaaatccac    4200
cacatattgc ccaaacacaa gggtggttct gacgacctgg ataatcttgt cttaatccac    4260
gccaactgtc acaaacaggt gcacagccga gacggtcagc acagccggtt cctcttgaaa    4320
gagggctttg gactgcaggc aagcttggca ctggccgtcg ttttacaacg tcgtgactgg    4380
gaaacccctg gcgttaccca acttaatcgc cttgcagcac atcccccttt cgccagctgg    4440
cgtaatagcg aagaggcccg caccgatcgc ccttcccaac agttgcgcag cctgaatggc    4500
```

```
gaatggcagc ttggctgttt tggcggatga gataagattt tcagcctgat acagattaaa    4560
tcagaacgca gaagcggtct gataaaacag aatttgcctg gcggcagtag cgcggtggtc    4620
ccacctgacc ccatgccgaa ctcagaagtg aaacgccgta gcgccgatgg tagtgtgggg    4680 tctcccatg cgagagtagg gaactgccag gcatcaaata aaacgaaagg ctcagtcgaa    4740
agactgggcc tttcgtttta tctgttgttt gtcggtgaac gctctcctga gtaggacaaa    4800
tccgccggga gcggatttga acgttgcgaa gcaacggccc ggagggtggc gggcaggacg    4860
cccgccataa actgccaggc atcaaattaa gcagaaggcc atcctgacgg atggcctttt    4920
tgcgttctca caaactcttt ttgtttattt ttctaaatac attcaaatat gtatccgctc    4980
atgagacaat aaccctgata atgcttcaa taatattgaa aaaggaagag tatgagtatt    5040
caacatttcc gtgtcgccct tattccctt tttgcggcat tttgccttcc tgttttgct     5100 cacccagaaa cgctggtgaa agtaaaagat gctgaagatc agttgggtgc acgagtgggt    5160
tacatcgaac tggatctcaa cagcggtaag atccttgaga gttttcgccc cgaagaacgt    5220
tctccaatga tgagcacttt taaagttctg ctatgtggcg cggtattatc ccgtgttgac    5280
gccgggcaag agcaactcgg tcgccgcata cactattctc agaatgactt ggttgagtac    5340
tcaccagtca cagaaaagca tcttacggat ggcatgacag taagagaatt atgcagtgct    5400
gccataacca tgagtgataa cactgcggcc aacttacttc tgacaacgat cggaggaccg    5460
aaggagctaa ccgcttttt gcacaacatg ggggatcatg taactcgcct tgatcgttgg    5520
gaaccggagc tgaatgaagc cataccaaac gacgagcgtg acaccacgat gcctgtagca    5580
atggcaacaa cgttgcgcaa actattaact ggcgaactac ttactctagc ttcccggcaa    5640
caattaatag actggatgga ggcggataaa gttgcaggac cacttctgcg ctcggccctt    5700
ccggctggct ggtttattgc tgataaatct ggagccggtg agcgtgggtc tcgcggtatc    5760
attgcagcac tggggccaga tggtaagccc tcccgtatcg tagttatcta cacgacgggg    5820
agtcaggcaa ctatggatga acgaaataga cagatcgctg agataggtgc ctcactgatt    5880
aagcattggt aactgtcaga ccaagtttac tcatatatac tttagattga tttaccccgg    5940
ttgataatca gaaaagcccc aaaaacagga agattgtata agcaaatatt taaattgtaa    6000
acgttaatat tttgttaaaa ttcgcgttaa attttttgtta aatcagctca ttttttaacc    6060
aataggccga atcggcaaa atcccttata aatcaaaaga atagaccgag atagggttga    6120
gtgttgttcc agtttggaac aagagtccac tattaaagaa cgtggactcc aacgtcaaag    6180
ggcgaaaaac cgtctatcag ggcgatggcc cactacgtga accatcaccc aaatcaagtt    6240
ttttggggtc gaggtgccgt aaagcactaa atcggaaccc taaagggagc ccccgattta    6300
gagcttgacg gggaaagccg gcgaacgtgg cgagaaagga agggaagaaa gcgaaaggag    6360
cgggcgctag ggcgctggca agtgtagcgg tcacgctgcg cgtaaccacc acacccgccg    6420
cgcttaatgc gccgctacag ggcgcgtaaa aggatctagg tgaagatcct ttttgataat    6480
ctcatgacca aaatccctta acgtgagttt tcgttccact gagcgtcaga ccccgtagaa    6540
aagatcaaag gatcttcttg agatcctttt tttctgcgcg taatctgctg cttgcaaaca    6600
aaaaaaccac cgctaccagc ggtggtttgt ttgccggatc aagagctacc aactcttttt    6660
ccgaaggtaa ctggcttcag cagagcgcag ataccaaata ctgtccttct agtgtagccg    6720
tagttaggcc accacttcaa gaactctgta gcaccgccta catacctcgc tctgctaatc    6780
ctgttaccag tggctgctgc cagtggcgat aagtcgtgtc ttaccgggtt ggactcaaga    6840
cgatagttac cggataaggc gcagcggtcg ggctgaacgg ggggttcgtg cacacagccc    6900
```

```
agcttggagc gaacgaccta caccgaactg agatacctac agcgtgagct atgagaaagc    6960
gccacgcttc ccgaagggag aaaggcggac aggtatccgg taagcggcag ggtcggaaca    7020
ggagagcgca cgagggagct tccaggggga aacgcctggt atctttatag tcctgtcggg    7080
tttcgccacc tctgacttga gcgtcgattt ttgtgatgct cgtcaggggg gcggagccta    7140
tggaaaaacg ccagcaacgc ggccttttta cggttcctgg ccttttgctg gccttttgct    7200
cacatgttct ttcctgcgtt atcccctgat tctgtggata accgtattac cgcctttgag    7260
tgagctgata ccgctcgccg cagccgaacg accgagcgca gcgagtcagt gagcgaggaa    7320
gcggaagagc gcctgatgcg gtattttctc cttacgcatc tgtgcggtat ttcacaccgc    7380
atatatggtg cactctcagt acaatctgct ctgatgccgc atagttaagc cagtatacac    7440
tccgctatcg ctacgtgact gggtcatggc tgcgccccga cacccgccaa cacccgctga    7500
cgcgccctga cgggcttgtc tgctcccggc atccgcttac agacaagctg tgaccgtctc    7560
cgggagctgc atgtgtcaga ggttttcacc gtcatcaccg aaacgcgcga ggcagctgcg    7620
gtaaagctca tcagcgtggt cgtgcagcga ttcacagatg tctgcctgtt catccgcgtc    7680
cagctcgttg agtttctcca gaagcgttaa tgtctggctt ctgataaagc gggccatgtt    7740
aagggcggtt ttttcctgtt tggtcactga tgcctccgtg taagggggat ttctgttcat    7800
gggggtaatg ataccgatga aacgagagag gatgctcacg atacgggtta ctgatgatga    7860
acatgcccgg ttactggaac gttgtgaggg taaacaactg gcggtatgga tgcggcggga    7920
ccagagaaaa atcactcagg gtcaatgcca gcgcttcgtt aatacagatg taggtgttcc    7980
acagggtagc cagcagcatc ctgcgatgca gatccggaac ataatggtgc agggcgctga    8040
cttccgcgtt tccagacttt acgaaacacg gaaaccgaag accattcatg ttgttgctca    8100
ggtcgcagac gttttgcagc agcagtcgct tcacgttcgc tcgcgtatcg gtgattcatt    8160
ctgctaacca gtaaggcaac cccgccagcc tagccgggtc ctcaacgaca ggagcacgat    8220
catgcgcacc cgtggccagg acccaacgct gcccgaaatt                         8260

<210> SEQ ID NO 16
<211> LENGTH: 8490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta atctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
```

```
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaagaaa aaccacccctg gcgcccaata   1080 cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt cgccgacat cataacggtt   1380 ctggcaaata ttctgaaatg agctgttgac aattaatcat cggctcgtat aatgtgtgga   1440
attgtgagcg gataacaatt tcacacagga acagccagt ccgtttaggt gttttcacga   1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga acccgccaaa aacctgggaa   1920
gagatcccgg cgctggataa agaactgaaa gcgaaaggta agagcgcgct gatgttcaac   1980
ctgcaagaac cgtacttcac ctggccgctg attgctgctg acgggggtta tgcgttcaag   2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgccgcc tggccgccg cgcagactgc cgccgccgcc   2640
gccatgaagg taaacaaact tgtcgtaaaa agcgaacagg acttgagaaa ctgcttggat   2700
cttctttatc aagaagctaa aagggaaaa cattttacg gcatgcttga gttgcttcaa   2760
aatgatgttg tcattttaga agctattcgc aatattaaa gcaataaagg tagcaaaacg   2820
gcggggattg atcagaaaat agtagatgat tatttgctta tgccaacgga aaaggttttc   2880
gggatgataa aagccaaact caatgactat aagcctatac cagtgagaag gtgcaacaag   2940
cccaaaggaa atgccaaaag ctcaaaaaga aaaggcaata gtccgaatga ggaagggaa   3000
```

```
acgaggccct taggaatatc cgcagtgacg gatagaatca tccaagagat gctacggata    3060
gtgctcgagc cgattttcga agcccaattc tatccgcaca gttatgggtt cagaccgtat    3120
cgctccaccg aacatgcctt agcctggatg ctgaaaatca tcaacggaag caaactgtat    3180
tgggttgtaa aaggtgacat tgaaagttat tttgatcaca tcaatcataa gaagcttctg    3240
aacatcatgt ggaatatggg cgttagggat aaacgggtac tatgcatcgt taagaaaatg    3300
ctgaaggcgg ggcaagtgat acaaggtaaa ttctatccaa ccgctaaggg gattcctcag    3360
ggaggaatta ttagcccgtt gttggctaat gtatatctca acagctttga ctggatggtt    3420
ggccaagaat atgagtatca ccctaataac gcaaactatc gggaaaagaa aaacgcatta    3480
gcggcgttaa ggaacaaggg acatcatccc gtcttttaca ttcgttatgc tgatgattgg    3540
gttattctta cggatacgaa agaatatgcg gaaaaaataa gggagcaatg taagcagtat    3600
ttagcctgtg agttgcactt aactctatcg gatgagaaaa cgttcattgc agatatccgc    3660
gaacaacggg ttaagtttct aggcttttgt attgaggcag gaaagcggcg ttttcataaa    3720
aaaggattcg ccgctagaat gattcccgat atggaaaaag tcaatgccaa ggtcaaagaa    3780
attaagcgcg atattcgatt gttaagaacg agaaaatcgg aattagagaa agcccttgat    3840
attgaaaaca ttaacaccaa aattatagga ttagccaatc atctaaaaat aggcatttcc    3900
aagtacatta tgggcaaagt agatcgcgtc attgaagaga cagcctaccg cacctgggtt    3960
aaaatgtatg ggaagaaaa agcggcgcaa tataaaaggc ctgtgtcaga gtttcacaat    4020
cggattgaca gacataaagg ctatcaaatg aaacattttt ctgtcgtcac agaggatggc    4080
ataagagtag ggattaccca tgcaaaaata acgcctatac agtatgcaac agtattcaaa    4140
caagaaatga ccccatacac tgcagacggc agaaaaatgt atgaagaaaa gcatagaaaa    4200
atacgattgc cggataaaat gagtctgttc gatcacgatt cgatattcat ctacatttta    4260
tctgagcata atgatgggaa atataatctt gaatatttct aaatagggt gaatgtattt    4320
cacagagata aaggaaaatg caaaatatgt gccgtatact taagtcccgg taacttccac    4380
tgccatcata ttgacccgag taaacctta agtgagatca ataagaccgt taatctaatt    4440
agcttatgca accaatgcca taggcttgtc catagcaacc aagaaccgcc gtttacagaa    4500
cgaaaaatgt ttgacaaact aacgaaatat aggaacaagc tgaaaatata aggatcctct    4560
agctgcaggc aagcttggca ctggccgtcg ttttacaacg tcgtgactgg gaaaaccctg    4620
gcgttaccca acttaatcgc cttgcagcac atcccccttt cgccagctgg cgtaatagcg    4680
aagaggcccg caccgatcgc ccttcccaac agttgcgcag cctgaatggc gaatggcagc    4740
ttggctgttt tggcggatga gataagattt tcagcctgat acagattaaa tcagaacgca    4800
gaagcggtct gataaaacag aatttgcctg gcggcagtag cgcggtggtc ccacctgacc    4860
ccatgccgaa ctcagaagtg aaacgccgta gcgccgatgg tagtgtgggg tctccccatg    4920
cgagagtagg gaactgccag gcatcaaata aaacgaaagg ctcagtcgaa agactgggcc    4980
tttcgtttta tctgttgttt gtcggtgaac gctctcctga gtaggacaaa tccgccggga    5040
gcggatttga acgttgcgaa gcaacggccc ggagggtggc gggcaggacg cccgccataa    5100
actgccaggc atcaaattaa gcagaaggcc atcctgacgg atggcctttt tgcgtttcta    5160
caaactcttt ttgtttattt ttctaaatac attcaaatat gtatccgctc atgagacaat    5220
aaccctgata aatgcttcaa taatattgaa aaaggaagag tatgagtatt caacatttcc    5280
gtgtcgccct tattcccttt tttgcggcat tttgccttcc tgttttttgct cacccagaaa    5340
cgctggtgaa agtaaaagat gctgaagatc agttgggtgc acgagtgggt tacatcgaac    5400
```

```
tggatctcaa cagcggtaag atccttgaga gttttcgccc cgaagaacgt tctccaatga    5460
tgagcacttt taaagttctg ctatgtggcg cggtattatc ccgtgttgac gccgggcaag    5520
agcaactcgg tcgccgcata cactattctc agaatgactt ggttgagtac tcaccagtca    5580
cagaaaagca tcttacggat ggcatgacag taagagaatt atgcagtgct gccataacca    5640
tgagtgataa cactgcggcc aacttacttc tgacaacgat cggaggaccg aaggagctaa    5700
ccgcttttttt gcacaacatg ggggatcatg taactcgcct tgatcgttgg gaaccggagc    5760
tgaatgaagc cataccaaac gacgagcgtg acaccacgat gcctgtagca atggcaacaa    5820
cgttgcgcaa actattaact ggcgaactac ttactctagc ttcccggcaa caattaatag    5880
actggatgga ggcggataaa gttgcaggac cacttctgcg ctcggccctt ccggctggct    5940
ggtttattgc tgataaatct ggagccgtg agcgtgggtc tcgcggtatc attgcagcac    6000
tggggccaga tggtaagccc tcccgtatcg tagttatcta cacgacgggg agtcaggcaa    6060
ctatggatga acgaaataga cagatcgctg agataggtgc ctcactgatt aagcattggt    6120
aactgtcaga ccaagtttac tcatatatac tttagattga tttaccccgg ttgataatca    6180
gaaaagcccc aaaaacagga agattgtata agcaaatatt taaattgtaa acgttaatat    6240
tttgttaaaa ttcgcgttaa attttttgtta aatcagctca tttttttaacc aataggccga    6300
aatcggcaaa atcccttata atcaaaaga atagaccgag atagggttga gtgttgttcc    6360
agtttggaac aagagtccac tattaaagaa cgtggactcc aacgtcaaag ggcgaaaaac    6420
cgtctatcag ggcgatggcc cactacgtga accatcaccc aaatcaagtt ttttggggtc    6480
gaggtgccgt aaagcactaa atcggaaccc taaagggagc ccccgattta gagcttgacg    6540
gggaaagccg gcgaacgtgg cgagaaagga agggaagaaa gcgaaaggag cgggcgctag    6600
ggcgctggca agtgtagcgg tcacgctgcg cgtaaccacc acacccgccg cgcttaatgc    6660
gccgctacag ggcgcgtaaa aggatctagg tgaagatcct ttttgataat ctcatgacca    6720
aaatccctta acgtgagttt cgttccact gagcgtcaga ccccgtagaa aagatcaaag    6780
gatcttcttg agatcctttt tttctgcgcg taatctgctg cttgcaaaca aaaaaaccac    6840
cgctaccagc ggtggtttgt ttgccggatc aagagctacc aactctttttt ccgaaggtaa    6900
ctggcttcag cagagcgcag ataccaaata ctgtccttct agtgtagccg tagttaggcc    6960
accacttcaa gaactctgta gcaccgccta catacctcgc tctgctaatc ctgttaccag    7020
tggctgctgc cagtggcgat aagtcgtgtc ttaccgggtt ggactcaaga cgatagttac    7080
cggataaggc gcagcggtcg ggctgaacgg ggggttcgtg cacacagccc agcttggagc    7140
gaacgaccta caccgaactg agatacctac agcgtgagct atgagaaagc gccacgcttc    7200
ccgaagggag aaaggcggac aggtatccgg taagcggcag ggtcggaaca ggagagcgca    7260
cgagggagct tccaggggga aacgcctggt atctttatag tcctgtcggg tttcgccacc    7320
tctgacttga gcgtcgattt ttgtgatgct cgtcaggggg gcggagccta tggaaaaacg    7380
ccagcaacgc ggccttttta cggttcctgg ccttttgctg gccttttgct cacatgttct    7440
ttcctgcgtt atcccctgat tctgtggata accgtattac cgcctttgag tgagctgata    7500
ccgctcgccg cagccgaacg accgagcgca gcgagtcagt gagcgaggaa gcggaagagc    7560
gcctgatgcg gtattttctc cttacgcatc tgtgcggtat ttcacaccgc atatatggtg    7620
cactctcagt acaatctgct ctgatgccgc atagttaagc cagtatacac tccgctatcg    7680
ctacgtgact gggtcatggc tgcgccccga cacccgccaa cacccgctga cgcgccctga    7740
```

```
cgggcttgtc tgctcccggc atccgcttac agacaagctg tgaccgtctc cgggagctgc    7800
atgtgtcaga ggttttcacc gtcatcaccg aaacgcgcga ggcagctgcg gtaaagctca    7860
tcagcgtggt cgtgcagcga ttcacagatg tctgcctgtt catccgcgtc cagctcgttg    7920
agtttctcca gaagcgttaa tgtctggctt ctgataaagc gggccatgtt aagggcggtt    7980
ttttcctgtt tggtcactga tgcctccgtg taagggggat ttctgttcat ggggtaatg     8040 ataccgatga acagagagag gatgctcacg ataccgggtta ctgatgatga acatgcccgg   8100
ttactggaac gttgtgaggg taaacaactg gcggtatgga tgcggcggga ccagagaaaa   8160
atcactcagg gtcaatgcca gcgcttcgtt aatacagatg taggtgttcc acagggtagc   8220
cagcagcatc ctgcgatgca gatccggaac ataatggtgc agggcgctga cttccgcgtt   8280
tccagacttt acgaaacacg gaaaccgaag accattcatg ttgttgctca ggtcgcagac   8340
gttttgcagc agcagtcgct tcacgttcgc tcgcgtatcg gtgattcatt ctgctaacca   8400
gtaaggcaac cccgccagcc tagccgggtc ctcaacgaca ggagcacgat catgcgcacc   8460
cgtggccagg acccaacgct gcccgaaatt                                    8490
```

<210> SEQ ID NO 17
<211> LENGTH: 7834
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg     360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa accaccctg gcgcccaata    1080 cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
```

```
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt  ccgtttaggt gttttcacga    1500
gcacttcacc aacaaggacc atagcatatg aaaatcgaag aaggtaaact ggtaatctgg    1560
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt ggtggctac     1740 gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta taacaaagat ctgctgccga acccgccaaa aacctgggaa    1920
gagatcccgg cgctggataa agaactgaaa gcgaaggta  agagcgcgct gatgttcaac    1980
ctgcaagaac cgtacttcac ctggccgctg attgctgctg acggggtta  tgcgttcaag    2040 tatgaaaacg gcaagtacga cattaaagac gtgggcgtgg ataacgctgg cgcgaaagcg    2100
ggtctgacct tcctggttga cctgattaaa acaaacaca  tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gccgtagcgc tgaagtctta cgaggaagag    2460
ttggcgaaag atccacgtat tgccgccact atggaaaacg cccagaaagg tgaaatcatg    2520
ccgaacatcc cgcagatgtc cgctttctgg tatgccgtgc gtactgcggt gatcaacgcc    2580
gccagcggtc gtcagactgt cgatgccgcc ctggccgccg cgcagactgc cgccgccgcc    2640
gccatggctt tgttggaacg catcttagcg agagacaacc tcatcacggc gctcaaacgg    2700
gtcgaagcca accaaggagc accgggaatc gacgagtat  caaccgatca actccgtgat    2760
tacatccgcg ctcactggag cacgatccac gcccaactct ggcgggaaac ctaccggccg    2820
gcgcctgtcc gcagggtcga atcccgaaa  ccgggcggcg gcacacggca gctaggcatt    2880
cccaccgtgg tggaccggct gatccaacaa gccattcttc aagaactcac acccattttc    2940
gatccagact tctcctcttc cagcttcgga ttccgtccgg gccgcaacgc ccacgatgcc    3000
gtgcggcaag cgcaaggcta catccaggaa gggtatcggt acgtggtcga catggacctg    3060
gaaaagttct tgatcgggt  caaccatgac atcttgatga gtcgggtggc ccgaaaagtc    3120
aaggataaac gcgtgctgaa actgatccgt gcctacctgc aagccggcgt tatgatcgaa    3180
ggggtgaagg tgcagacgga ggaagggacg ccgcaaggcg gccccctcag cccccctgctg    3240 gcgaacatcc ttctcgacga tttagacaag gaattggaga agcgaggatt gaaattctgc    3300
cgttacgcag atgactgcaa catctatgtg aaaagtctgc gggcaggaca acgggtgaaa    3360
caaagcatcc aacggttctt ggagaaaacg ctcaaactca agtaaacga  ggagaaaagt    3420 gcggtggacc gcccgtggaa acgggccttt ctggggttta gcttcacacc ggaacgaaaa    3480
gcgcgaatcc ggctcgcccc aaggtcgatt caacgtctga aacagcggat tcgacagctg    3540 accaaccccaa actggagcat atcgatgcca gaacgaattc atcgcgtcaa tcaatacgtc    3600
atgggatgga tcgggtattt tcggctcgtc gaaaccccgt ctgtccttca gaccatcgaa    3660
```

```
ggatggattc ggaggaggct tcgactctgt caatggcttc aatggaaacg ggtcagaacc    3720
agaatccgtg agttaagagc gctggggctg aaagagacag cggtgatgga gatcgccaat    3780
acccgaaaag gagcttggcg aacaacgaaa acgccgcaac tccaccaggc cctgggcaag    3840
acctactgga ccgctcaagg gctcaagagt ttgacgcaac gatatttcga actccgtcaa    3900
ggttgactgc aggcaagctt ggcactggcc gtcgttttac aacgtcgtga ctgggaaaac    3960
cctggcgtta cccaacttaa tcgccttgca gcacatcccc ctttcgccag ctggcgtaat    4020
agcgaagagg cccgcaccga tcgcccttcc caacagttgc gcagcctgaa tggcgaatgg    4080
cagcttggct gttttggcgg atgagataag attttcagcc tgatacagat taaatcagaa    4140
cgcagaagcg gtctgataaa acagaatttg cctggcggca gtagcgcggt ggtcccacct    4200
gaccccatgc cgaactcaga agtgaaacgc cgtagcgccg atggtagtgt ggggtctccc    4260
catgcgagag tagggaactg ccaggcatca aataaaacga aaggctcagt cgaaagactg    4320
ggcctttcgt tttatctgtt gtttgtcggt gaacgctctc ctgagtagga caaatccgcc    4380
gggagcggat ttgaacgttg cgaagcaacg gcccggaggg tggcgggcag gacgcccgcc    4440
ataaactgcc aggcatcaaa ttaagcagaa ggccatcctg acggatggcc tttttgcgtt    4500
tctacaaact cttttgtttt atttttctaa atacattcaa atatgtatcc gctcatgaga    4560
caataaccct gataaatgct tcaataatat tgaaaaagga agagtatgag tattcaacat    4620
ttccgtgtcg cccttattcc cttttttgcg gcattttgcc ttcctgtttt tgctcaccca    4680
gaaacgctgg tgaaagtaaa agatgctgaa gatcagttgg gtgcacgagt gggttacatc    4740
gaactggatc tcaacagcgg taagatcctt gagagttttc gccccgaaga acgttctcca    4800
atgatgagca cttttaaagt tctgctatgt ggcgcggtat tatcccgtgt tgacgccggg    4860
caagagcaac tcggtcgccg catacactat tctcagaatg acttggttga gtactcacca    4920
gtcacagaaa agcatcttac ggatggcatg acagtaagag aattatgcag tgctgccata    4980
accatgagtg ataacactgc ggccaactta cttctgacaa cgatcggagg accgaaggag    5040
ctaaccgctt ttttgcacaa catgggggat catgtaactc gccttgatcg ttgggaaccg    5100
gagctgaatg aagccatacc aaacgacgag cgtgacacca cgatgcctgt agcaatggca    5160
acaacgttgc gcaaactatt aactggcgaa ctacttactc tagcttcccg gcaacaatta    5220
atagactgga tggaggcgga taaagttgca ggaccacttc tgcgctcggc ccttccggct    5280
ggctggttta ttgctgataa atctggagcc ggtgagcgtg ggtctcgcgg tatcattgca    5340
gcactggggc cagatggtaa gccctcccgt atcgtagtta tctacacgac ggggagtcag    5400
gcaactatgg atgaacgaaa tagacagatc gctgagatag gtgcctcact gattaagcat    5460
tggtaactgt cagaccaagt ttactcatat atactttaga ttgatttacc ccggttgata    5520
atcagaaaag ccccaaaaac aggaagattg tataagcaaa tatttaaatt gtaaacgtta    5580
atattttgtt aaaattcgcg ttaaattttt gttaaatcag ctcattttt  aaccaatagg    5640 ccgaaatcgg caaaatccct tataaatcaa aagaatagac cgagataggg ttgagtgttg    5700
ttccagtttg gaacaagagt ccactattaa agaacgtgga ctccaacgtc aaagggcgaa    5760
aaaccgtcta tcagggcgat ggcccactac gtgaaccatc acccaaatca agttttttgg    5820
ggtcgaggtg ccgtaaagca ctaaatcgga accctaaagg gagcccccga tttagagctt    5880
gacggggaaa gccggcgaac gtggcgagaa aggaagggaa gaaagcgaaa ggagcgggcg    5940
ctagggcgct ggcaagtgta gcggtcacgc tgcgcgtaac caccacaccc gccgcgctta    6000
```

```
atgcgccgct acagggcgcg taaaaggatc taggtgaaga tccttttga taatctcatg   6060
accaaaatcc cttaacgtga gttttcgttc cactgagcgt cagacccgt agaaaagatc    6120
aaaggatctt cttgagatcc ttttttctg cgcgtaatct gctgcttgca acaaaaaaa    6180
ccaccgctac cagcggtggt ttgtttgccg gatcaagagc taccaactct ttttccgaag   6240
gtaactggct tcagcagagc gcagatacca aatactgtcc ttctagtgta gccgtagtta   6300
ggccaccact tcaagaactc tgtagcaccg cctacatacc tcgctctgct aatcctgtta   6360
ccagtggctg ctgccagtgg cgataagtcg tgtcttaccg ggttggactc aagacgatag   6420
ttaccggata aggcgcagcg tcgggctga acgggggggtt cgtgcacaca gcccagcttg    6480
gagcgaacga cctacaccga actgagatac ctacagcgtg agctatgaga aagcgccacg   6540
cttcccgaag ggagaaaggc ggacaggtat ccggtaagcg gcagggtcgg aacaggagag   6600
cgcacgaggg agcttccagg gggaaacgcc tggtatcttt atagtcctgt cgggtttcgc   6660
cacctctgac ttgagcgtcg atttttgtga tgctcgtcag gggggcggag cctatggaaa   6720
aacgccagca acgcggcctt tttacggttc ctggccttt gctggccttt tgctcacatg    6780
ttctttcctg cgttatcccc tgattctgtg gataaccgta ttaccgcctt tgagtgagct   6840
gataccgctc gccgcagccg aacgaccgag cgcagcgagt cagtgagcga ggaagcggaa   6900
gagcgcctga tgcggtattt tctccttacg catctgtgcg gtatttcaca ccgcatatat   6960
ggtgcactct cagtacaatc tgctctgatg ccgcatagtt aagccagtat acactccgct   7020
atcgctacgt gactgggtca tggctgcgcc ccgacacccg ccaacacccg ctgacgcgcc   7080
ctgacgggct tgtctgctcc cggcatccgc ttacagacaa gctgtgaccg tctccgggag   7140
ctgcatgtgt cagaggtttt caccgtcatc accgaaacgc gcgaggcagc tgcggtaaag   7200
ctcatcagcg tggtcgtgca gcgattcaca gatgtctgcc tgttcatccg cgtccagctc   7260
gttgagtttc tccagaagcg ttaatgtctg gcttctgata aagcgggcca tgttaagggc   7320
ggttttttcc tgtttggtca ctgatgcctc cgtgtaaggg ggatttctgt tcatgggggt   7380
aatgataccg atgaaacgag agaggatgct cacgatacgg gttactgatg atgaacatgc   7440
ccggttactg gaacgttgtg agggtaaaca actggcggta tggatgcggc gggaccagag   7500
aaaaatcact cagggtcaat gccagcgctt cgttaataca gatgtaggtg ttccacaggg   7560
tagccagcag catcctgcga tgcagatccg gaacataatg gtgcagggcg ctgacttccg   7620
cgtttccaga ctttacgaaa cacggaaacc gaagaccatt catgttgttg ctcaggtcgc   7680
agacgttttg cagcagcagt cgcttcacgt tcgctcgcgt atcggtgatt cattctgcta   7740
accagtaagg caaccccgcc agcctagccg ggtcctcaac gacaggagca cgatcatgcg   7800
cacccgtggc caggacccaa cgctgcccga aatt                              7834
```

<210> SEQ ID NO 18  
<211> LENGTH: 5  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 18

Ala Ala Ala Glu Phe  
1               5

<210> SEQ ID NO 19  
<211> LENGTH: 35

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Thr Val Asp Glu Ala Leu Lys Asp Ala Gln Thr Asn Ser Ser Ser Asn
1               5                   10                  15

Asn Asn Asn Asn Asn Asn Asn Asn Asn Leu Glu Asn Leu Tyr Phe Gln
            20                  25                  30

Gly Glu Phe
        35

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Val Asp Ala Ala Leu Ala Ala Ala Gln Thr Ala Ala Ala Ala Ala
1               5                   10                  15

<210> SEQ ID NO 21
<211> LENGTH: 1200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gaatacaagc ttgggcgtgt ctcaaaatct ctgatgttac attgcacaag ataaaaatat      60
atcatcatga caataaaaac tgtctgctta cataaacagt aatacaaggg gtgttatgag     120
ccatattcaa cgggaaacgt cttgctcgag gccgcgatta aattccaaca tggatgctga     180
tttatatggg tataaatggg ctcgcgataa tgtcgggcaa tcaggtgcga caatctatcg     240
attgtatggg aagcccgatg cgccagagtt gtttctgaaa catggcaaag gtagcgttgc     300
caatgatgtt acagatgaga tggtcagact aaactggctg acggaattta tgcctcttcc     360
gaccatcaag cattttatcc gtactcctga tgatgcatgg ttactcacca ctgcgatccc     420
cgggaaaaca gcattccagg tattagaaga atatcctgag tcaggtgaaa atattgttga     480
tgcgctggca gtgttcctgc gccggttgca ttcgattcct gtttgtaatt gtccttttaa     540
cagcgatcgc gtatttcgtc tcgctcaggc gcaatcacga tgaataacg gtttggttga     600 tgcgagtgat tttgatgacg agcgtaatgg ctggcctgtt gaacaagtct ggaaagaaat     660
gcataagctt ttgccattct caccggattc agtcgtcact catggtgatt tctcacttga     720
taaccttatt tttgacgagg ggaaattaat aggttgtatt gatgttggac gagtcggaat     780
cgcagaccga taccaggatc ttgccatcct atggaactgc ctcggtgagt tttctccttc     840
attacagaaa cggctttttc aaaaatatgg tattgataat cctgatatga ataaattgca     900
gtttcatttg atgctcgatg agttttttcta atcagaattg gttaattggt tgtaacactg     960
gcagagcatt acgctgactt gacgggacgg cggctttgtt gaataaatcg aactttgct    1020 gagttgaagg atcagatcac gcatcttccc gacaacgcag accgttccgt ggcaaagcaa    1080
aagttcaaaa tcaccaactg gtccacctac aacaaagctc tcatcaaccg tggcgactct    1140
```
agaggatccc cgggcgagct cccaaaaaaa aaaaaaaaa aaaaaaaaaa aaaccgaatt    1200

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acaaataggg gttccgcgca c                                              21

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gttggtgacc gcaccagt                                                  18

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aacgcggtaa gcccgta                                                   17

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aatggacgat atcccgca                                                  18

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Ile Cys Trp Phe Gly Asp Glu Ala Thr Ser Gly Ser Gly His His
1               5                   10                  15

His His His His
        20

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Asn Ile Cys Trp Phe Gly Ala Ala Ala Ala
1               5                   10

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgcctttga gtgagctgat accgctcgcc gcagccg                             37

<210> SEQ ID NO 29
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggtggaccag ttggtgattt tgaacttttg ctttgccacg gaac                     44

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gggtataaat gggctcgcg                                                 19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgggcttccc atacaatcg                                                 19

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
tcgggcaatc aggtgcgaca atc                                            23

<210> SEQ ID NO 33
<211> LENGTH: 70
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 33
gggtataaat gggctcgcga taatgtcggg caatcaggtg cgacaatcta tcgattgtat    60
gggaagcccg    70

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgctcaggcg caatcac    17

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccagccatta cgctcgtcat    20

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
atgaataacg gtttggttga tgcgagtga    29

<210> SEQ ID NO 37
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgctcaggcg caatcacgaa tgaataacgg tttggttgat gcgagtgatt ttgatgacga    60
gcgtaatggc tgg    73

<210> SEQ ID NO 38
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

-continued

Thr Ala Thr Lys Lys Tyr Glu Gln Glu Ile Asp Val Arg Val Gln
                35                  40                  45

Ile Asp Arg Lys Ser Gly Asp Phe Asp Thr Phe Arg Arg Trp Leu Val
 50                  55                  60

Val Asp Glu Val Thr Gln Pro Thr Lys Glu Ile Thr Leu Glu Ala Ala
 65                  70                  75                  80

Arg Tyr Glu Asp Glu Ser Leu Asn Leu Gly Asp Tyr Val Glu Asp Gln
                 85                  90                  95

Ile Glu Ser Val Thr Phe Asp Arg Ile Thr Thr Gln Thr Ala Lys Gln
                100                 105                 110

Val Ile Val Gln Lys Val Arg Glu Ala Glu Arg Ala Met Val Val Asp
                115                 120                 125

Gln Phe Arg Glu His Glu Gly Glu Ile Ile Thr Gly Val Val Lys Lys
130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
                180                 185                 190

Ala Gln Leu Phe Val Thr Arg Ser Lys Pro Glu Met Leu Ile Glu Leu
                195                 200                 205

Phe Arg Ile Glu Val Pro Glu Ile Gly Glu Glu Val Ile Glu Ile Lys
                210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
                260                 265                 270

Ile Val Leu Trp Asp Asp Asn Pro Ala Gln Phe Val Ile Asn Ala Met
                275                 280                 285

Ala Pro Ala Asp Val Ala Ser Ile Val Val Asp Glu Asp Lys His Thr
290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
                340                 345                 350

His Ala Ala Ile Asp Thr Phe Thr Lys Tyr Leu Asp Ile Asp Glu Asp
                355                 360                 365

Phe Ala Thr Val Leu Val Glu Glu Gly Phe Ser Thr Leu Glu Glu Leu
                370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
                420                 425                 430

Asp Leu Leu Asn Leu Glu Gly Val Asp Arg Asp Leu Ala Phe Lys Leu
                435                 440                 445

Ala Ala Arg Gly Val Cys Thr Leu Glu Asp Leu Ala Glu Gln Gly Ile

```
                450                 455                 460
Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly
                485                 490
```

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tttttttttt tttttttttt tttttttttt tttttttttt tt                    42

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Ala Gly Asp
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Ala Asp Asp
1

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 42

His His His His His His
1               5

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Met Asp Asp
1

<210> SEQ ID NO 44

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Val Asp Glu Ala Leu Lys Asp Ala Gln Thr Asn Ser Ser Ser Asn
1               5                   10                  15

Asn Asn Asn Asn Asn Asn Asn Asn Asn Leu
            20                  25

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Val Asp Ala Ala Leu Ala Ala Ala Gln Thr Ala Ala Ala Ala Ala
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Ala Ala Arg Asn Ile Cys Trp Phe Gly Ala Ala Ala Ala Ala
1               5                   10                  15
```